(12) United States Patent
Kamal et al.

(10) Patent No.: US 8,809,321 B2
(45) Date of Patent: Aug. 19, 2014

(54) DIARYL ETHER LINKED PYRROLO [2,1-C][1,4] BENZODIAZEPINE HYBRIDS AND PROCESS FOR THE PREPARATION THEREOF

(75) Inventors: Ahmed Kamal, Hyderabad (IN); Arutla Viswanath, Hyderabad (IN); Jayanti Naga Srirama Chandra Murty, Hyderabad (IN); Earla Vijaya Bharathi, Hyderabad (IN); Gadupudi Ramakrishna, Hyderabad (IN); Farheen Sulthana, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 13/256,601

(22) PCT Filed: Mar. 30, 2011

(86) PCT No.: PCT/IB2011/000670
§ 371 (c)(1),
(2), (4) Date: Feb. 27, 2012

(87) PCT Pub. No.: WO2012/110840
PCT Pub. Date: Aug. 23, 2012

(65) Prior Publication Data
US 2013/0317011 A1 Nov. 28, 2013

(30) Foreign Application Priority Data
Feb. 15, 2011 (IN) .............. 390/DEL/2011

(51) Int. Cl.
*C07D 487/00* (2006.01)
*A61K 31/407* (2006.01)
*A61P 35/00* (2006.01)

(52) U.S. Cl.
USPC .......................... 514/220; 540/496

(58) Field of Classification Search
USPC .......................... 514/220; 540/496
See application file for complete search history.

(56) References Cited

U.S. PATENT DOCUMENTS

2007/0082891 A1    4/2007 Kamal et al.

FOREIGN PATENT DOCUMENTS

WO    WO 2004/087712 A1    10/2004
WO    WO 2009/118748 A1    10/2009

*Primary Examiner* — Bruck Kifle
(74) *Attorney, Agent, or Firm* — Knobbe Martens Olson & Bear, LLP.

(57) ABSTRACT

The present invention provides a compound of general formula A, useful as potential anticancer agents against eleven human cancer cell lines. The present invention further provides a process for the preparation of diaryl ether linked pyrrolo[2,1-c][1,4]benzodi azepine conjugates attached through different alkane spacers of general formula A.

GENERAL FORMULA A

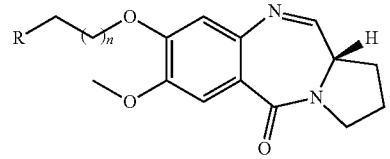

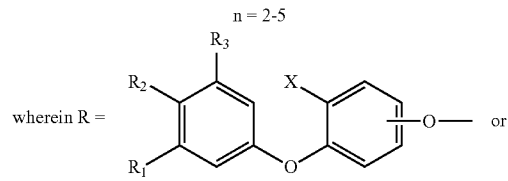

wherein $R_1$, $R_2$, $R_3$ = H or OMe;
$X = NO_2, NH_2, F, I$;
n = 2, 3, 4 and 5.

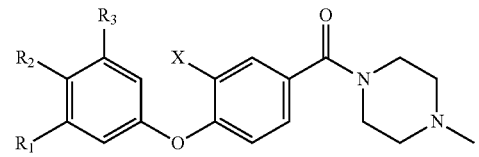

19 Claims, 2 Drawing Sheets

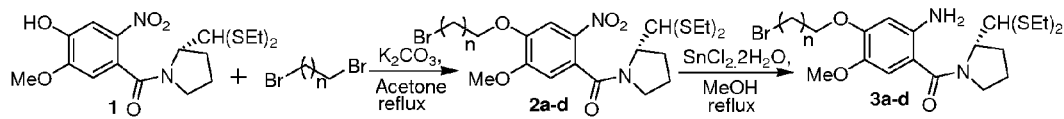

3a (n = 2) 3b (n = 3) 3c (n = 4) 3d (n = 5)

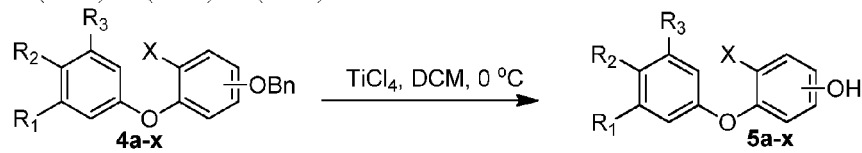

For 4a R$_1$, R$_3$ =H; R$_2$ =OMe; X =3-amino
4b R$_3$ =H; R$_1$, R$_2$ =OMe; X =3-amino
4c R$_1$, R$_2$, R$_3$ =OMe; X =3-amino
4d R$_1$, R$_3$ =H; R$_2$ =OMe; X =3-fluoro
4e R$_3$ =H; R$_1$, R$_2$ =OMe; X =3-fluoro
4f R$_1$, R$_2$, R$_3$ =OMe; X =3-fluoro
4g R$_1$, R$_3$ =H; R$_2$ =OMe; X =3-iodo
4h R$_3$ =H; R$_1$, R$_2$ =OMe; X =3-iodo
4i R$_1$, R$_2$, R$_3$ =OMe; X =3-iodo
4j R$_1$, R$_3$ =H; R$_2$ =OMe; X =3-nitro
4k R$_3$ =H; R$_1$, R$_2$ =OMe; X =3-nitro
4l R$_1$, R$_2$, R$_3$ =OMe; X =3-nitro
4m R$_1$, R$_3$ =H; R$_2$ =OMe; X =4-amino
4n R$_3$ =H; R$_1$, R$_2$ =OMe; X =4-amino
4o R$_1$, R$_2$, R$_3$ =OMe; X =4-amino
4p R$_1$, R$_3$ =H; R$_2$ =OMe; X =4-fluoro
4q R$_3$ =H; R$_1$, R$_2$ =OMe; X =3-fluoro
4r R$_1$, R$_2$, R$_3$ =OMe; X =4-fluoro
4s R$_1$, R$_3$ =H; R$_2$ =OMe; X =4-iodo
4t R$_3$ =H; R$_1$, R$_2$ =OMe; X =4-iodo
4u R$_1$, R$_2$, R$_3$ =OMe; X =4-iodo
4v R$_1$, R$_3$ =H; R$_2$ =OMe; X =4-nitro
4w R$_3$ =H; R$_1$, R$_2$ =OMe; X =4-nitro
4x R$_1$, R$_2$, R$_3$ =OMe; X =4-nitro For 5a R$_1$, R$_3$ =H; R$_2$ =OMe; X =3-amino
5b R$_3$ =H; R$_1$, R$_2$ =OMe; X =3-amino
5c R$_1$, R$_2$, R$_3$ =OMe; X =3-amino
5d R$_1$, R$_3$ =H; R$_2$ =OMe; X =3-fluoro
5e R$_3$ =H; R$_1$, R$_2$ =OMe; X =3-fluoro
5f R$_1$, R$_2$, R$_3$ =OMe; X =3-fluoro
5g R$_1$, R$_3$ =H; R$_2$ =OMe; X =3-iodo
5h R$_3$ =H; R$_1$, R$_2$ =OMe; X =3-iodo
5i R$_1$, R$_2$, R$_3$ =OMe; X =3-iodo
5j R$_1$, R$_3$ =H; R$_2$ =OMe; X =3-nitro
5k R$_3$ =H; R$_1$, R$_2$ =OMe; X =3-nitro
5l R$_1$, R$_2$, R$_3$ =OMe; X =3-nitro
5m R$_1$, R$_3$ =H; R$_2$ =OMe; X =4-amino
5n R$_3$ =H; R$_1$, R$_2$ =OMe; X =4-amino
5o R$_1$, R$_2$, R$_3$ =OMe; X =4-amino
5p R$_1$, R$_3$ =H; R$_2$ =OMe; X =4-fluoro
5q R$_3$ =H; R$_1$, R$_2$ =OMe; X =3-fluoro
5r R$_1$, R$_2$, R$_3$ =OMe; X =4-fluoro
5s R$_1$, R$_3$ =H; R$_2$ =OMe; X =4-iodo
5t R$_3$ =H; R$_1$, R$_2$ =OMe; X =4-iodo
5u R$_1$, R$_2$, R$_3$ =OMe; X =4-iodo
5v R$_1$, R$_3$ =H; R$_2$ =OMe; X =4-nitro
5w R$_3$ =H; R$_1$, R$_2$ =OMe; X =4-nitro
5x R$_1$, R$_2$, R$_3$ =OMe; X =4-nitro

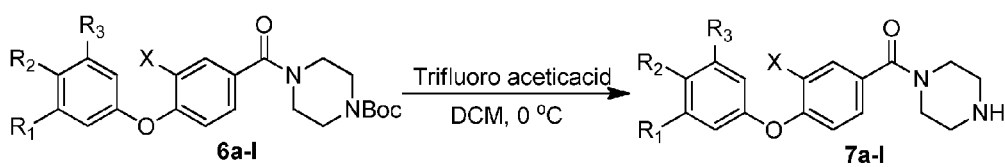

For 6a R$_1$, R$_3$ =H; R$_2$ =OMe; X =amine
6b R$_3$ =H; R$_1$, R$_2$ =OMe; X =amine
6c R$_1$, R$_2$, R$_3$ =OMe; X =3-amine
6d R$_1$, R$_3$ =H; R$_2$ =OMe; X =fluoro
6e R$_3$ =H; R$_1$, R$_2$ =OMe; X =fluoro
6f R$_1$, R$_2$, R$_3$ =OMe; X =fluoro
6g R$_1$, R$_3$ =H; R$_2$ =OMe; X =iodo
6h R$_3$ =H; R$_1$, R$_2$ =OMe; X =iodo
6i R$_1$, R$_2$, R$_3$ =OMe; X =iodo
6j R$_1$, R$_3$ =H; R$_2$ =OMe; X =nitro
6k R$_3$ =H; R$_1$, R$_2$ =OMe; X =nitro
6l R$_1$, R$_2$, R$_3$ =OMe; X =nitro For 7a R$_1$, R$_3$ =H; R$_2$ =OMe; X =amine
7b R$_3$ =H; R$_1$, R$_2$ =OMe; X =amine
7c R$_1$, R$_2$, R$_3$ =OMe; X =3-amine
7d R$_1$, R$_3$ =H; R$_2$ =OMe; X =fluoro
7e R$_3$ =H; R$_1$, R$_2$ =OMe; X =fluoro
7f R$_1$, R$_2$, R$_3$ =OMe; X =fluoro
7g R$_1$, R$_3$ =H; R$_2$ =OMe; X =iodo
7h R$_3$ =H; R$_1$, R$_2$ =OMe; X =iodo
7i R$_1$, R$_2$, R$_3$ =OMe; X =iodo
7j R$_1$, R$_3$ =H; R$_2$ =OMe; X =nitro
7k R$_3$ =H; R$_1$, R$_2$ =OMe; X =nitro
7l R$_1$, R$_2$, R$_3$ =OMe; X =nitro Scheme 1

FIG. 1

Scheme 2

DIARYL ETHER LINKED PYRROLO [2,1-C][1,4] BENZODIAZEPINE HYBRIDS AND PROCESS FOR THE PREPARATION THEREOF

CROSS-REFERENCE TO RELATED APPLICATIONS

This application is the national phase under 35 U.S.C. §371 of prior PCT International Application No. PCT/IB2011/000670 which has an International Filing Date of Mar. 30, 2011, which designates the United States of America, and which claims priority to Indian Application No. IN 0390/DEL/2011 filed Feb. 15, 2011, the disclosures of which are hereby expressly incorporated by reference in their entirety and are hereby expressly made a portion of this application.

FIELD OF THE INVENTION

The present invention relates to diaryl ether linked pyrrolo[2,1-c][1,4]benzodiazepine hybrids of general formula A useful as anticancer agents.

GENERAL FORMULA A

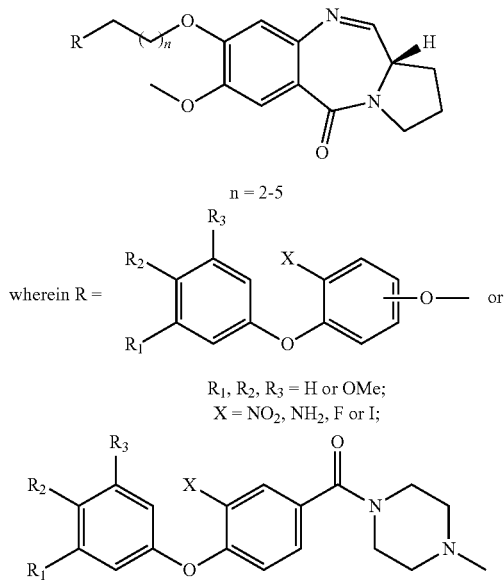

wherein R =

$R_1, R_2, R_3$ = H or OMe;
X = $NO_2$, $NH_2$, F or I;

Present invention further relates to process for the preparation of diaryl ether linked pyrrolo[2,1-c][1,4]benzodiazepine hybrids of general formula A.

More particularly, the present invention relates to 7-methoxy(8-3-[3/4-amino, nitro, fluoro,iodo-3/4-(mono,di,tri-methoxyphenoxy)phenoxy]alkoxy)-(11aS)-1,2,3,11a-tetrahydro-5H-pyrrolo[2,1-c][1,4]benzodiazepin-5-one and 7-methoxy-(8-(3-4-[3-amino,nitro,fluoro,iodo-4-(mono,di,tri-methoxyphenoxy)benzoyl]piperazinoalkoxy)-(11aS)-1,2,3,11a-tetrahydro-5H-pyrrolo[2,1-c][1,4]benzodiazepin-5-one with aliphatic chain length variations useful as anticancer (antitumour) agents.

The structural formulae of the representative compounds of diaryl ether linked pyrrolo[2,1-c][1,4]benzodiazepine hybrids of formula 10(a-h) to 21(a-h) and 22(a-d) to 33(a-d) are:

Formula 10a-h to 21a-h

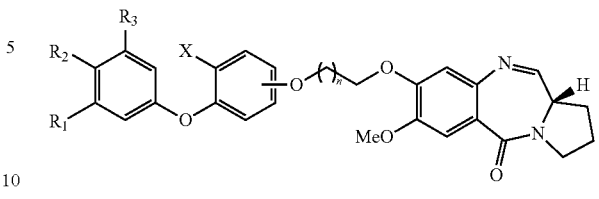

n = 2-5
$R_1, R_2, R_3$ = H, OMe;
X = $NO_2$, $NH_2$, F, I;

Formula 22a-d to 33a-d

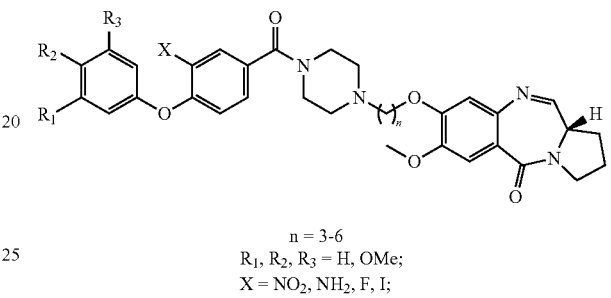

n = 3-6
$R_1, R_2, R_3$ = H, OMe;
X = $NO_2$, $NH_2$, F, I;

BACKGROUND OF THE INVENTION

Pyrrolo[2,1-c][1,4]benzodiazepine antitumour antibiotics are commonly known as anthramycin class of compounds. In the last few years, a growing interest has been shown in the development of new pyrrolo[2,1-c][1,4]benzodiazepines (PBDs). These antibiotics react covalently with DNA to form an N2-guanine adduct that lies within the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; Unezawa, H. *J. Antibiot.*, 1980, 33, 665.; Kohn, K. W. and Speous, C. L. *J. Mol. Biol.*, 1970, 51, 551.; Hurley, L. H.; Gairpla, C. and Zmijewski, M. Biochem. *Biophys. Acta.*, 1977, 475, 521.; Kaplan, D. J. and Hurley, L. H. *Biochemistry*, 1981, 20, 7572). The molecules have a right-handed twist, which allows them to follow the curvature of the minor groove of B-form double-stranded DNA spanning three base pairs. A recent development has been the linking of two PBD units through their C-8 positions to give bisfunctional-alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S, and Hurley, L. H. *J. Org. Chem.* 1996, 61, 8141).

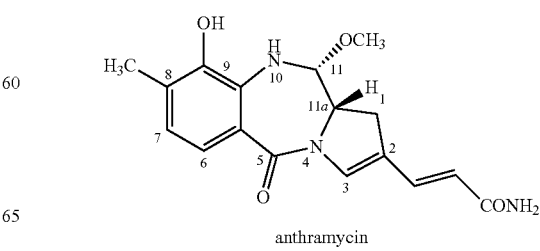

anthramycin

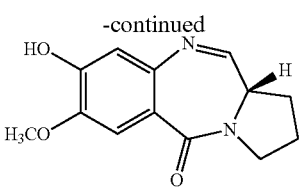

DC-81

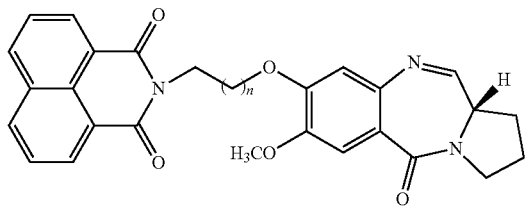

DC-81 dimers (n = 3-5); DSB-120 (n = 3)

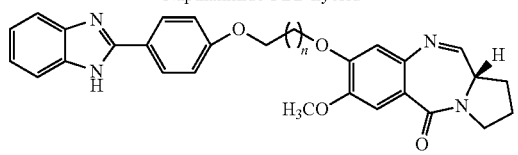

n = 1-9
Benzothiazole-PBD hybrid

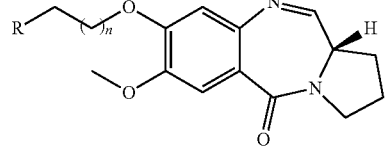

n = 1-9
Napthalimide-PBD hybrid

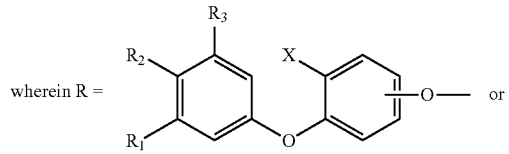

n = 1-9
Benzimidazole-PBD hybrid

Recently, PBD dimers have been developed that comprise of two C2-exo-methylene substituted DC-81 subunits tethered through their C-8 position via an inert propanedioxy linker (Gregson, S. J.; Howard, P. W.; Hartely, J. A.; Brooks, N. A.; Adams, L. J.; Jenkins, T. C.; Kelland, L. R. and Thurston, D. E. *J. Med. Chem.* 2001, 44, 737). A non-cross-linking mixed imine-amide PBD dimers have been synthesized that have significant DNA binding ability and potent antitumour activity (Kamal, A.; Ramesh, G. Laxman, N.; Ramulu, P.; Srinivas, O.; Neelima, K.; Kondapi, A. K.; Srinu, V. B.; Nagarajaram, H. M. *J. Med. Chem.* 2002, 45, 4679). Recently, some new pyrrolobenzodiazepine (PBD) hybrids have been synthesized that have significant DNA binding ability and potent antitumour activity (Kamal, A.; Srinivas, O.; Ramulu, P.; Ramesh, G.; Kumar, P. P. *Bioorg. Med. Chem. Lett.* 2003, 13, 3577).

Naturally occurring pyrrolo[2,1-c][1,4]benzodiazepines belong to a group of antitumour antibiotics derived from Streptomyces species. Recently, there is much impetus for the PBD systems as they can recognize and bind to specific sequence of DNA. Examples of naturally occurring PBDs include anthramycin, DC-81, tomaymycin, sibiromycin and neothramycin.

However, the clinical efficacy for these antibiotics is hindered by several limitations, such as poor water solubility, cardio toxicity, development of drug resistance and metabolic inactivation.

OBJECTIVES OF THE INVENTION

The main objective of the present invention is to provide diaryl ether linked pyrrolo[2,1-c][1,4]benzodiazepine hybrids of general formula A, useful as anticancer agents.

Another objective of the present invention is to provide a process for the preparation of diaryl ether linked pyrrolo[2,1-c][1,4]benzodiazepine hybrids.

SUMMARY OF THE INVENTION

The present invention provides diaryl ether linked pyrrolo [2,1-c][1,4]benzodiazepine hybrids of general formula A

GENERAL FORMULA A

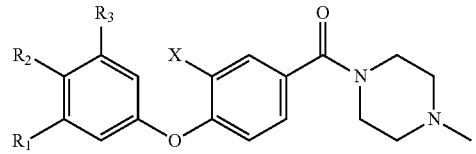

n = 2-5 wherein R =

$R_1, R_2, R_3$ = H or OMe;
X = $NO_2$, $NH_2$, F or I.

Further, the present invention provide a process for the preparation of diaryl ether linked pyrrolo[2,1-c][1,4]benzodiazepine hybrids.

BRIEF DESCRIPTION OF THE DRAWINGS

FIG. 1-Scheme 1 represents flow diagram for the preparation of compounds of formulae 3(a-d), 5(a-x) and 7(a-l).

DETAILED DESCRIPTION OF THE INVENTION

Figure 2:
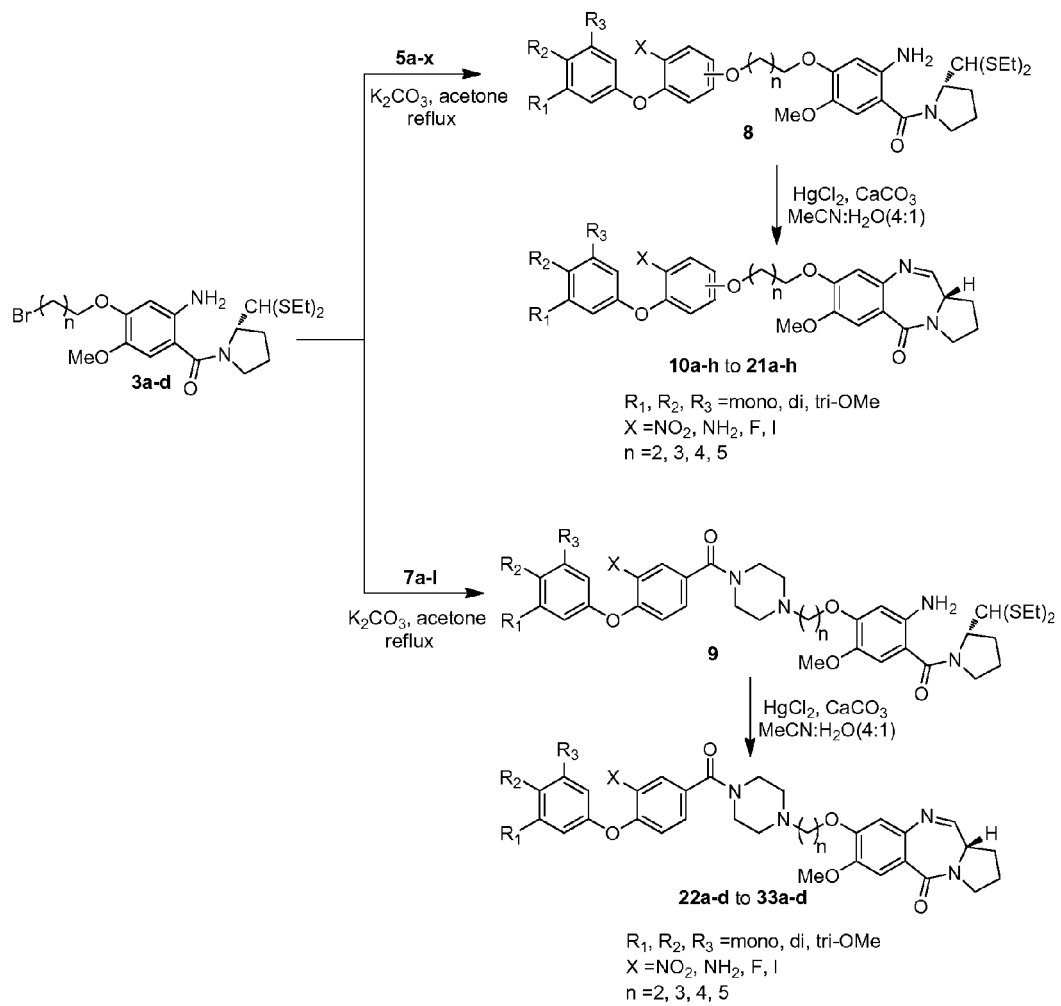
FIG. 2-Scheme 2 represents flow diagram for the preparation of compounds of formulae 10(a-h) to 21(a-h) and 22(a-d) to 33(a-d)

Accordingly, the present invention provides pyrrolo[2,1-c][1,4]benzodiazepine linked diaryl ether conjugates of general formula A

GENERAL FORMULA A

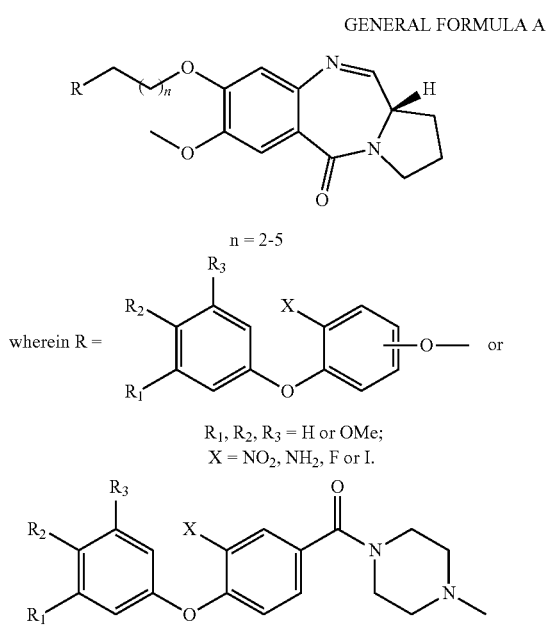

n = 2-5
wherein R =
R₁, R₂, R₃ = H or OMe;
X = NO₂, NH₂, F or I.

In an embodiment of present invention, representative compounds of general formulae 10(a-h) to 21(a-h) and 22(a-d) to 33(a-d) of diaryl ether linked pyrrolo[2,1-c][1,4]benzodiazepine hybrids of formula A are:

Formula 10a-h to 21a-h

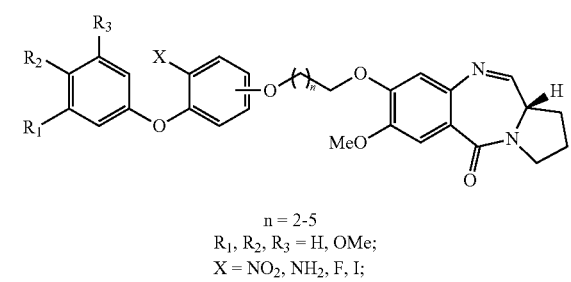

n = 2-5
R₁, R₂, R₃ = H, OMe;
X = NO₂, NH₂, F, I;

Formula 22a-d to 33a-d

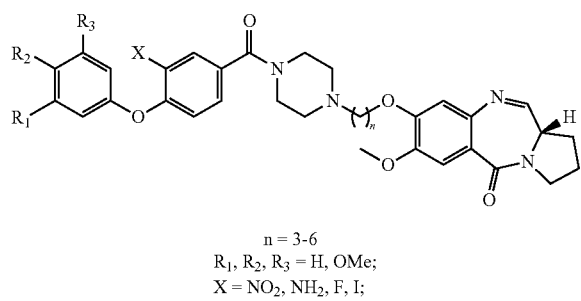

n = 3-6
R₁, R₂, R₃ = H, OMe;
X = NO₂, NH₂, F, I;

In yet another embodiment of the present invention, chemical formula of the diaryl ether linked pyrrolo[2,1-c][1,4] benzo diazepine hybrids of general formula A are:

7-Methoxy-(8-3-[3-amino-4-(4-methoxyphenoxy)phenoxy]propoxy)-(11aS)-1,2,3,11a-tetrahydro-5H-pyrrolo[2,1-c][1,4]benzodiazepin-5-one (10a);

7-Methoxy-(8-4-[3-amino-4-(4-methoxyphenoxy)phenoxy]butoxy)-(11aS)-1,2,3,11a-tetrahydro-5H-pyrrolo[2,1-c][1,4]benzodiazepin-5-one (10b);

7-Methoxy-(8-(5-[3-amino-4-(4-methoxyphenoxy)phenoxy]pentyloxy)-(11aS)-1,2,3,11a-tetrahydro-5H-pyrrolo[2,1-c][1,4]benzodiazepin-5-one (10c);

7-Methoxy-(8-(6-[3-amino-4-(4-methoxyphenoxy)phenoxy]hexyloxy)-(11aS)-1,2,3,11a-tetrahydro-5H-pyrrolo[2,1-c][1,4]benzodiazepin-5-one (10d);

7-Methoxy-(8-3-[4-amino-3-(4-methoxyphenoxy)phenoxy]propoxy)-(11aS)-1,2,3,11a-tetrahydro-5H-pyrrolo[2,1-c][1,4]benzodiazepin-5-one (10e);

7-Methoxy-(8-4-[4-amino-3-(4-methoxyphenoxy)phenoxy]butoxy)-(11aS)-1,2,3,11a-tetrahydro-5H-pyrrolo[2,1-c][1,4]benzodiazepin-5-one (10f);

7-Methoxy-(8-5-[4-amino-3-(4-methoxyphenoxy)phenoxy]pentyloxy)-(11aS)-1,2,3,11a-tetrahydro-5H-pyrrolo[2,1-c][1,4]benzodiazepin-5-one (10g);

7-Methoxy-(8-6-[4-amino-3-(4-methoxyphenoxy)phenoxy]hexyloxy)-(11aS)-1,2,3,11a-tetrahydro-5H-pyrrolo[2,1-c][1,4]benzodiazepin-5-one (10h);

7-Methoxy-(8-3-[3-amino-4-(3,4-dimethoxyphenoxy)phenoxy]propoxy)-(11aS)-1,2,3,11a-tetrahydro-5H-pyrrolo[2,1-c][1,4]benzodiazepin-5-one (11a);

7-Methoxy-(8-4-[3-amino-4-(3,4-dimethoxyphenoxy)phenoxy]butoxy)-(11aS)-1,2,3,11a-tetrahydro-5H-pyrrolo[2,1-c][1,4]benzodiazepin-5-one (11b);

7-Methoxy-(8-(5-[3-amino-4-(3,4-dimethoxyphenoxy)phenoxy]pentyloxy)-(11aS)-1,2,3,11a-tetrahydro-5H-pyrrolo[2,1-c][1,4]benzodiazepin-5-one (11c);

7-Methoxy-(8-(6-[3-amino-4-(3,4-dimethoxyphenoxy)phenoxy]hexyloxy)-(11aS)-1,2,3,11a-tetrahydro-5H-pyrrolo[2,1-c][1,4]benzodiazepin-5-one (11d);

7-Methoxy-(8-3-[4-amino-3-(3,4-dimethoxyphenoxy)phenoxy]propoxy)-(11aS)-1,2,3,11a-tetrahydro-5H-pyrrolo[2,1-c][1,4]benzodiazepin-5-one (11e);

7-Methoxy-(8-4-[4-amino-3-(3,4-dimethoxyphenoxy)phenoxy]butoxy)-(11aS)-1,2,3,11a-tetrahydro-5H-pyrrolo[2,1-c][1,4]benzodiazepin-5-one (11f);

7-Methoxy-(8-5-[4-amino-3-(3,4-dimethoxyphenoxy)phenoxy]pentyloxy)-(11aS)-1,2,3,11a-tetrahydro-5H-pyrrolo[2,1-c][1,4]benzodiazepin-5-one (11g);

7-Methoxy-(8-6-[4-amino-3-(3,4-dimethoxyphenoxy)phenoxy]hexyloxy)-(11aS)-1,2,3,11a-tetrahydro-5H-pyrrolo[2,1-c][1,4]benzodiazepin-5-one (11h);

7-Methoxy-(8-3-[3-amino-4-(3,4,5-trimethoxyphenoxy)phenoxy]propoxy)-(11aS)-1,2,3,11a-tetrahydro-5H-pyrrolo[2,1-c][1,4]benzodiazepin-5-one (12a);

7-Methoxy-(8-4-[3-amino-4-(3,4,5-trimethoxyphenoxy)phenoxy]butoxy)-(11aS)-1,2,3,11a-tetrahydro-5H-pyrrolo[2,1-c][1,4]benzodiazepin-5-one (12b);

7-Methoxy-(8-(5-[3-amino-4-(3,4,5-trimethoxyphenoxy)phenoxy]pentyloxy)-(11aS)-1,2,3,11a-tetrahydro-5H-pyrrolo[2,1-c][1,4]benzodiazepin-5-one (12c);

7-Methoxy-(8-(6-[3-amino-4-(3,4,5-trimethoxyphenoxy)phenoxy]hexyloxy)-(11aS)-1,2,3,11a-tetrahydro-5H-pyrrolo[2,1-c][1,4]benzodiazepin-5-one (12d);

7-Methoxy-(8-3-[4-amino-3-(3,4,5-trimethoxyphenoxy)phenoxy]propoxy)-(11aS)-1,2,3,11a-tetrahydro-5H-pyrrolo[2,1-c][1,4]benzodiazepin-5-one (12e);

7-Methoxy-(8-4-[4-amino-3-(3,4,5-trimethoxyphenoxy)phenoxy]butoxy)-(11aS)-1,2,3,11a-tetrahydro-5H-pyrrolo[2,1-c][1,4]benzodiazepin-5-one (12f);

7-Methoxy-(8-5-[4-amino-3-(3,4,5-trimethoxyphenoxy)phenoxy]pentyloxy)-(11aS)-1,2,3,11a-tetrahydro-5H-pyrrolo[2,1-c][1,4]benzodiazepin-5-one (12g);

7-Methoxy-(8-6-[4-amino-3-(3,4,5-trimethoxyphenoxy)phenoxy]hexyloxy)-(11aS)-1,2,3,11a-tetrahydro-5H-pyrrolo[2,1-c][1,4]benzodiazepin-5-one (12h);

7-Methoxy-(8-3-[3-fluoro-4-(4-methoxyphenoxy)phenoxy]propoxy)-(11aS)-1,2,3,11a-tetrahydro-5H-pyrrolo[2,1-c][1,4]benzodiazepin-5-one (13a);

7-Methoxy-(8-4-[3-fluoro-4-(4-methoxyphenoxy)phenoxy]butoxy)-(11aS)-1,2,3,11a-tetrahydro-5H-pyrrolo[2,1-c][1,4]benzodiazepin-5-one (13b);

7-Methoxy-(8-(5-[3-fluoro-4-(4-methoxyphenoxy)phenoxy]pentyloxy)-(11aS)-1,2,3,11a-tetrahydro-5H-pyrrolo[2,1-c][1,4]benzodiazepin-5-one (13c);

7-Methoxy-(8-(6-[3-fluoro-4-(4-methoxyphenoxy)phenoxy]hexyloxy)-(11aS)-1,2,3,11a-tetrahydro-5H-pyrrolo[2,1-c][1,4]benzodiazepin-5-one (13d);

7-Methoxy-(8-3-[4-fluoro-3-(4-methoxyphenoxy)phenoxy]propoxy)-(11aS)-1,2,3,11a-tetrahydro-5H-pyrrolo[2,1-c][1,4]benzodiazepin-5-one (13e);

7-Methoxy-(8-4-[4-fluoro-3-(4-methoxyphenoxy)phenoxy]butoxy)-(11aS)-1,2,3,11a-tetrahydro-5H-pyrrolo[2,1-c][1,4]benzodiazepin-5-one (13f);

7-Methoxy-(8-5-[4-fluoro-3-(4-methoxyphenoxy)phenoxy]pentyloxy)-(11aS)-1,2,3,11a-tetrahydro-5H-pyrrolo[2,1-c][1,4]benzodiazepin-5-one (13g);

7-Methoxy-(8-6-[4-fluoro-3-(4-methoxyphenoxy)phenoxy]hexyloxy)-(11aS)-1,2,3,11a-tetrahydro-5H-pyrrolo[2,1-c][1,4]benzodiazepin-5-one (13h);

7-Methoxy-(8-3-[3-fluoro-4-(3,4-dimethoxyphenoxy)phenoxy]propoxy)-(11aS)-1,2,3,11a-tetrahydro-5H-pyrrolo[2,1-c][1,4]benzodiazepin-5-one (14a);

7-Methoxy-(8-4-[3-fluoro-4-(3,4-dimethoxyphenoxy)phenoxy]butoxy)-(11aS)-1,2,3,11a-tetrahydro-5H-pyrrolo[2,1-c][1,4]benzodiazepin-5-one (14b);

7-Methoxy-(8-(5-[3-fluoro-4-(3,4-dimethoxyphenoxy)phenoxy]pentyloxy)-(11aS)-1,2,3,11a-tetrahydro-5H-pyrrolo[2,1-c][1,4]benzodiazepin-5-one (14c);

7-Methoxy-(8-(6-[3-fluoro-4-(3,4-dimethoxyphenoxy)phenoxy]hexyloxy)-(11aS)-1,2,3,11a-tetrahydro-5H-pyrrolo[2,1-c][1,4]benzodiazepin-5-one (14d);

7-Methoxy-(8-3-[4-fluoro-3-(3,4-dimethoxyphenoxy)phenoxy]propoxy)-(11aS)-1,2,3,11a-tetrahydro-5H-pyrrolo[2,1-c][1,4]benzodiazepin-5-one (14e);

7-Methoxy-(8-4-[4-fluoro-3-(3,4-dimethoxyphenoxy)phenoxy]butoxy)-(11aS)-1,2,3,11a-tetrahydro-5H-pyrrolo[2,1-c][1,4]benzodiazepin-5-one (14f);

7-Methoxy-(8-5-[4-fluoro-3-(3,4-dimethoxyphenoxy)phenoxy]pentyloxy)-(11aS)-1,2,3,11a-tetrahydro-5H-pyrrolo[2,1-c][1,4]benzodiazepin-5-one (14g);

7-Methoxy-(8-6-[4-fluoro-3-(3,4-dimethoxyphenoxy)phenoxy]hexyloxy)-(11aS)-1,2,3,11a-tetrahydro-5H-pyrrolo[2,1-c][1,4]benzodiazepin-5-one (14h);

7-Methoxy-(8-3-[3-fluoro-4-(3,4,5-trimethoxyphenoxy)phenoxy]propoxy)-(11aS)-1,2,3,11a-tetrahydro-5H-pyrrolo[2,1-c][1,4]benzodiazepin-5-one (15a);

7-Methoxy-(8-4-[3-fluoro-4-(3,4,5-trimethoxyphenoxy)phenoxy]butoxy)-(11aS)-1,2,3,11a-tetrahydro-5H-pyrrolo[2,1-c][1,4]benzodiazepin-5-one (15b);

7-Methoxy-(8-(5-[3-fluoro-4-(3,4,5-trimethoxyphenoxy)phenoxy]pentyloxy)-(11aS)-1,2,3,11a-tetrahydro-5H-pyrrolo[2,1-c][1,4]benzodiazepin-5-one (15c);

7-Methoxy-(8-(6-[3-fluoro-4-(3,4,5-trimethoxyphenoxy)phenoxy]hexyloxy)-(11aS)-1,2,3,11a-tetrahydro-5H-pyrrolo[2,1-c][1,4]benzodiazepin-5-one (15d);

7-Methoxy-(8-3-[4-fluoro-3-(3,4,5-trimethoxyphenoxy)phenoxy]propoxy)-(11aS)-1,2,3,11a-tetrahydro-5H-pyrrolo[2,1-c][1,4]benzodiazepin-5-one (15e);

7-Methoxy-(8-4-[4-fluoro-3-(3,4,5-trimethoxyphenoxy)phenoxy]butoxy)-(11aS)-1,2,3,11a-tetrahydro-5H-pyrrolo[2,1-c][1,4]benzodiazepin-5-one (15f);

7-Methoxy-(8-5-[4-fluoro-3-(3,4,5-trimethoxyphenoxy)phenoxy]pentyloxy)-(11aS)-1,2,3,11a-tetrahydro-5H-pyrrolo[2,1-c][1,4]benzodiazepin-5-one (15g);

7-Methoxy-(8-6-[4-fluoro-3-(3,4,5-trimethoxyphenoxy)phenoxy]hexyloxy)-(11aS)-1,2,3,11a-tetrahydro-5H-pyrrolo[2,1-c][1,4]benzodiazepin-5-one (15h);

7-Methoxy-(8-3-[3-iodo-4-(4-methoxyphenoxy)phenoxy]propoxy)-(11aS)-1,2,3,11a-tetrahydro-5H-pyrrolo[2,1-c][1,4]benzodiazepin-5-one (16a);

7-Methoxy-(8-4-[3-iodo-4-(4-methoxyphenoxy)phenoxy]butoxy)-(11aS)-1,2,3,11a-tetrahydro-5H-pyrrolo[2,1-c][1,4]benzodiazepin-5-one (16b);

7-Methoxy-(8-(5-[3-iodo-4-(4-methoxyphenoxy)phenoxy]pentyloxy)-(11aS)-1,2,3,11a-tetrahydro-5H-pyrrolo[2,1-c][1,4]benzodiazepin-5-one (16c)

7-Methoxy-(8-(6-[3-iodo-4-(4-methoxyphenoxy)phenoxy]hexyloxy)-(11aS)-1,2,3,11a-tetrahydro-5H-pyrrolo[2,1-c][1,4]benzodiazepin-5-one (16d);

7-Methoxy-(8-3-[4-iodo-3-(4-methoxyphenoxy)phenoxy]propoxy)-(11aS)-1,2,3,11a-tetrahydro-5H-pyrrolo[2,1-c][1,4]benzodiazepin-5-one (16e);

7-Methoxy-(8-4-[4-iodo-3-(4-methoxyphenoxy)phenoxy]butoxy)-(11aS)-1,2,3,11a-tetrahydro-5H-pyrrolo[2,1-c][1,4]benzodiazepin-5-one (16f);

7-Methoxy-(8-5-[4-iodo-3-(4-methoxyphenoxy)phenoxy]pentyloxy)-(11aS)-1,2,3,11a-tetrahydro-5H-pyrrolo[2,1-c][1,4]benzodiazepin-5-one (16g);

7-Methoxy-(8-6-[4-iodo-3-(4-methoxyphenoxy)phenoxy]hexyloxy)-(11aS)-1,2,3,11a-tetrahydro-5H-pyrrolo[2,1-c][1,4]benzodiazepin-5-one (16h);

7-Methoxy-(8-3-[3-iodo-4-(3,4-dimethoxyphenoxy)phenoxy]propoxy)-(11aS)-1,2,3,11a-tetrahydro-5H-pyrrolo[2,1-c][1,4]benzodiazepin-5-one (17a);

7-Methoxy-(8-4-[3-iodo-4-(3,4-dimethoxyphenoxy)phenoxy]butoxy)-(11aS)-1,2,3,11a-tetrahydro-5H-pyrrolo[2,1-c][1,4]benzodiazepin-5-one (17b);

7-Methoxy-(8-(5-[3-iodo-4-(3,4-dimethoxyphenoxy)phenoxy]pentyloxy)-(11aS)-1,2,3,11a-tetrahydro-5H-pyrrolo[2,1-c][1,4]benzodiazepin-5-one (17c);

7-Methoxy-(8-(6-[3-iodo-4-(3,4-dimethoxyphenoxy)phenoxy]hexyloxy)-(11aS)-1,2,3,11a-tetrahydro-5H-pyrrolo[2,1-c][1,4]benzodiazepin-5-one (17d);

7-Methoxy-(8-3-[4-iodo-3-(3,4-dimethoxyphenoxy)phenoxy]propoxy)-(11aS)-1,2,3,11a-tetrahydro-5H-pyrrolo[2,1-c][1,4]benzodiazepin-5-one (17e);

7-Methoxy-(8-4-[4-iodo-3-(3,4-dimethoxyphenoxy)phenoxy]butoxy)-(11aS)-1,2,3,11a-tetrahydro-5H-pyrrolo[2,1-c][1,4]benzodiazepin-5-one (17f; 7-Methoxy-(8-5-[4-iodo-3-(3,4-dimethoxyphenoxy)phenoxy]pentyloxy)-(11aS)-1,2,3,11a-tetrahydro-5H-pyrrolo[2,1-c][1,4]benzodiazepin-5-one (17g);

7-Methoxy-(8-6-[4-iodo-3-(3,4-dimethoxyphenoxy)phenoxy]hexyloxy)-(11aS)-1,2,3,11a-tetrahydro-5H-pyrrolo[2,1-c][1,4]benzodiazepin-5-one (17h);

7-Methoxy-(8-3-[3-iodo-4-(3,4,5-trimethoxyphenoxy)phenoxy]propoxy)-(11aS)-1,2,3,11a-tetrahydro-5H-pyrrolo[2,1-c][1,4]benzodiazepin-5-one (18a);

7-Methoxy-(8-4-[3-iodo-4-(3,4,5-trimethoxyphenoxy)phenoxy]butoxy)-(11aS)-1,2,3,11a-tetrahydro-5H-pyrrolo[2,1-c][1,4]benzodiazepin-5-one (18b);

7-Methoxy-(8-(5-[3-iodo-4-(3,4,5-trimethoxyphenoxy)phenoxy]pentyloxy)-(11aS)-1,2,3,11a-tetrahydro-5H-pyrrolo[2,1-c][1,4]benzodiazepin-5-one (18c);

7-Methoxy-(8-(6-[3-iodo-4-(3,4,5-trimethoxyphenoxy)phenoxy]hexyloxy)-(11aS)-1,2,3,11a-tetrahydro-5H-pyrrolo[2,1-c][1,4]benzodiazepin-5-one (18d);

7-Methoxy-(8-3-[4-iodo-3-(3,4,5-trimethoxyphenoxy)phenoxy]propoxy)-(11aS)-1,2,3,11a-tetrahydro-5H-pyrrolo[2,1-c][1,4]benzodiazepin-5-one (18e);

7-Methoxy-(8-4-[4-iodo-3-(3,4,5-trimethoxyphenoxy)phenoxy]butoxy)-(11aS)-1,2,3,11a-tetrahydro-5H-pyrrolo[2,1-c][1,4]benzodiazepin-5-one (180; 7-Methoxy-(8-5-[4-iodo-3-(3,4,5-trimethoxyphenoxy)phenoxy]pentyloxy)-(11aS)-1,2,3,11a-tetrahydro-5H-pyrrolo[2,1-c][1,4]benzodiazepin-5-one (18g);

7-Methoxy-(8-6-[4-iodo-3-(3,4,5-trimethoxyphenoxy)phenoxy]hexyloxy)-(11aS)-1,2,3,11a-tetrahydro-5H-pyrrolo[2,1-c][1,4]benzodiazepin-5-one (18h);

7-Methoxy-(8-3-[4-(4-methoxyphenoxy)-3-nitrophenoxy]propoxy)-(11aS)-1,2,3,11a-tetrahydro-5H-pyrrolo[2,1-c][1,4]benzodiazepin-5-one (19a);

7-Methoxy-(8-3-[4-(4-methoxyphenoxy)-3-nitrophenoxy]butoxy)-(11aS)-1,2,3,11a-tetrahydro-5H-pyrrolo[2,1-c][1,4]benzodiazepin-5-one (19b);

7-Methoxy-(8-3-[4-(4-methoxyphenoxy)-3-nitrophenoxy]pentyloxy)-(11aS)-1,2,3,11a-tetrahydro-5H-pyrrolo[2,1-c][1,4]benzodiazepin-5-one (19c);

7-Methoxy-(8-3-[4-(4-methoxyphenoxy)-3-nitrophenoxy]hexyloxy)-(11aS)-1,2,3,11a-tetrahydro-5H-pyrrolo[2,1-c][1,4]benzodiazepin-5-one (19d);

7-Methoxy-(8-3-[3-(4-methoxyphenoxy)-2-nitrophenoxy]propoxy)-(11aS)-1,2,3,11a-tetrahydro-5H-pyrrolo[2,1-c][1,4]benzodiazepin-5-one (19e);

7-Methoxy-(8-3-[3-(4-methoxyphenoxy)-2-nitrophenoxy]butoxy)-(11aS)-1,2,3,11a-tetrahydro-5H-pyrrolo[2,1-c][1,4]benzodiazepin-5-one (190; 7-Methoxy-(8-3-[3-(4-methoxyphenoxy)-2-nitrophenoxy]pentyloxy)-(11aS)-1,2,3,11a-tetrahydro-5H-pyrrolo[2,1-c][1,4]benzodiazepin-5-one (19g);

7-Methoxy-(8-3-[3-(4-methoxyphenoxy)-2-nitrophenoxy]hexyloxy)-(11aS)-1,2,3,11a-tetrahydro-5H-pyrrolo[2,1-c][1,4]benzodiazepin-5-one (19h);

7-Methoxy-(8-3-[4-(3,4-dimethoxyphenoxy)-3-nitrophenoxy]propoxy)-(11aS)-1,2,3,11a-tetrahydro-5H-pyrrolo[2,1-c][1,4]benzodiazepin-5-one (20a);

7-Methoxy-(8-3-[4-(3,4-dimethoxyphenoxy)-3-nitrophenoxy]butoxy)-(11aS)-1,2,3,11a-tetrahydro-5H-pyrrolo[2,1-c][1,4]benzodiazepin-5-one (20b);

7-Methoxy-(8-3-[4-(3,4-dimethoxyphenoxy)-3-nitrophenoxy]pentyloxy)-(11aS)-1,2,3,11a-tetrahydro-5H-pyrrolo[2,1-c][1,4]benzodiazepin-5-one (20c);

7-Methoxy-(8-3-[4-(3,4-dimethoxyphenoxy)-3-nitrophenoxy]hexyloxy)-(11aS)-1,2,3,11a-tetrahydro-5H-pyrrolo[2,1-c][1,4]benzodiazepin-5-one (20d);

7-Methoxy-(8-3-[3-(3,4-dimethoxyphenoxy)-2-nitrophenoxy]propoxy)-(11aS)-1,2,3,11a-tetrahydro-5H-pyrrolo[2,1-c][1,4]benzodiazepin-5-one (20e);

7-Methoxy-(8-3-[3-(3,4-dimethoxyphenoxy)-2-nitrophenoxy]butoxy)-(11aS)-1,2,3,11a-tetrahydro-5H-pyrrolo[2,1-c][1,4]benzodiazepin-5-one (200; 7-Methoxy-(8-3-[3-(3,4-dimethoxyphenoxy)-2-nitrophenoxy]pentyloxy)-(11aS)-1,2,3,11a-tetrahydro-5H-pyrrolo[2,1-c][1,4]benzodiazepin-5-one (20g);

7-Methoxy-(8-3-[3-(3,4-dimethoxyphenoxy)-2-nitrophenoxy]hexyloxy)-(11aS)-1,2,3,11a-tetrahydro-5H-pyrrolo[2,1-c][1,4]benzodiazepin-5-one (20h);

7-Methoxy-(8-3-[4-(3,4,5-trimethoxyphenoxy)-3-nitrophenoxy]propoxy)-(11aS)-1,2,3,11a-tetrahydro-5H-pyrrolo[2,1-c][1,4]benzodiazepin-5-one (21a);

7-Methoxy-(8-3-[4-(3,4,5-trimethoxyphenoxy)-3-nitrophenoxy]butoxy)-(11aS)-1,2,3,11a-tetrahydro-5H-pyrrolo[2,1-c][1,4]benzodiazepin-5-one (21b);

7-Methoxy-(8-3-[4-(3,4,5-timethoxyphenoxy)-3-nitrophenoxy]pentyloxy)-(11aS)-1,2,3,11a-tetrahydro-5H-pyrrolo[2,1-c][1,4]benzodiazepin-5-one (21c);

7-Methoxy-(8-3-[4-(3,4,5-trimethoxyphenoxy)-3-nitrophenoxy]hexyloxy)-(11aS)-1,2,3,11a-tetrahydro-5H-pyrrolo[2,1-c][1,4]benzodiazepin-5-one (21d);

7-Methoxy-(8-3-[3-(3,4,5-trimethoxyphenoxy)-2-nitrophenoxy]propoxy)-(11aS)-1,2,3,11a-tetrahydro-5H-pyrrolo[2,1-c][1,4]benzodiazepin-5-one (21e);

7-Methoxy-(8-3-[3-(3,4,5-trimethoxyphenoxy)-2-nitrophenoxy]butoxy)-(11aS)-1,2,3,11a-tetrahydro-5H-pyrrolo[2,1-c][1,4]benzodiazepin-5-one (210; 7-Methoxy-(8-3-[3-(3,4,5-trimethoxyphenoxy)-2-nitrophenoxy]pentyloxy)-(11aS)-1,2,3,11a-tetrahydro-5H-pyrrolo[2,1-c][1,4]benzodiazepin-5-one (21g);

7-Methoxy-(8-3-[3-(3,4,5-trimethoxyphenoxy)-2-nitrophenoxy]hexyloxy)-(11aS)-1,2,3,11a-tetrahydro-5H-pyrrolo[2,1-c][1,4]benzodiazepin-5-one (21h);

7-Methoxy-(8-(3-4-[3-amino-4-(4-methoxyphenoxy)benzoyl]piperazinopropoxy)-(11aS)-1,2,3,11a-tetrahydro-5H-pyrrolo[2,1-c][1,4]benzodiazepin-5-one (22a);

7-Methoxy-(8-(3-4-[3-amino-4-(4-methoxyphenoxy)benzoyl]piperazinobutoxy)-(11aS)-1,2,3,11a-tetrahydro-5H-pyrrolo[2,1-c][1,4]benzodiazepin-5-one (22b);

7-Methoxy-(8-(3-4-[3-amino-4-(4-methoxyphenoxy)benzoyl]piperazinopentyloxy)-(11aS)-1,2,3,11a-tetrahydro-5H-pyrrolo[2,1-c][1,4]benzodiazepin-5-one (22c);

7-Methoxy-(8-(3-4-[3-amino-4-(4-methoxyphenoxy)benzoyl]piperazinohexyloxy)-(11aS)-1,2,3,11a-tetrahydro-5H-pyrrolo[2,1-c][1,4]benzodiazepin-5-one (22d);

7-Methoxy-(8-(3-4-[3-amino-4-(3,4-dimethoxyphenoxy)benzoyl]piperazinopropoxy)-(11aS)-1,2,3,11a-tetrahydro-5H-pyrrolo[2,1-c][1,4]benzodiazepin-5-one (23a);

7-Methoxy-(8-(3-4-[3-amino-4-(3,4-dimethoxyphenoxy)benzoyl]piperazinobutoxy)-(11aS)-1,2,3,11a-tetrahydro-5H-pyrrolo[2,1-c][1,4]benzodiazepin-5-one (23b);

7-Methoxy-(8-(3-4-[3-amino-4-(3,4-dimethoxyphenoxy)benzoyl]piperazinopentyloxy)-(11aS)-1,2,3,11a-tetrahydro-5H-pyrrolo[2,1-c][1,4]benzodiazepin-5-one (23c);

7-Methoxy-(8-(3-4-[3-amino-4-(3,4-dimethoxyphenoxy)benzoyl]piperazinohexyloxy)-(11aS)-1,2,3,11a-tetrahydro-5H-pyrrolo[2,1-c][1,4]benzodiazepin-5-one (23d);

7-Methoxy-(8-(3-4-[3-amino-4-(3,4,5-trimethoxyphenoxy)benzoyl]piperazinoprop oxy)-(11aS)-1,2,3,11a-tetrahydro-5H-pyrrolo[2,1-c][1,4]benzodiazepin-5-one (24a);

7-Methoxy-(8-(3-4-[3-amino-4-(3,4,5-trimethoxyphenoxy)benzoyl]piperazinobutoxy)-(11aS)-1,2,3,11a-tetrahydro-5H-pyrrolo[2,1-c][1,4]benzodiazepin-5-one (24b);

7-Methoxy-(8-(3-4-[3-amino-4-(3,4,5-trimethoxyphenoxy)benzoyl]piperazinopentyloxy)-(11aS)-1,2,3,11a-tetrahydro-5H-pyrrolo[2,1-c][1,4]benzodiazepin-5-one (24c);

7-Methoxy-(8-(3-4-[3-amino-4-(3,4,5-trimethoxyphenoxy)benzoyl]piperazinohexyloxy)-(11aS)-1,2,3,11a-tetrahydro-5H-pyrrolo[2,1-c][1,4]benzodiazepin-5-one (24d);

7-Methoxy-(8-(3-4-[3-fluoro-4-(4-methoxyphenoxy)benzoyl]piperazinopropoxy)-(11aS)-1,2,3,11a-tetrahydro-5H-pyrrolo[2,1-c][1,4]benzodiazepin-5-one (25a);

7-Methoxy-(8-(3-4-[3-fluoro-4-(4-methoxyphenoxy)benzoyl]piperazinobutoxy)-(11aS)-1,2,3,11a-tetrahydro-5H-pyrrolo[2,1-c][1,4]benzodiazepin-5-one (25b);

7-Methoxy-(8-(3-4-[3-fluoro-4-(4-methoxyphenoxy)benzoyl]piperazinopentyloxy)-(11aS)-1,2,3,11a-tetrahydro-5H-pyrrolo[2,1-c][1,4]benzodiazepin-5-one (25c);

7-Methoxy-(8-(3-4-[3-fluoro-4-(4-methoxyphenoxy)benzoyl]piperazinohexyloxy)-(11aS)-1,2,3,11a-tetrahydro-5H-pyrrolo[2,1-c][1,4]benzodiazepin-5-one (25d);

7-Methoxy-(8-(3-4-[3-fluoro-4-(3,4-dimethoxyphenoxy) benzoyl]piperazinopropoxy)-(11aS)-1,2,3,11a-tetrahydro-5H-pyrrolo[2,1-c][1,4]benzodiazepin-5-one (26a);

7-Methoxy-(8-(3-4-[3-fluoro-4-(3,4-dimethoxyphenoxy) benzoyl]piperazinobutoxy)-(11aS)-1,2,3,11a-tetrahydro-5H-pyrrolo[2,1-c][1,4]benzodiazepin-5-one (26b);

7-Methoxy-(8-(3-4-[3-fluoro-4-(3,4-dimethoxyphenoxy) benzoyl]piperazinopentyloxy)-(11aS)-1,2,3,11a-tetrahydro-5H-pyrrolo[2,1-c][1,4]benzodiazepin-5-one (26c);

7-Methoxy-(8-(3-4-[3-fluoro-4-(3,4-dimethoxyphenoxy) benzoyl]piperazinohexyloxy)-(11aS)-1,2,3,11a-tetrahydro-5H-pyrrolo[2,1-c][1,4]benzodiazepin-5-one (26d);

7-Methoxy-(8-(3-4-[3-fluoro-4-(3,4,5-trimethoxyphenoxy) benzoyl]piperazinoprop oxy)-(11aS)-1,2,3,11a-tetrahydro-5H-pyrrolo[2,1-c][1,4]benzodiazepin-5-one (27a);

7-Methoxy-(8-(3-4-[3-fluoro-4-(3,4,5-trimethoxyphenoxy) benzoyl]piperazinobut oxy)-(11aS)-1,2,3,11a-tetrahydro-5H-pyrrolo[2,1-c][1,4]benzodiazepin-5-one (27b);

7-Methoxy-(8-(3-4-[3-fluoro-4-(3,4,5-trimethoxyphenoxy) benzoyl]piperazinopentyloxy)-(11aS)-1,2,3,11a-tetrahydro-5H-pyrrolo[2,1-c][1,4]benzodiazepin-5-one (27c);

7-Methoxy-(8-(3-4-[3-fluoro-4-(3,4,5-trimethoxyphenoxy) benzoyl]piperazinohexyloxy)-(11aS)-1,2,3,11a-tetrahydro-5H-pyrrolo[2,1-c][1,4]benzodiazepin-5-one (27d);

7-Methoxy-(8-(3-4-[3-iodo-4-(4-methoxyphenoxy)benzoyl] piperazinopropoxy)-(11aS)-1,2,3,11a-tetrahydro-5H-pyrrolo[2,1-c][1,4]benzodiazepin-5-one (28a);

7-Methoxy-(8-(3-4-[3-iodo-4-(4-methoxyphenoxy)benzoyl] piperazinobutoxy)-(11aS)-1,2,3,11a-tetrahydro-5H-pyrrolo[2,1-c][1,4]benzodiazepin-5-one (28b);

7-Methoxy-(8-(3-4-[3-iodo-4-(4-methoxyphenoxy)benzoyl] piperazinopentyloxy)-(11aS)-1,2,3,11a-tetrahydro-5H-pyrrolo[2,1-c][1,4]benzodiazepin-5-one (28c);

7-Methoxy-(8-(3-4-[3-iodo-4-(4-methoxyphenoxy)benzoyl] piperazinohexyloxy)-(11aS)-1,2,3,11a-tetrahydro-5H-pyrrolo[2,1-c][1,4]benzodiazepin-5-one (28d);

7-Methoxy-(8-(3-4-[3-iodo-4-(3,4-dimethoxyphenoxy)benzoyl]piperazinopropoxy)-(11aS)-1,2,3,11a-tetrahydro-5H-pyrrolo[2,1-c][1,4]benzodiazepin-5-one (29a);

7-Methoxy-(8-(3-4-[3-iodo-4-(3,4-dimethoxyphenoxy)benzoyl]piperazinobutoxy)-(11aS)-1,2,3,11a-tetrahydro-5H-pyrrolo[2,1-c][1,4]benzodiazepin-5-one (29b);

7-Methoxy-(8-(3-4-[3-iodo-4-(3,4-dimethoxyphenoxy)benzoyl]piperazinopentyloxy)-(11aS)-1,2,3,11a-tetrahydro-5H-pyrrolo[2,1-c][1,4]benzodiazepin-5-one (29c);

7-Methoxy-(8-(3-4-[3-iodo-4-(3,4-dimethoxyphenoxy)benzoyl]piperazinohexyloxy)-(11aS)-1,2,3,11a-tetrahydro-5H-pyrrolo[2,1-c][1,4]benzodiazepin-5-one (29d);

7-Methoxy-(8-(3-4-[3-iodo-4-(3,4,5-trimethoxyphenoxy) benzoyl]piperazinoprop oxy)-(11aS)-1,2,3,11a-tetrahydro-5H-pyrrolo[2,1-c][1,4]benzodiazepin-5-one (30a);

7-Methoxy-(8-(3-4-[3-iodo-4-(3,4,5-trimethoxyphenoxy) benzoyl]piperazinobutoxy)-(11aS)-1,2,3,11a-tetrahydro-5H-pyrrolo[2,1-c][1,4]benzodiazepin-5-one (30b);

7-Methoxy-(8-(3-4-[3-iodo-4-(3,4,5-trimethoxyphenoxy) benzoyl]piperazino pentyloxy)-(11aS)-1,2,3,11a-tetrahydro-5H-pyrrolo[2,1-c][1,4]benzodiazepin-5-one (30c);

7-Methoxy-(8-(3-4-[3-iodo-4-(3,4,5-trimethoxyphenoxy) benzoyl]piperazinohexyloxy)-(11aS)-1,2,3,11a-tetrahydro-5H-pyrrolo[2,1-c][1,4]benzodiazepin-5-one (30d);

7-Methoxy-(8-(3-4-[4-(4-methoxyphenoxy)-3-nitrobenzoyl]piperazinopropoxy)-(11aS)-1,2,3,11a-tetrahydro-5H-pyrrolo[2,1-c][1,4]benzodiazepin-5-one (31a);

7-Methoxy-(8-(3-4-[4-(4-methoxyphenoxy)-3-nitrobenzoyl]piperazinobutoxy)-(11aS)-1,2,3,11a-tetrahydro-5H-pyrrolo[2,1-c][1,4]benzodiazepin-5-one (31b);

7-Methoxy-(8-(3-4-[4-(4-methoxyphenoxy)-3-nitrobenzoyl]piperazinopentyloxy)-(11aS)-1,2,3,11a-tetrahydro-5H-pyrrolo[2,1-c][1,4]benzodiazepin-5-one (31c);

7-Methoxy-(8-(3-4-[4-(4-methoxyphenoxy)-3-nitrobenzoyl]piperazinohexyloxy)-(11aS)-1,2,3,11a-tetrahydro-5H-pyrrolo[2,1-c][1,4]benzodiazepin-5-one (31d);

7-Methoxy-(8-(3-4-[4-(3,4-dimethoxyphenoxy)-3-nitrobenzoyl]piperazinopropoxy)-(11aS)-1,2,3,11a-tetrahydro-5H-pyrrolo[2,1-c][1,4]benzodiazepin-5-one (32a);

7-Methoxy-(8-(3-4-[4-(3,4-dimethoxyphenoxy)-3-nitrobenzoyl]piperazinobutoxy)-(11aS)-1,2,3,11a-tetrahydro-5H-pyrrolo[2,1-c][1,4]benzodiazepin-5-one (32b);

7-Methoxy-(8-(3-4-[4-(3,4-dimethoxyphenoxy)-3-nitrobenzoyl]piperazinopentyloxy)-(11aS)-1,2,3,11a-tetrahydro-5H-pyrrolo[2,1-c][1,4]benzodiazepin-5-one (32c);

7-Methoxy-(8-(3-4-[4-(3,4-dimethoxyphenoxy)-3-nitrobenzoyl]piperazinohexyloxy)-(11aS)-1,2,3,11a-tetrahydro-5H-pyrrolo[2,1-c][1,4]benzodiazepin-5-one (32d);

7-Methoxy-(8-(3-4-[4-(3,4,5-trimethoxyphenoxy)-3-nitrobenzoyl]piperazinopropoxy)-(11aS)-1,2,3,11a-tetrahydro-5H-pyrrolo[2,1-c][1,4]benzodiazepin-5-one (33a);

7-Methoxy-(8-(3-4-[4-(3,4,5-trimethoxyphenoxy)-3-nitrobenzoyl]piperazinbutoxy)-(11aS)-1,2,3,11a-tetrahydro-5H-pyrrolo[2,1-c][1,4]benzodiazepin-5-one (33b);

7-Methoxy-(8-(3-4-[4-(3,4,5-trimethoxyphenoxy)-3-nitrobenzoyl]piperazinopentyloxy)-(11aS)-1,2,3,11a-tetrahydro-5H-pyrrolo[2,1-c][1,4]benzodiazepin-5-one (33c);

7-Methoxy-(8-(3-4-[4-(3,4,5-trimethoxyphenoxy)-3-nitrobenzoyl]piperazinohexyloxy)-(11aS)-1,2,3,11a-tetrahydro-5H-pyrrolo[2,1-c][1,4]benzodiazepin-5-one (33d).

In yet another embodiment of the present invention, structural formula of the diaryl ether linked pyrrolo[2,1-c][1,4] benzo diazepine hybrids of general formula A are:

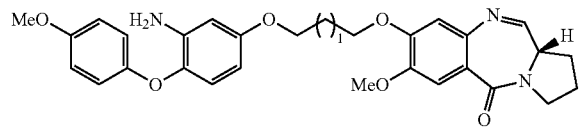
(10a)

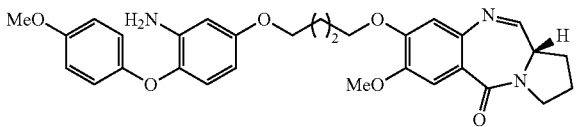
(10b)

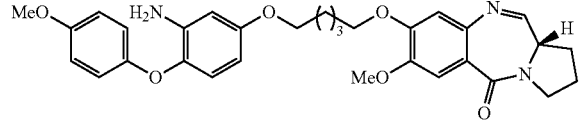
(10c)

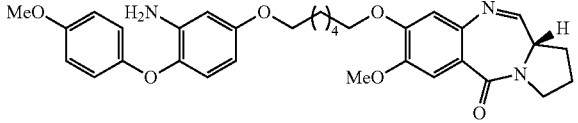
(10d)

-continued
(10e)
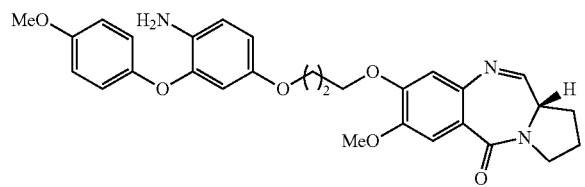
(10f)
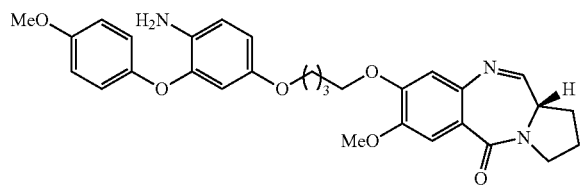
(10g)
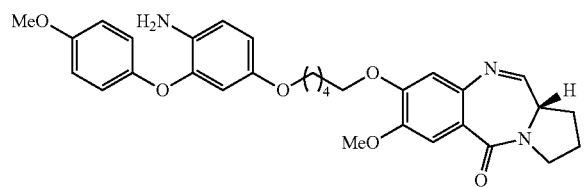
(10h)
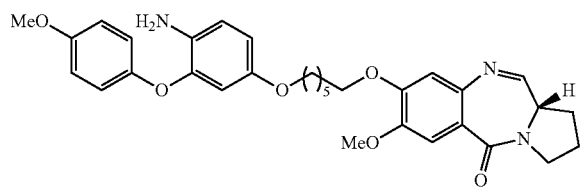
(11a)
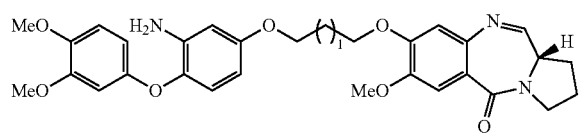
(11b)
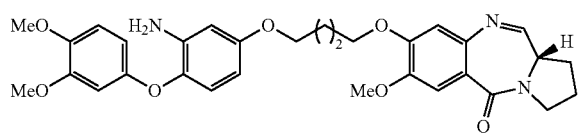
(11c)
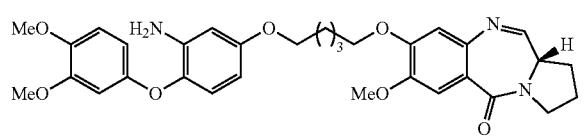
(11d)
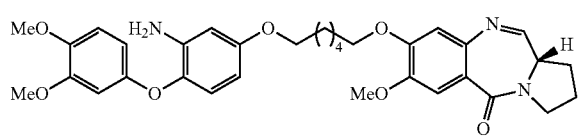
(11e)
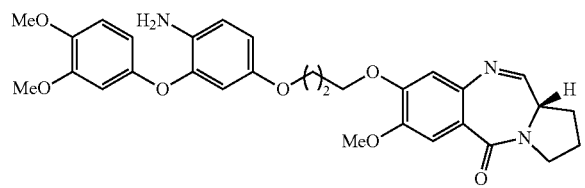
(11f)
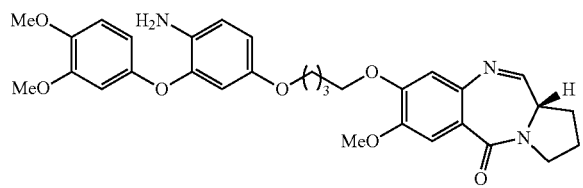
(11g)
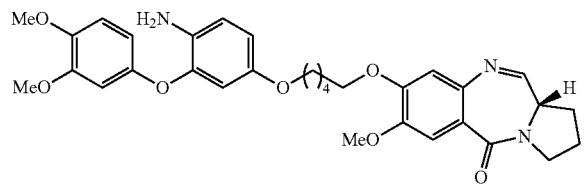
(11h)
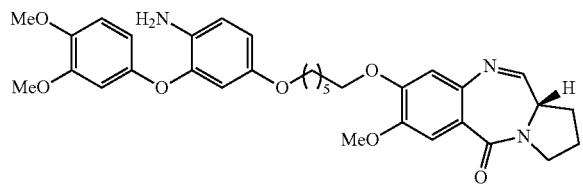
(12a)
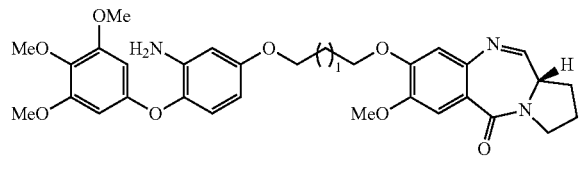
(12b)
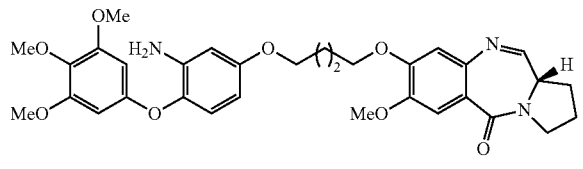
(12c)
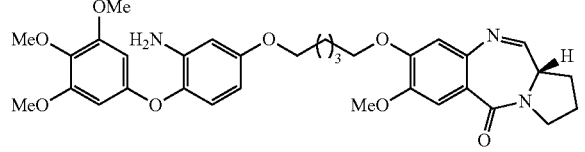
(12d)
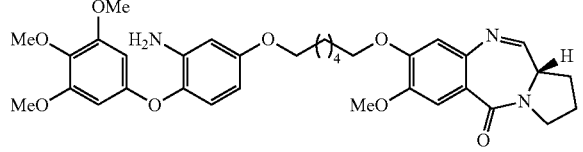

-continued

-continued
(14e)
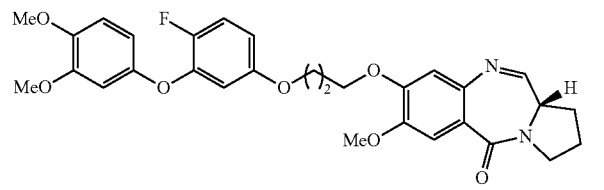
(14f)
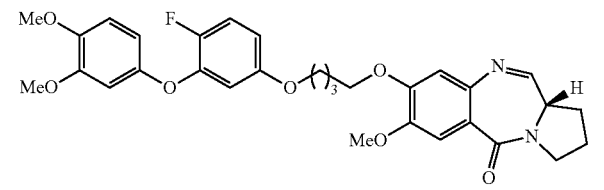
(14g)
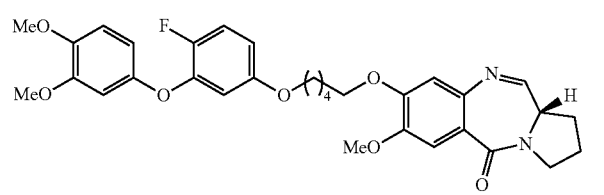
(14h)
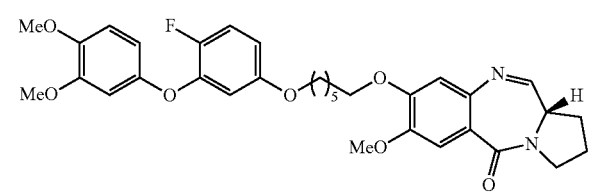
(15a)
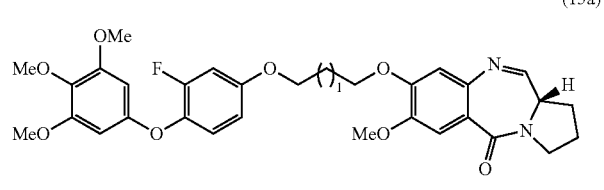
(15b)
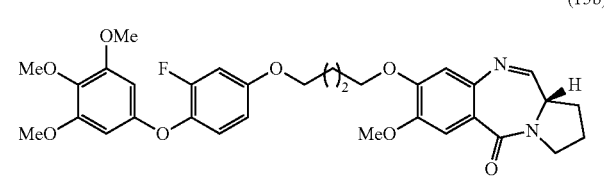
(15c)
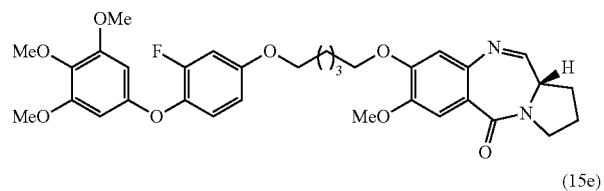
(15d)
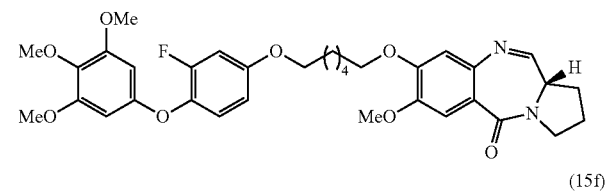
(15e)
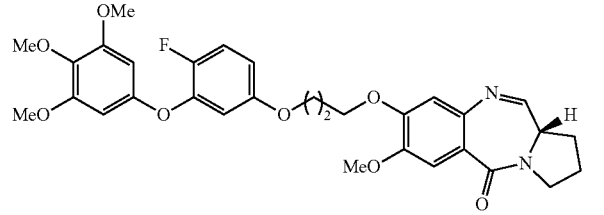
(15f)
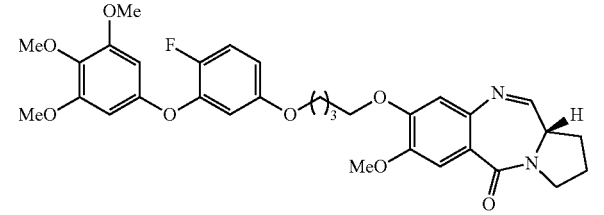
(15g)
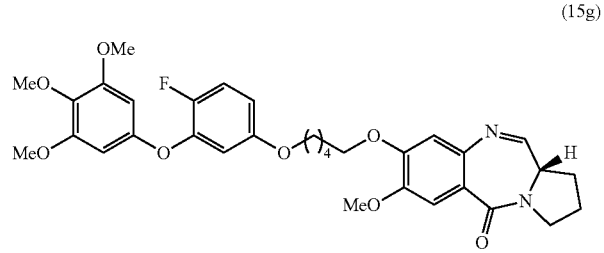
(15h)
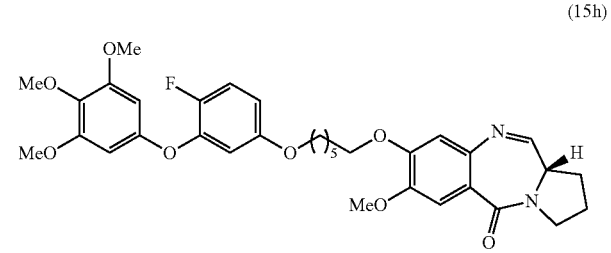
(16a)
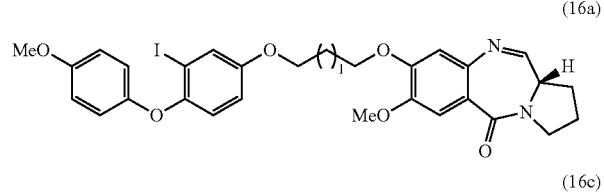
(16b)
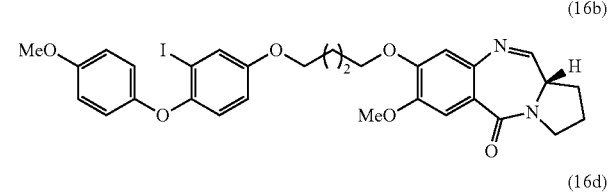
(16c)
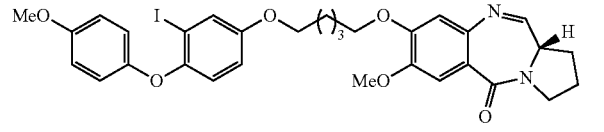
(16d)
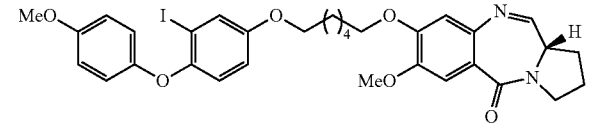

-continued
(16e)
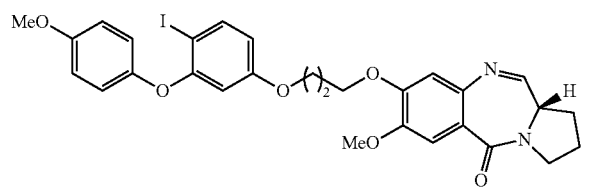
(16f)
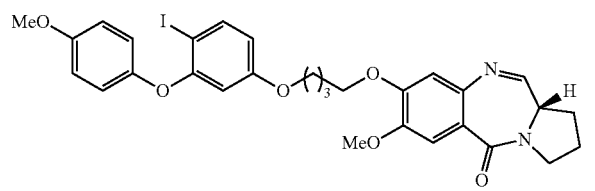
(16g)
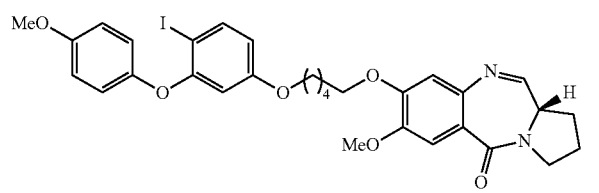
(16h)
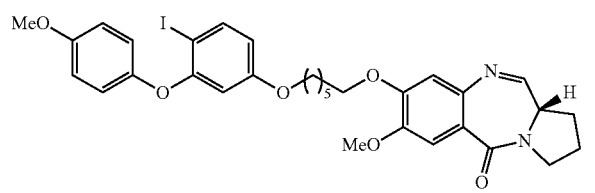
(17a)
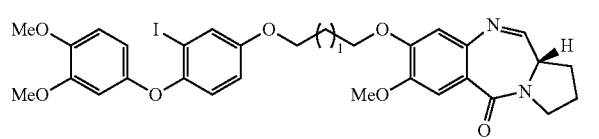
(17b)
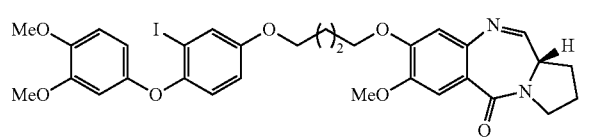
(17c)
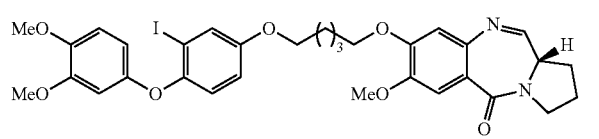
(17d)
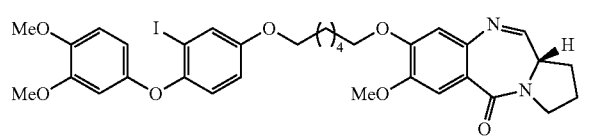
(17e)
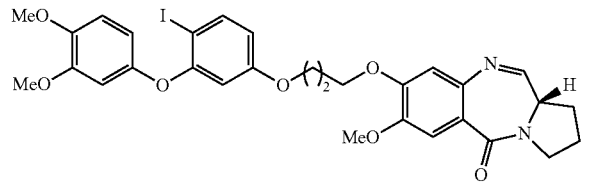
(17f)
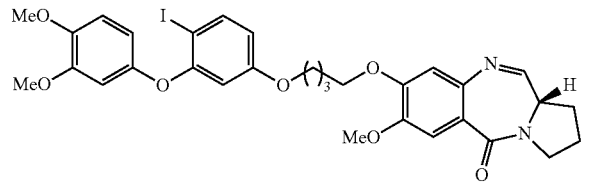
(17g)
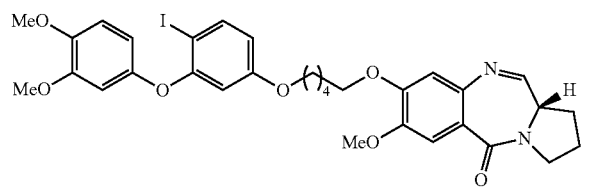
(17h)
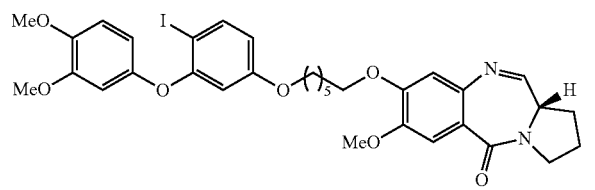
(18a)
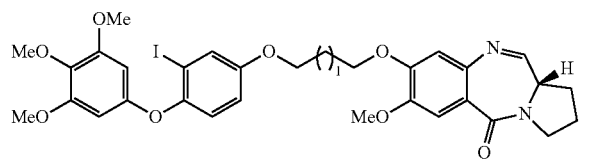
(18b)
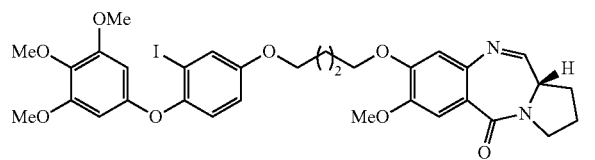
(18c)
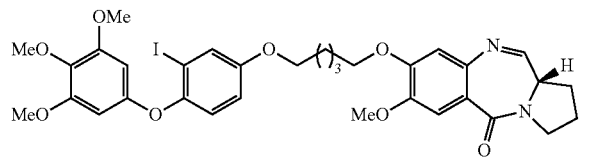
(18d)
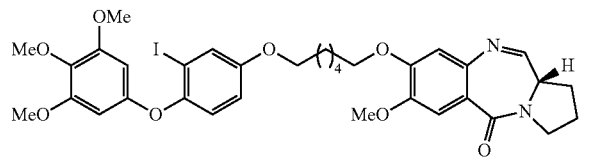

-continued
(18e)
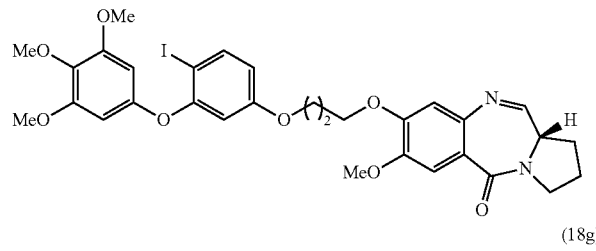
(18f)
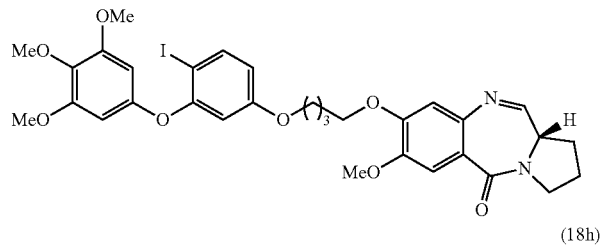
(18g)
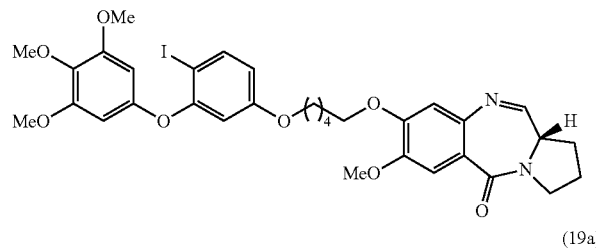
(18h)
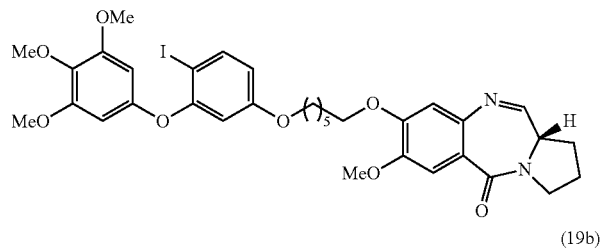
(19a)
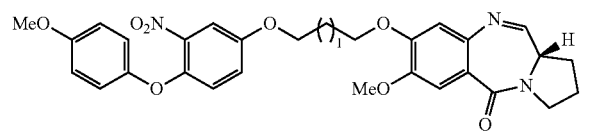
(19b)
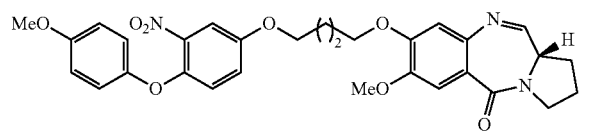
(19c)
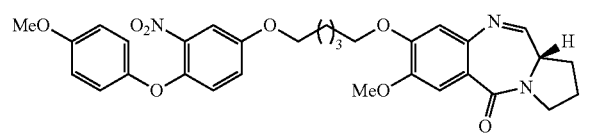
(19d)
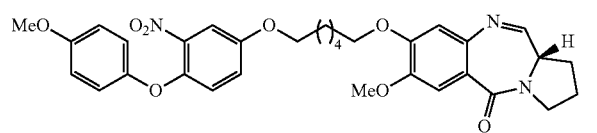
(19e)
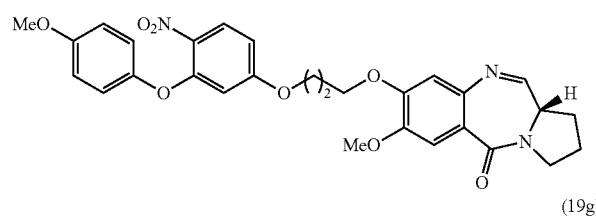
(19f)
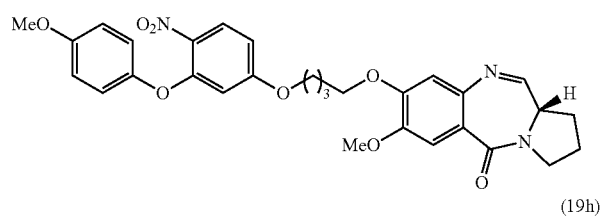
(19g)
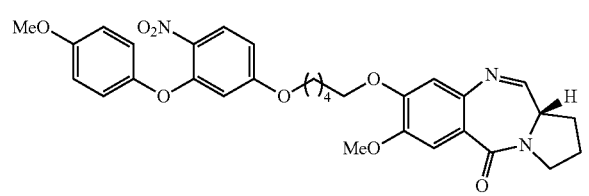
(19h)
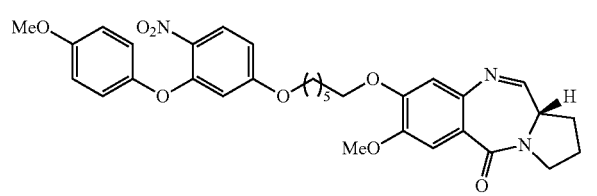
(20a)
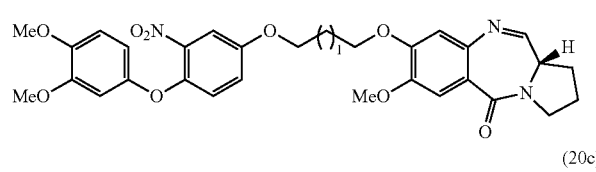
(20b)
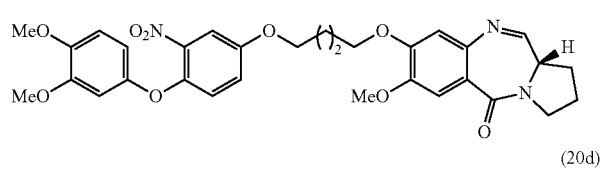
(20c)
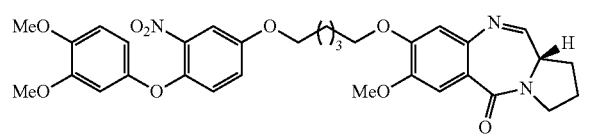
(20d)
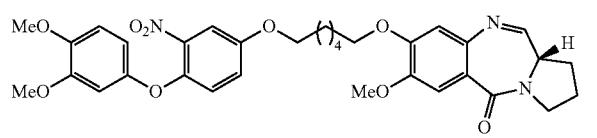

-continued
(20e)
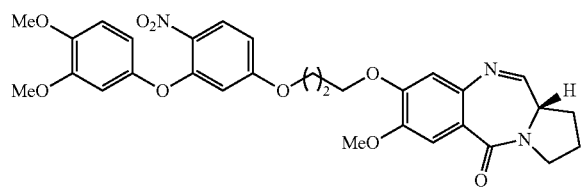
(20f)
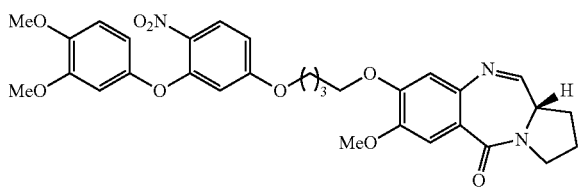
(20g)
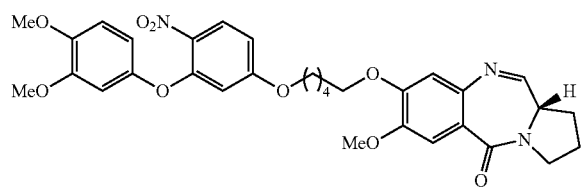
(20h)
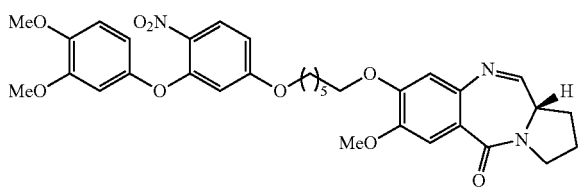
(21a)
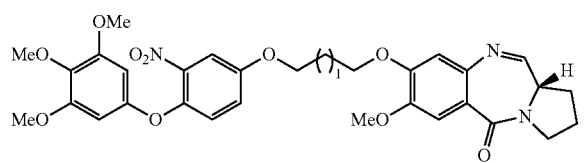
(21b)
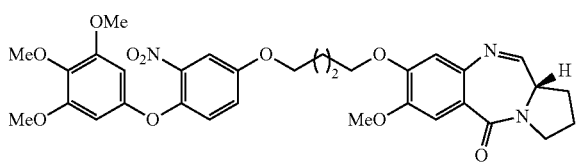
(21c)
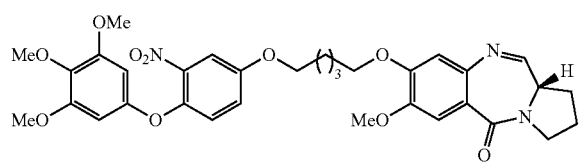
(21d)
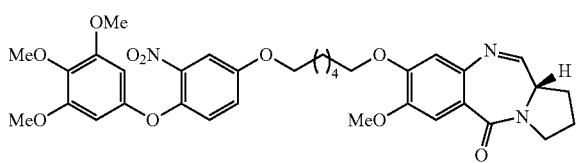
(21e)
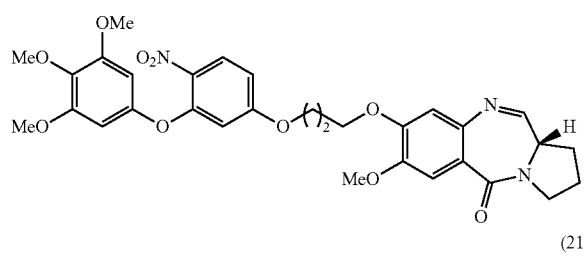
(21f)
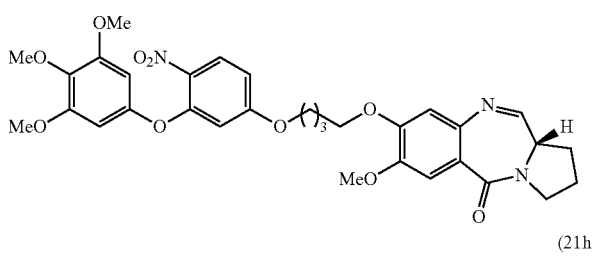
(21g)
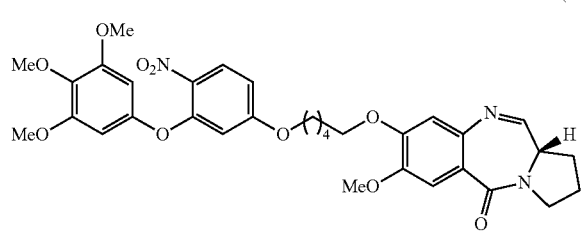
(21h)
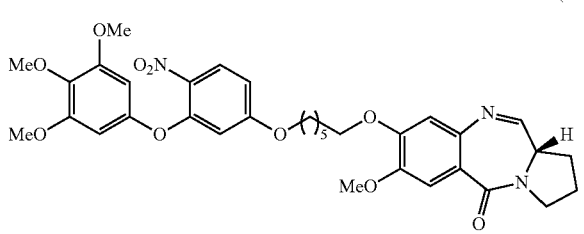
(22a)
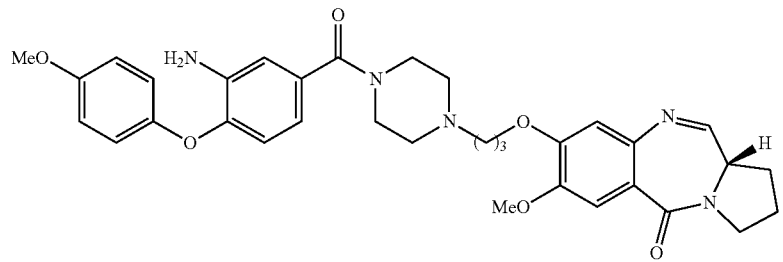

(22b)
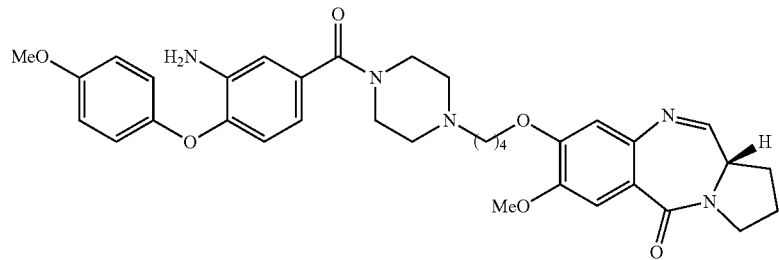
(22c)
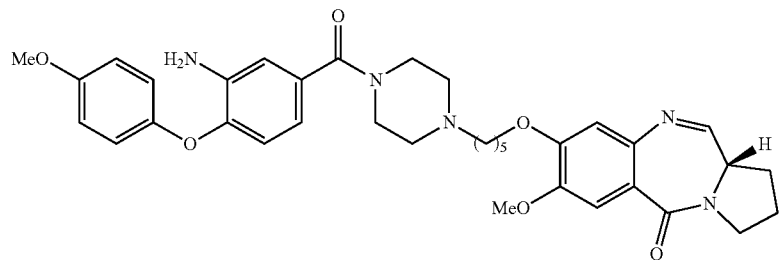
(22d)
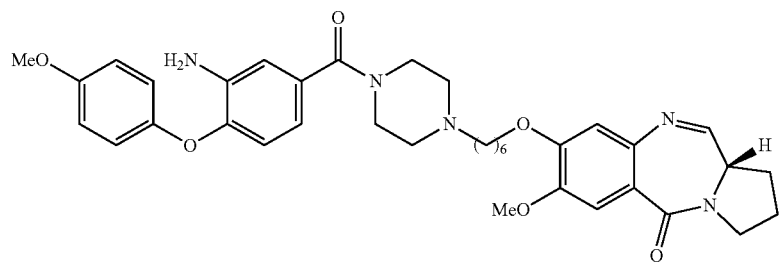
(23a)
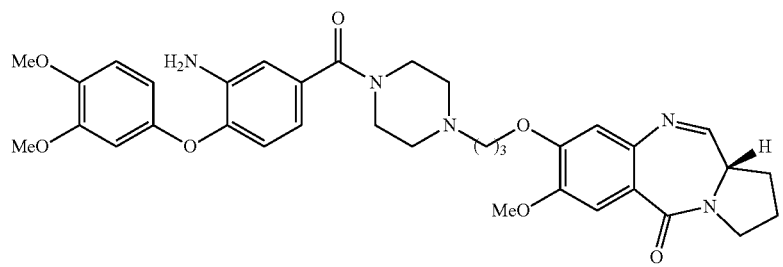
(23b)
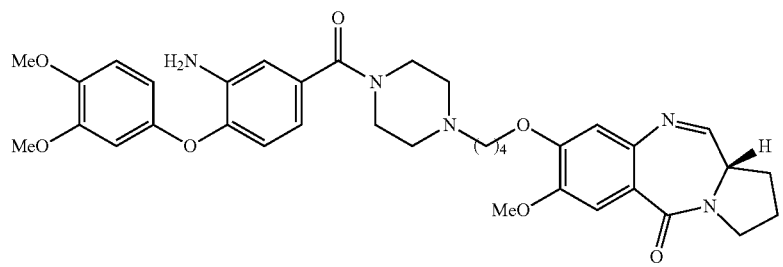
(23c)
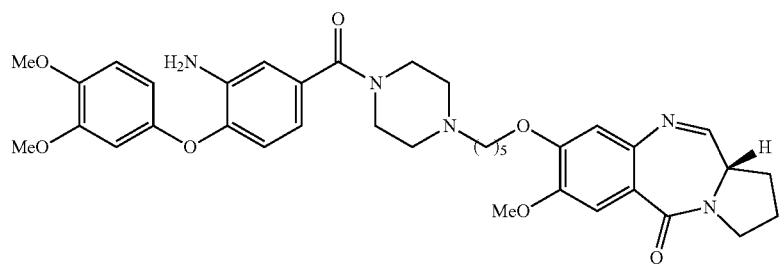

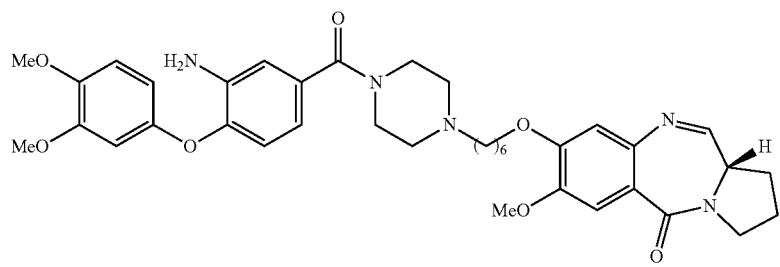
(23d)
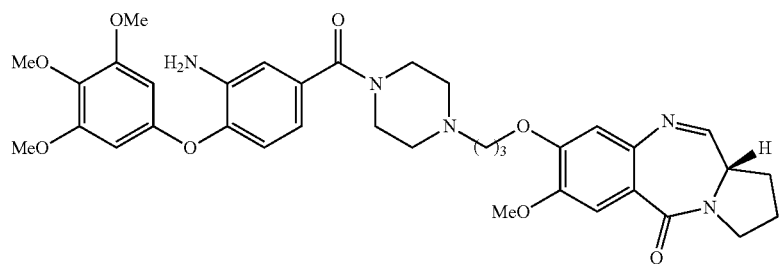
(24a)
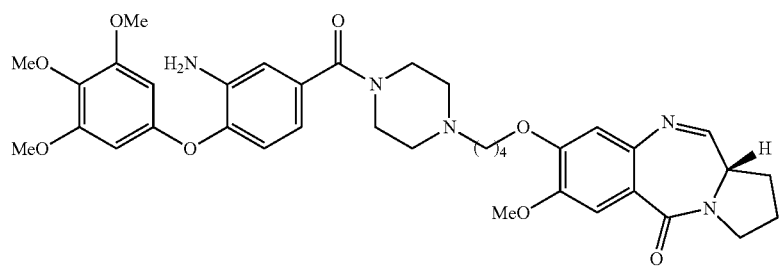
(24b)
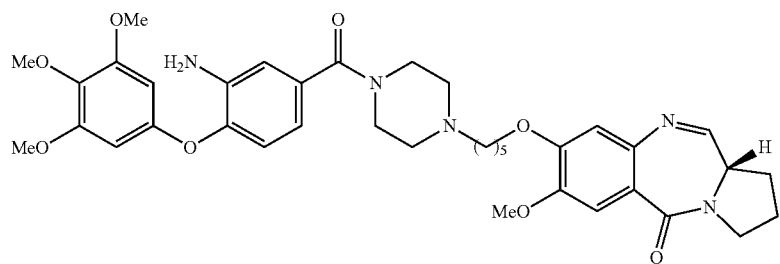
(24c)
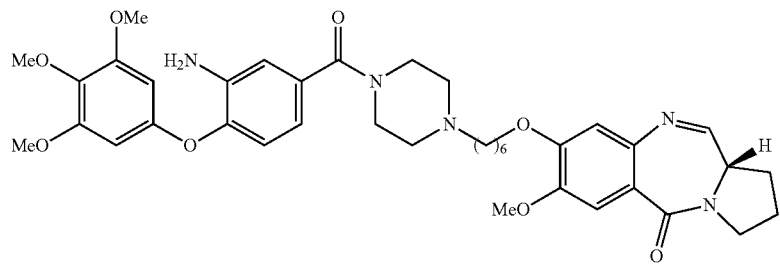
(24d)
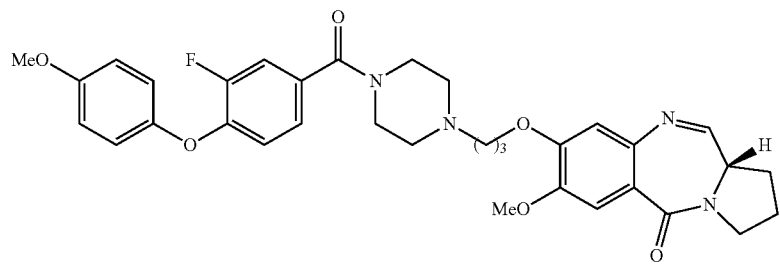
(25a)

(25b)
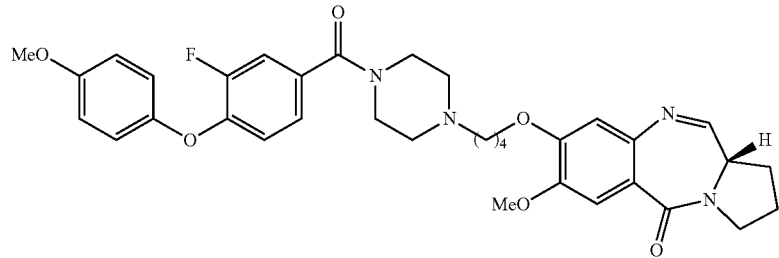
(25c)
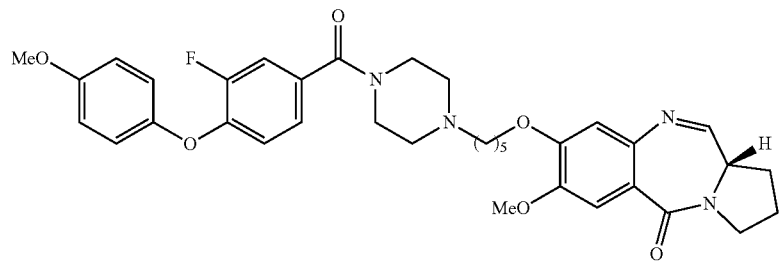
(25d)
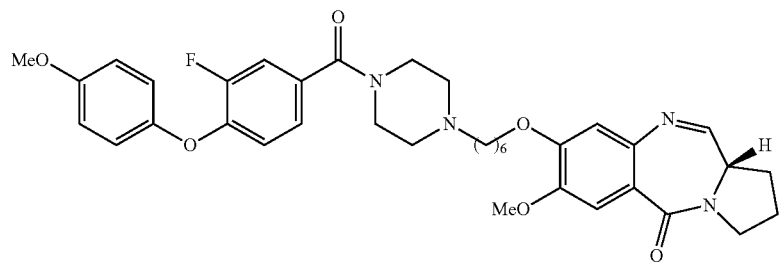
(26a)
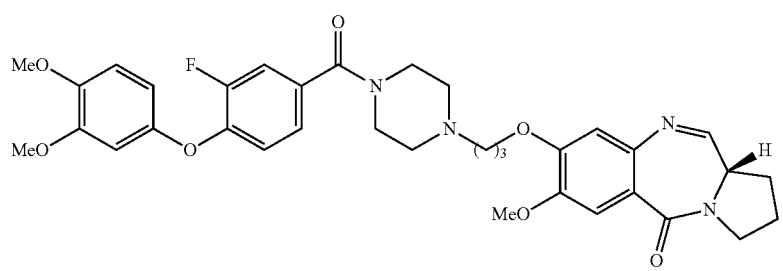
(26b)
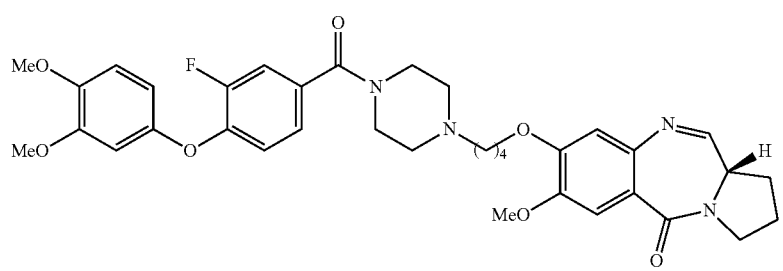
(26c)
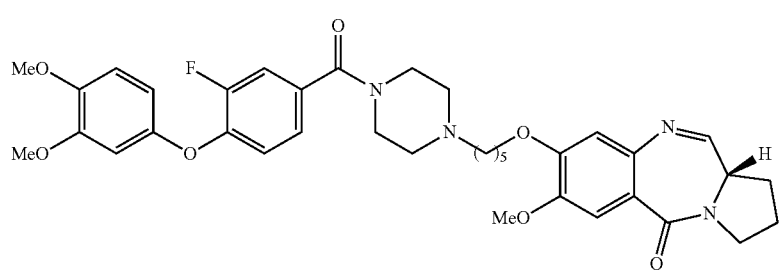

-continued
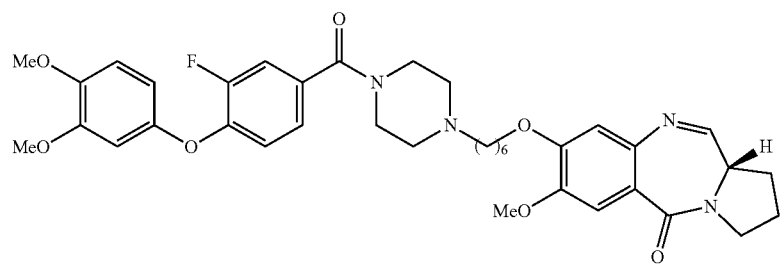
(26d)
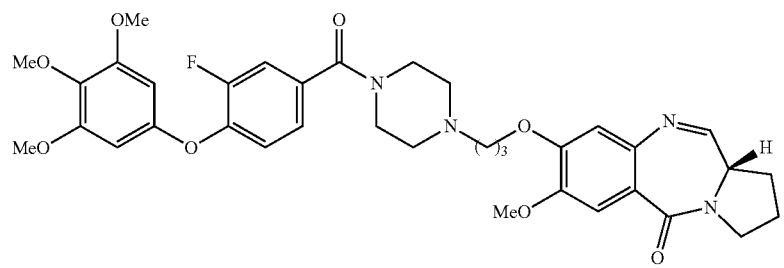
(27a)
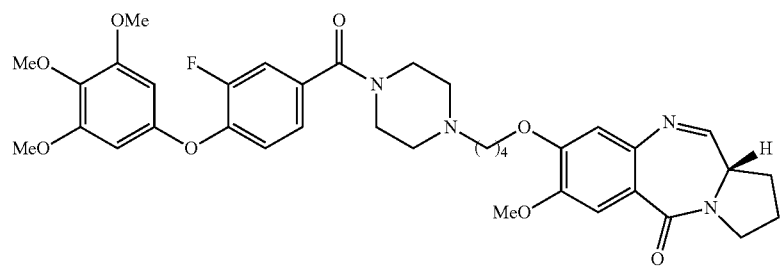
(27b)
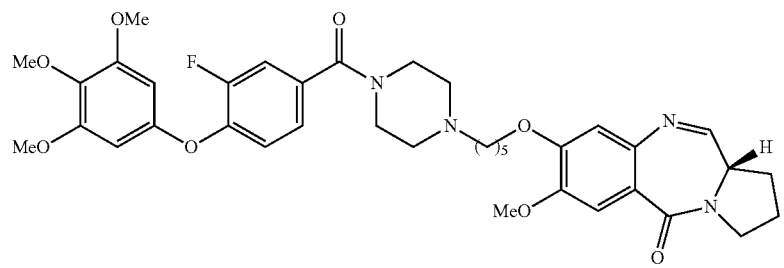
(27c)
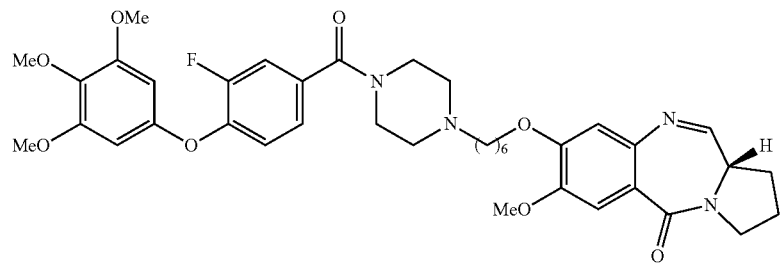
(27d)
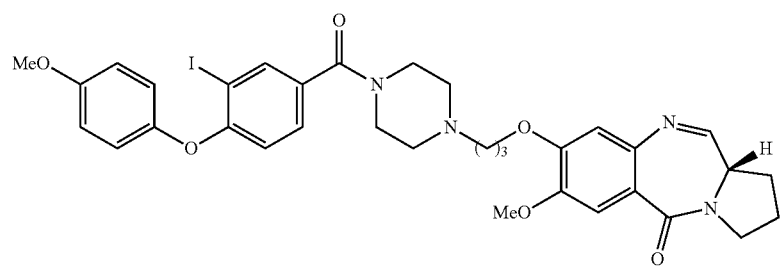
(28a)

-continued
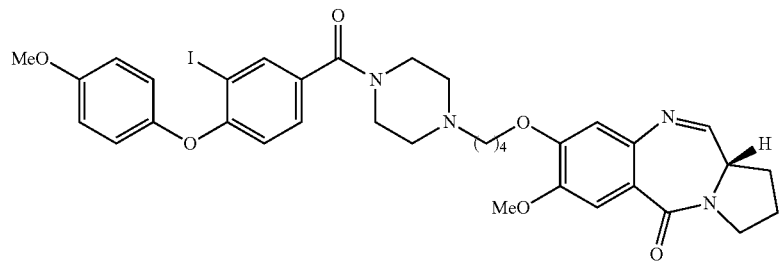
(28b)
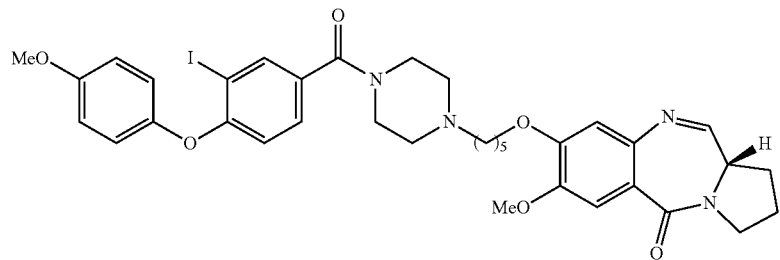
(28c)
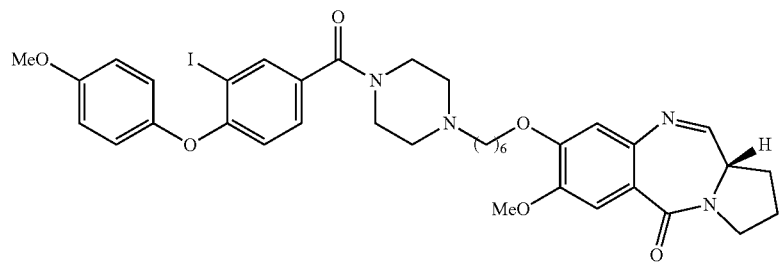
(28d)
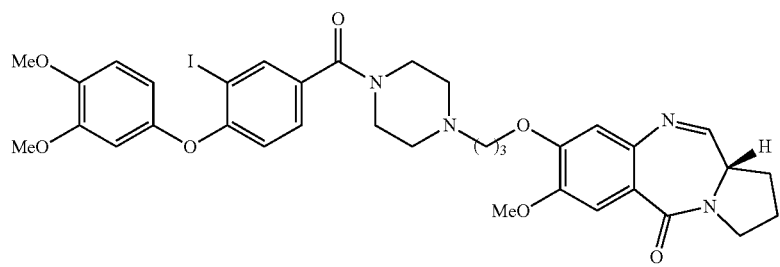
(29a)
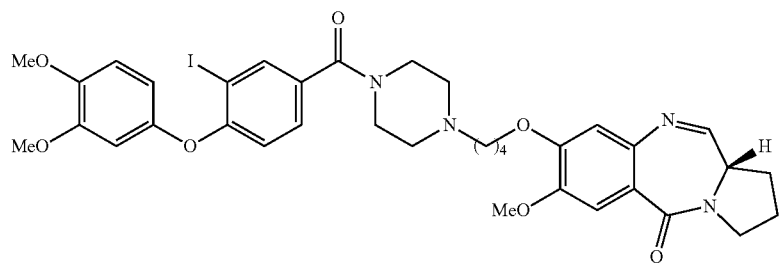
(29b)
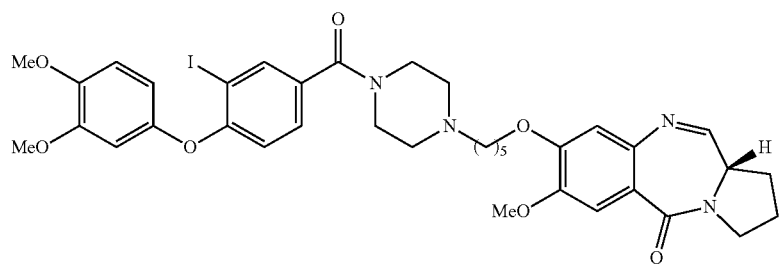
(29c)

(29d)
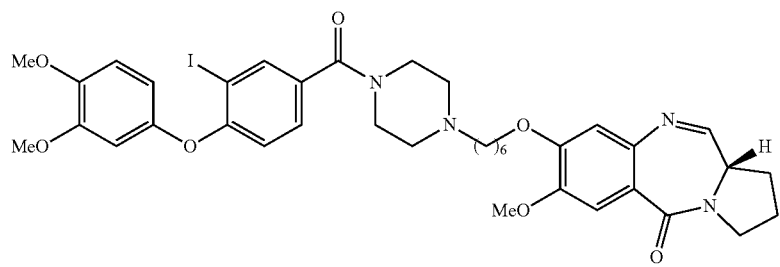
(30a)
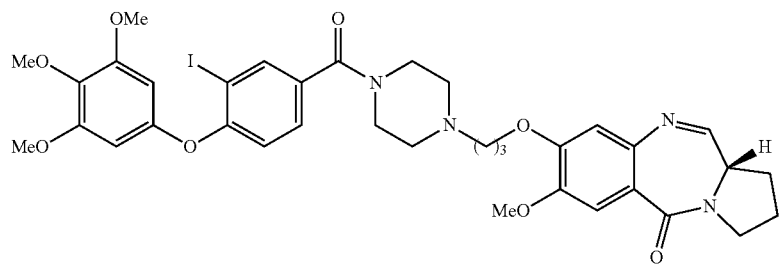
(30b)
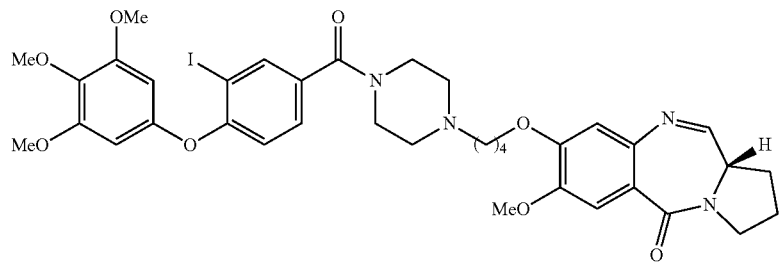
(30c)
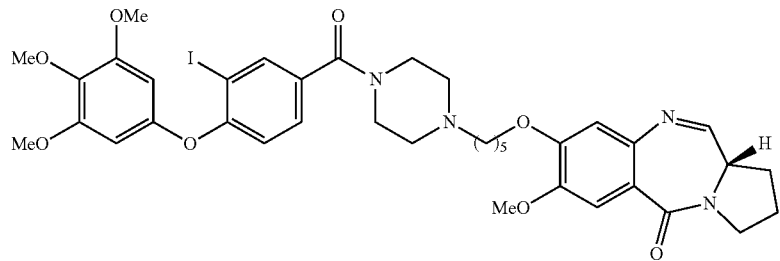
(30d)
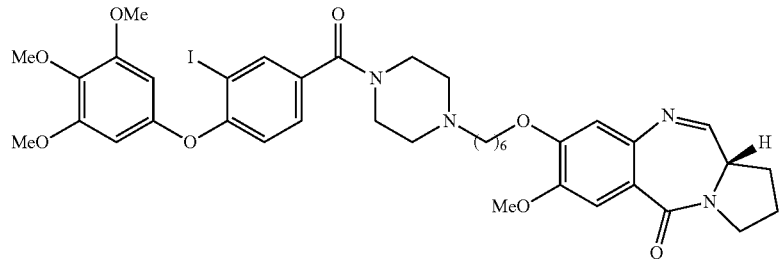
(31a)
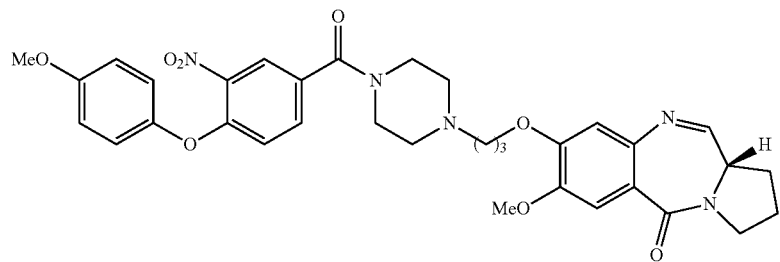

(31b)
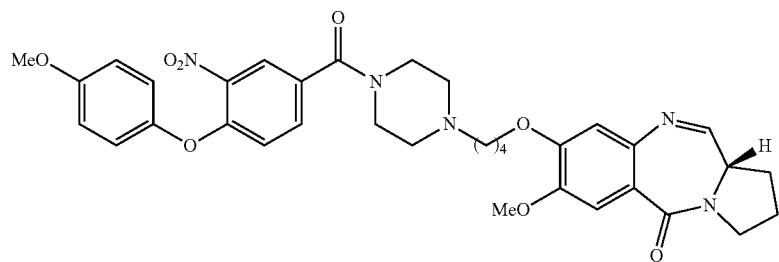
(31c)
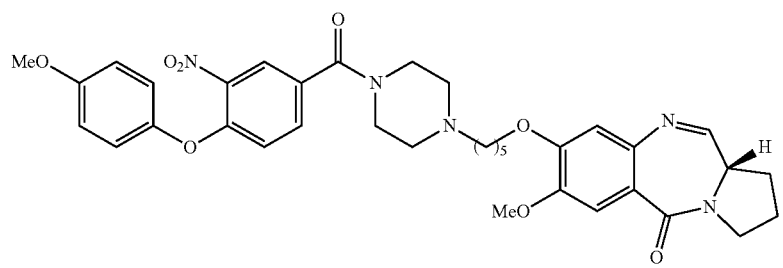
(31d)
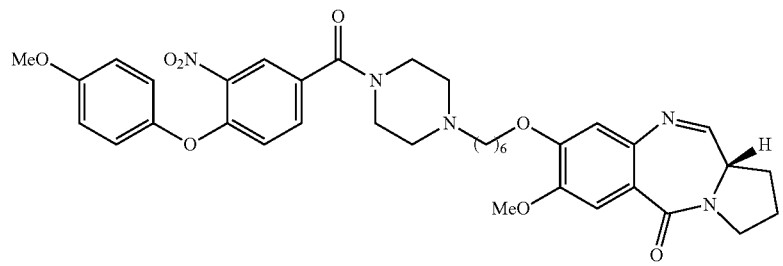
(32a)
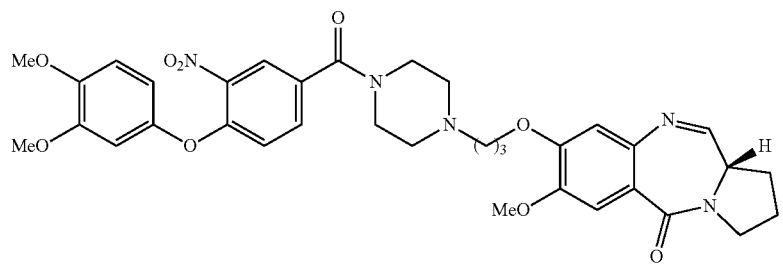
(32b)
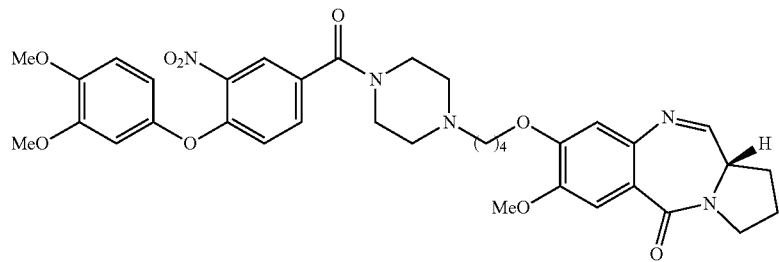
(32c)
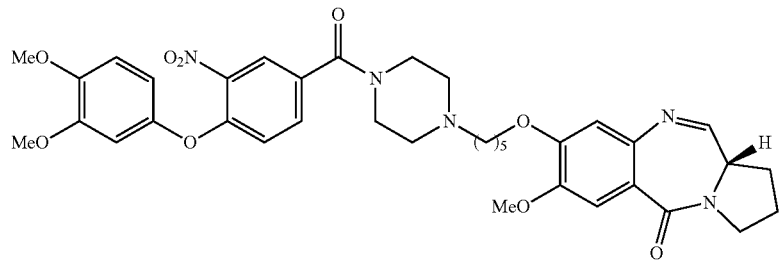

(32d)
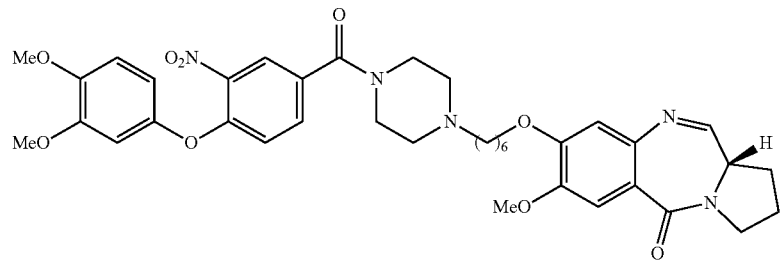
(33a)
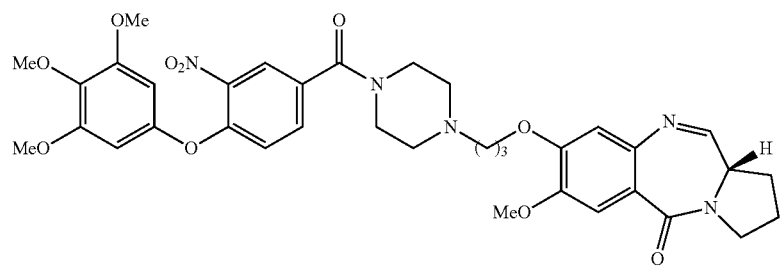
(33b)
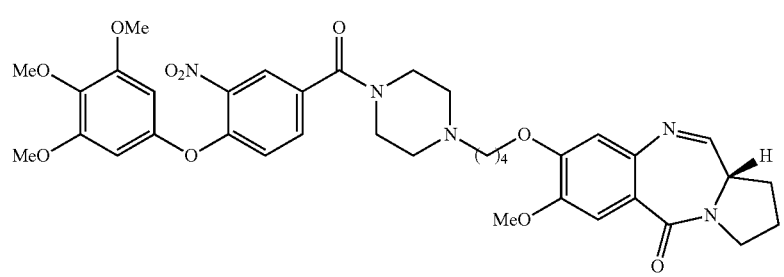
(33c)
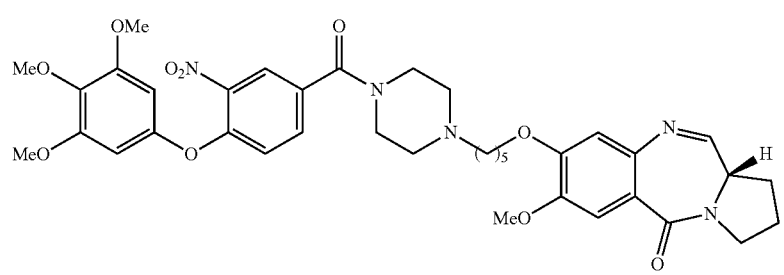
(33d)
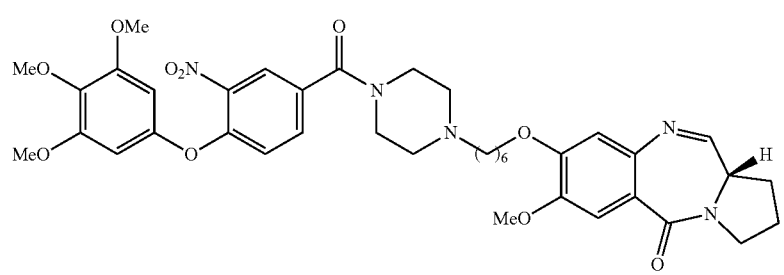

In
In yet another embodiment of the present invention, pyrrolo[2,1-c][1,4]benzodiazepine linked diaryl ether conjugates of general formula A are useful as anticancer agent.

Yet another embodiment of the present invention provides a process for the preparation of pyrrolo[2,1-c][1,4]-benzodiazepine linked diaryl ether conjugates attached through different alkane spacers of general formula A by reacting compound of formula 3 with compound having formula 5 or compound having formula 7 to obtain compound of formula 8 or 9.

The precursors [4-(n-bromoalkoxy)-5-methoxy-2-nitrophenyl]2-[di(ethylsulfanyl)methyl]tetrahydro-1H-1-pyrrolylmethanone of formula 2(a-d) for the preparation of compound of formula 3 have been synthesized by known literature methods (Kamal et al. *J. Med. Chem.*, 2002, 45, 4679. *Bioorg. Med. Chem. Lett.* 2007, 19, 5345. *Bioorg. Med. Chem. Lett.* 2007, 19, 5345. *Bioorg. Med. Chem. Lett.* 2008, 18, 1468.). The substituted diaryl ether precursors 5a-x have been prepared by reacting 4-(benzyloxy)-1-fluoro-2-nitrobenzene and methoxy substituted phenol, followed by debenzylation. The precursors 7a-l have been prepared by reacting tert-butyl 4-(4-chloro-3-nitrobenzoyl)piperazine-1-carboxylate and methoxy substituted phenol, followed by deprotection of Boc.

In yet another embodiment of the present invention, the process for the preparation of pyrrolo[2,1-c][1,4]benzodiazepine linked diaryl ether conjugates attached through different alkane spacers of general formula A, comprises the steps of:

a) reacting compound of formula 1 with dibromo alkanes in the presence of $K_2CO_3$ in acetone solvent at refluxing temperature ranging between 57 to 60° C. for 12 to 24 hrs to obtain compound of formula 2;

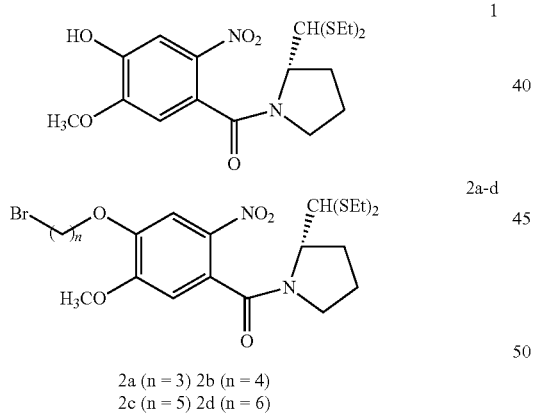

2a (n = 3) 2b (n = 4)
2c (n = 5) 2d (n = 6)

b) reacting compound of formula 2 as obtained in step (a) with $SnCl_2.2H_2O$ in MeOH solvent at refluxing temperature ranging between 67 to 70° C. for 4 to 5 hrs to obtain compound of formula 3(a-d).

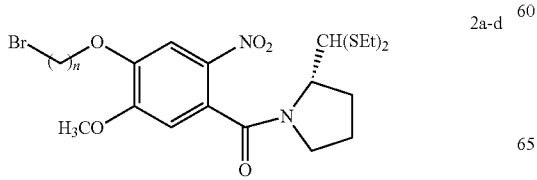

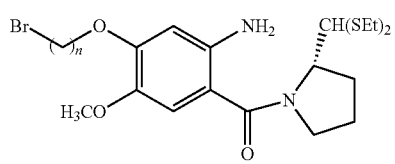

3a (n = 3) 3b (n = 4)
3c (n = 5) 3d (n = 6)

c) reacting compound of formula 4(a-x) with $TiCl_4$ in dichloromethane solvent at 0 to 5° C. for 30 to 60 min to obtain compound of formula 5(a-x).

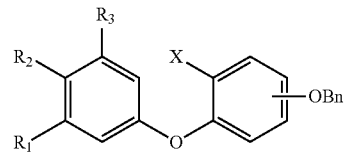

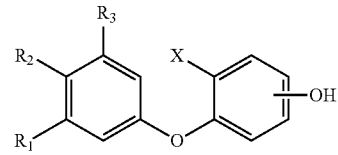

d) reacting compound of formula 6(a-l) with trifluoro acetic acid in dichloromethane solvent at 0 to 5° C. for 10 to 12 hrs to obtain compound of formula 7(a-l).

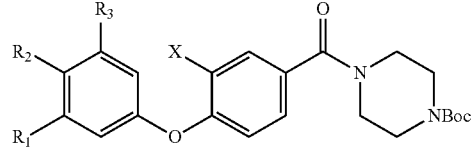

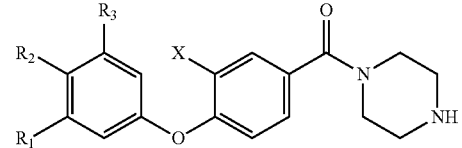

e) reacting compound of formula 3(a-d) as obtained in step (b) with a compound of formula 5(a-x) as obtained in step (c) or formula 7(a-l) as obtained in step (d) in the ratio ranging between 1:1 ratio in the presence of $K_2CO_3$ in acetone solvent at refluxing temperature in the range of 56 to 60° C. for period of 24 to 48 hours to obtain the amino compounds of general formula 8 or 9 respectively.

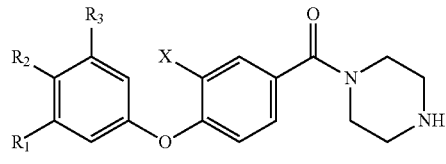

R₁, R₂, R₃ = H or OMe;
X = NO₂, NH₂, F, I;

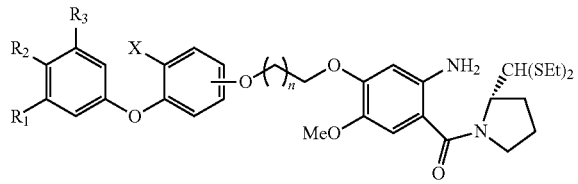

R₁, R₂, R₃ = H or OMe;
X = NO₂, NH₂, F or I;
n = 2, 3, 4 or 5

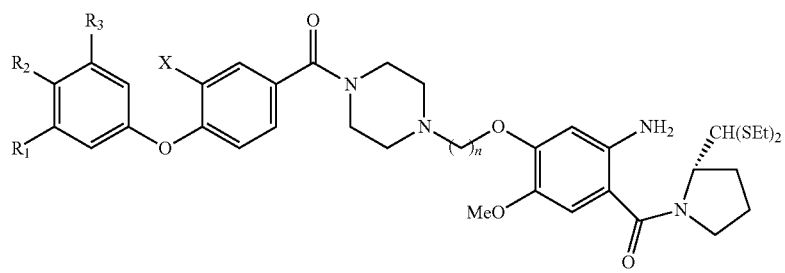

R₁, R₂, R₃ = H or OMe;
X = NO₂, NH₂, F, I;
n = 3, 4, 5 or 6 f) reacting the amino compound of general formula 8 and 9 as obtained in step (e) with a deprotecting agent $HgCl_2$ and $CaCO_3$ in $MeCN:H_2O$ (4:1 ratio) at temperature in the range of 27 to 30° C. for period of 12 to 24 hours by known method to obtain the desired compound of formula 10(a-h) to 21(a-h) or 22(a-d) to 33(a-d).

These new analogues 10(a-h) to 22(a-h) and 23(a-d) to 33(a-d) of pyrrolo[2,1-c][1,4]benzo diazepine hybrids linked at C-8 position have shown promising DNA binding activity and efficient anticancer activity in various cell lines. The molecules synthesized are of massive biological significance with potential sequence selective DNA-binding property. This present invention is illustrated in Scheme 1 and 2 as herein given below.

In yet another embodiment of the present invention, said compounds exhibit $\Delta T_m$ value in the range of 2.9 to 4.9 at 0 hr and $\Delta T_m$ value in the range of 3.6 to 7.3 at 18 hrs after incubation at 37° C.

In yet another embodiment of the present invention, said compounds exhibit in-vitro anticancer activity against human cancer cell lines selected from the group consisting of breast cancer cell lines (MCF-7, ZR-75-1), lung cancer cell lines (A-549, Hop62), Cervix cancer cell line (SiHa), colon cancer cell line (Colo205), oral cancer cell lines (KB, GURAV, DWD), prostrate cancer cell line (PC3) and ovarian cancer cell line (A-2780).

In yet another embodiment of the present invention, concentration of pyrrolo[2,1-c][1,4]benzodiazepine linked diaryl ether conjugates having formula 10g, 11g, 12g, 16c, 17c, 17g, 18c, 19g, 20c, 20g, 21c, 21g, 22c, 23c, 24c, 31c, 32c and 33c used for breast cancer cell line (ZR751) for $GI_{50}$, is in the range of 0.13-3.80 μm at an exposure period of at least 48 hrs.

The concentration of pyrrolo[2,1-c][1,4]-benzodiazepine linked diaryl ether conjugates having formula 10g, 11g, 12g, 16c, 17c, 17g, 18c, 19g, 20c, 20g, 21c, 21g, 22c, 23c, 24c, 31c, 32c and 33c used for lung cancer cell line (A549) for $GI_{50}$ is in the range of 0.14-3.04 μm at an exposure period of at least 48 hrs.

The concentration of pyrrolo[2,1-c][1,4]-benzodiazepine linked diaryl ether conjugates having formula 10g, 11g, 12g, 16c, 17c, 17g, 18c, 19g, 20c, 20g, 21c, 21g, 22c, 23c, 24c, 31c, 32c and 33c used for ovarian cancer cell line (A2780) for $GI_{50}$ is in the range of 0.14-3.10 μm at an exposure period of at least 48 hrs.

The concentration of pyrrolo[2,1-c][1,4]benzodiazepine linked diaryl ether conjugate having formula 10g, 11g, 12g, 16c, 17c, 17g, 18c, 19g, 20c, 20g, 21c, 21g, 22c, 23c, 24c, 31c, 32c and 33c used for lung cancer cell line (Hop62) for $GI_{50}$ is in the range of 0.147-3.10 μm at an exposure period of at least 48 hrs.

The concentration of pyrrolo[2,1-c][1,4]-benzodiazepine linked diaryl ether conjugates having formula 10g, 11g, 12g, 16c, 17c, 17g, 18c, 19g, 20c, 20g, 21c, 21g, 22c, 23c, 24c, 31c, 32c and used for oral cancer cell line (KB) for $GI_{50}$ is in the range of <0.1-3.15 μm at an exposure period of at least 48 hrs.

The concentration of Pyrrolo[2,1-c][1,4]benzodiazepine linked diaryl ether conjugates having formula 10g, 11g, 12g, 16c, 17c, 17g, 18c, 19g, 20c, 20g, 21c, 21g, 22c, 23c, 24c, 31c, 32c and 33c, used for Cervix cancer cell line (SiHa) for $GI_{50}$, is in the range of 0.19-3.88 μm at an exposure period of at least 48 hrs.

The concentration of pyrrolo[2,1-c][1,4]-benzodiazepine linked diaryl ether conjugates having formula 10g, 11g, 12g, 16c, 17c, 17g, 18c, 19g, 20c, 20g, 21c, 21g, 22c, 23c, 24c, 31c, 32c and 33c, used for oral cancer cell line (Gurav) for $GI_{50}$ is in the range of 0.12-2.86 μm at an exposure period of at least 48 hrs.

The concentration of pyrrolo[2,1-c][1,4]benzodiazepine linked diaryl ether conjugates having formula 10g, 11g, 12g, 16c, 17c, 17g, 18c, 19g, 20c, 20g, 21c, 21g, 22c, 23c, 24c, 31c, 32c and 33c used for breast cancer cell line (MCF7) for $GI_{50}$ is in the range of <0.1-3.60 μm at an exposure period of at least 48 hrs.

The concentration of pyrrolo[2,1-c][1,4]benzodiazepine linked diaryl ether conjugates having formula 10g, 11g, 12g, 16c, 17c, 17g, 18c, 19g, 20c, 20g, 21c, 21g, 22c, 23c, 24c, 31c, 32c and 33c used for colon cancer cell line (Colo205) for $GI_{50}$ is in the range of 0.13-3.12 μm at an exposure period of at least 48 hrs.

The concentration of pyrrolo[2,1-c][1,4]benzodiazepine linked diaryl ether conjugates having formula 10g, 11g, 12g, 16c, 17c, 17g, 18c, 19g, 20c, 20g, 21c, 21g, 22c, 23c, 24c, 31c, 32c and 33c used for oral cancer cell line (DWD) for $GI_{50}$ is in the range of 0.13-3.00 μm at an exposure period of at least 48 hrs.

The concentration of pyrrolo[2,1-c][1,4]benzodiazepine linked diaryl ether conjugates having formula 10g, 11g, 12g, 16c, 17c, 17g, 18c, 19g, 20c, 20g, 21c, 21g, 22c, 23c, 24c, 31c, 32c and 33c, concentration of the compound used for prostate cancer cell line (PC3) for $GI_{50}$ is in the range of 0.16-2.84 μm at an exposure period of at least 48 hrs.

The precursors [4-(n-bromoalkoxy)-5-methoxy-2-nitrophenyl]2-[di(ethylsulfanyl)methyl]tetrahydro-1H-1-pyrrolylmethanone of formula 2a-d (Kamal et al. *J. Med. Chem.*, 2002, 45, 4679. *Bioorg. Med. Chem. Lett.* 2007, 19, 5345. *Bioorg. Med. Chem. Lett.* 2007, 19, 5345. *Bioorg. Med. Chem. Lett.* 2008, 18, 1468.) Have been synthesized by known literature methods. The substituted diaryl ether precursors 5a-x has been prepared by reacting 4-(benzyloxy)-1-fluoro-2-nitrobenzene and methoxy substituted phenol, fallowed by debenzylation. The precursors 7a-l have been prepared by reacting tert-butyl 4-(4-chloro-3-nitrobenzoyl)piperazine-1-carboxylate and methoxy substituted phenol, fallowed by deprotection of Boc.

These new analogues 10a-h to 22a-h and 23a-d to 33a-d of pyrrolo[2,1-c][1,4]benzo diazepine hybrids linked at C-8 position have shown promising DNA binding activity and efficient anticancer activity in various cell lines. The molecules synthesized are of massive biological significance with potential sequence selective DNA-binding property. This present invention is illustrated in Scheme 1 and 2 as herein given below:
  i. The ether linkage at C-8 position of DC-81 intermediates with diaryl ether moieties.
  ii. Refluxing the reaction mixtures for 48 hrs.
  iii. Synthesis of C-8 linked PBD antitumour antibiotic hybrid imines.

Purification by column chromatography using different solvents like ethyl acetate, hexane, chloroform and methanol

EXAMPLES

The following examples are given by way of illustration of the working of the invention in actual practice and therefore should not be construed to limit the scope of present invention.

Example 1

7-Methoxy-(8-5-[4-amino-3-(4-methoxyphenoxy)phenoxy]pentyloxy)-(11aS)-1,2,3,11a-tetrahydro-5H-pyrrolo[2,1-c][1,4]benzodiazepin-5-one (10g)

To a solution of 4-amino-3-(4-methoxyphenoxy)phenol (5b) (231 mg, 1 mmol) in acetone (10 mL) was added anhydrous $K_2CO_3$ (552 mg, 4 mmol) and the (S)-(2-amino-4-(5-bromopentyloxy)-5-methoxyphenyl)(2(bis(ethylthio)methyl)pyrrolidin-1-yl)methan one (3c) (518 mg, 1 mmol). The reaction mixture was heated to reflux at 60° C. for 48 hrs. After completion of the reaction as indicated by TLC, potassium carbonate was removed by suction filtration and the solvent was removed under vacuum. The crude product thus obtained was purified by column chromatography using ethyl acetate-hexane (8:2) as eluant to afford pure amino compound (521 mg, 78%).

$^1$H NMR (CDCl$_3$, 300 MHz): δ 1.24-1.27 (t, 3H, J=7.36 Hz), 1.30-1.35 (t, 2H, J=6.79 Hz), 1.54-1.72 (m, 6H), 1.81-1.98 (m, 6H), 2.61-2.79 (m, 4H), 3.51-3.69 (m, 2H), 3.76 (s, 3H), 3.78 (s, 3H), 4.00 (t, 4H, J=6.23 Hz), 4.66-4.70 (m, 1H), 4.86 (d, 1H, J=3.77 Hz), 5.25 (brs, 2H), 5.29 (brs, 2H), 6.21 (s, 1H), 6.81 (s, 1H), 6.83-6.88 (m, 3H), 6.91-6.94 (m, 4H), 7.22 (d, 1H, J=2.86 Hz); ESIMS: m/z 669 (M$^+$+1).

A solution of amino compound (668 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (5%) to give compound 10g (295 mg, 54%). This material was repeatedly evaporated from CHCl$_3$ in vacuum to generate the imine form.

$^1$H NMR (CDCl$_3$, 300 MHz): δ 1.53-1.57 (m, 4H), 1.70-1.73 (m, 2H), 1.81-1.93 (m, 2H), 1.98-2.09 (m, 2H), 3.68-3.75 (m, 3H), 3.82 (s, 3H), 3.92 (s, 3H), 4.06 (t, 4H, J=6.48 Hz), 6.37 (d, 2H, J=2.45 Hz), 6.51 (d, 1H, J=8.30 Hz), 6.73 (d, 1H, J=8.68 Hz), 6.79 (d, 1H, J=3.58 Hz), 6.86 (d, 2H, J=9.25 Hz), 6.92 (d, 2H, J=8.68 Hz), 7.50 (s, 1H), 7.65 (d, 1H, J=3.40 Hz); ESIMS: m/z 546 (M$^+$+1).

Example 2

7-Methoxy-(8-5-[4-amino-3-(3,4-dimethoxyphenoxy)phenoxy]pentyloxy)-(11aS)-1,2,3,11a-tetrahydro-5H-pyrrolo[2,1-c][1,4]benzodiazepin-5-one (11g)

To a solution of 4-amino-3-(3,4-dimethoxyphenoxy)phenol (5d) (261 mg, 1 mmol) in acetone (10 mL) was added anhydrous $K_2CO_3$ (552 mg, 4 mmol) and the (S)-(2-amino-4-(5-bromopentyloxy)-5-methoxyphenyl)(2(bis(ethylthio)methyl)pyrrolidin-1-yl)methan one (3c) (518 mg, 1 mmol) The reaction mixture was heated to reflux at 60° C. for 48 hrs. After completion of the reaction as indicated by TLC, potassium carbonate was removed by suction filtration and the solvent was removed under vacuum. The crude product thus obtained was purified by column chromatography using ethyl acetate-hexane (8:2) as eluant to afford pure amino compound (544 mg, 78%).

$^1$H NMR of amino compound:
$^1$H NMR (CDCl$_3$, 300 MHz): δ 1.32-1.37 (m, 6H), 1.61-1.67 (m, 2H), 1.76-1.87 (m, 2H), 1.87-1.98 (m, 2H), 2.04-2.16 (m, 2H), 2.23-2.33 (m, 2H), 2.66-2.87 (m, 4H), 3.18-3.34 (m, 2H), 3.85 (s, 3H), 3.88 (s, 3H), 3.92 (s, 3H), 4.05 (t, 2H, J=6.04 Hz), 4.10 (t, 2H, J=6.04 Hz), 4.66-4.72 (m, 1H), 4.86 (d, 1H, J=3.77 Hz), 5.24 (brs, 2H), 5.27 (brs, 2H), 6.35 (d, 1H, J=2.89 Hz), 6.58-6.61 (m, 2H), 6.65 (d, 1H, J=2.86 Hz), 6.82 (s, 1H), 6.84 (d, 1H, J=8.68 Hz), 7.30 (s, 1H), 7.32 (d, 1H, J=7.63 Hz); ESIMS: m/z 699 (M$^+$).

A solution of amino compound (698 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl₃ (5%) to give compound 11g (322 mg, 56%). This material was repeatedly evaporated from CHCl₃ in vacuum to generate the imine form.

¹H NMR (CDCl₃, 300 MHz): δ 1.54-1.64 (m, 2H), 1.73-1.82 (m, 2H), 1.86-1.96 (m, 2H), 2.02-2.10 (m, 2H), 2.28-2.35 (m, 2H), 3.68-3.82 (m, 3H), 3.83 (s, 3H), 3.86 (s, 3H), 3.92 (s, 3H), 4.06 (t, 4H, J=6.12 Hz), 6.39 (d, 1H, J=3.02 Hz), 6.47-6.54 (m, 2H), 6.64 (d, 1H, J=2.26 Hz), 6.72 (d, 1H, J=9.06 Hz), 6.78 (s, 1H), 6.79 (d, 1H, J=6.79 Hz), 7.50 (s, 1H), 7.67 (d, 1H, J=4.53 Hz); ESIMS: m/z 576 (M⁺+1).

Example 3

7-Methoxy-(8-5-[4-amino-3-(3,4,5-trimethoxyphenoxy)phenoxy]pentyloxy)-(11aS)-1,2,3,11a-tetrahydro-5H-pyrrolo[2,1-c][1,4]benzodiazepin-5-one (12g)

To a solution of 4-amino-3-(3,4,5-trimethoxyphenoxy) phenol (5f) (291 mg, 1 mmol) in acetone (10 mL) was added anhydrous K₂CO₃ (552 mg, 4 mmol) and the (S)-(2-amino-4-(5-bromopentyloxy)-5-methoxyphenyl)(2(bis(ethylthio) methyl)pyrrolidin-1-yl)methan one (3c) (518 mg, 1 mmol) The reaction mixture was heated to reflux at 60° C. for 48 hrs. After completion of the reaction as indicated by TLC, potassium carbonate was removed by suction filtration and the solvent was removed under vacuum. The crude product thus obtained was purified by column chromatography using ethyl acetate-hexane (8:2) as eluant to afford pure amino compound (555 mg, 76%).

¹H NMR (CDCl₃, 300 MHz): δ 1.31-1.39 (m, 6H), 1.60-1.70 (m, 2H), 1.76-2.16 (m, 8H), 2.66-3.03 (m, 4H), 3.15-3.31 (m, 2H), 3.81 (s, 3H), 3.82 (s, 3H), 3.82 (s, 3H), 3.92 (s, 3H), 3.96 (t, 2H, J=6.04 Hz), 4.10 (t, 2H, J=6.06 Hz), 4.66-4.72 (m, 1H), 4.84 (d, 1H, J=3.77 Hz), 5.25 (brs, 2H), 5.30 (brs, 2H), 6.30 (s, 2H), 6.35 (d, 1H, J=2.26 Hz), 6.61 (d, 1H, J=7.06 Hz), 6.80 (s, 1H), 7.29 (s, 1H), 7.35 (d, 1H, J=8.26 Hz); ESIMS: m/z 730 (M⁺+1).

A solution of amino compound (729 mg, 1 mmol), HgCl₂ (613 mg, 2.26 mmol) and CaCO₃ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO₃ (20 mL), brine (20 mL) and the combined organic phase was dried (Na₂SO₄). The organic layer was evaporated under vacuum and purified by column chromatography using MeOH—CHCl₃ (5%) to give compound 12g (357 mg, 59%). This material was repeatedly evaporated from CHCl₃ in vacuum to generate the imine form.

¹H NMR (CDCl₃, 300 MHz): δ 1.52-1.66 (m, 2H), 1.72-1.82 (m, 2H), 1.84-1.95 (m, 2H), 2.00-2.10 (m, 2H), 2.27-2.37 (m, 2H), 3.65-3.76 (m, 3H), 3.78 (s, 6H), 3.80 (s, 3H), 3.85 (s, 3H), 4.05 (t, 4H, J=6.02 Hz), 6.24 (s, 2H), 6.43 (d, 1H, J=2.26 Hz), 6.55 (dd, 1H, J=2.45, 8.49 Hz), 6.79 (s, 1H), 6.82 (d, 1H, J=8.87 Hz), 7.48 (s, 1H), 7.65 (d, 1H, J=4.38 Hz); ESIMS: m/z 606 (M⁺+1).

Example 4

7-Methoxy-(8-3-[3-(4-methoxyphenoxy)-2-nitrophenoxy]pentyloxy)-(11aS)-1,2,3,11a-tetrahydro-5H-pyrrolo[2,1-c][1,4]benzodiazepin-5-one (19g)

To a solution of 3-(4-methoxyphenoxy)-4-nitrophenol (5t) (261 mg, 1 mmol) in acetone (10 mL) was added anhydrous K₂CO₃ (552 mg, 4 mmol) and the (S)-(2-amino-4-(5-bromopentyloxy)-5-methoxyphenyl)(2(bis(ethylthio)methyl) pyrrolidin-1-yl)methanone (3c) (518 mg, 1 mmol) The reaction mixture was heated to reflux at 60° C. for 48 hrs. After completion of the reaction as indicated by TLC, potassium carbonate was removed by suction filtration and the solvent was removed under vacuum. The crude product thus obtained was purified by column chromatography using ethyl acetate-hexane (8:2) as eluant to afford pure amino compound (524 mg, 75%).

¹H NMR (CDCl₃, 300 MHz): δ 1.24-1.27 (t, 3H, J=7.36 Hz), 1.30-1.35 (t, 2H, J=6.79 Hz), 1.54-1.72 (m, 6H), 1.81-1.98 (m, 6H), 2.61-2.79 (m, 4H), 3.51-3.69 (m, 2H), 3.76 (s, 3H), 3.78 (s, 3H), 4.00 (t, 4H, J=6.23 Hz), 4.66-4.70 (m, 1H), 4.86 (d, 1H, J=3.77 Hz), 5.25 (brs, 2H), 6.22 (s, 1H), 6.81 (s, 1H), 6.83-6.88 (m, 3H), 6.91-6.96 (m, 4H), 7.42 (d, 1H, J=3.02 Hz); ESIMS: m/z 700 (M⁺+1).

A solution of amino compound (699 mg, 1 mmol), HgCl₂ (613 mg, 2.26 mmol) and CaCO₃ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO₃ (20 mL), brine (20 mL) and the combined organic phase was dried (Na₂SO₄). The organic layer was evaporated under vacuum and purified by column chromatography using MeOH—CHCl₃ (5%) to give compound 19g (316 mg, 55%). This material was repeatedly evaporated from CHCl₃ in vacuum to generate the imine form.

¹H NMR (CDCl₃, 300 MHz): δ 1.63-1.69 (m, 4H), 1.71-1.80 (m, 2H), 1.83-1.92 (m, 2H), 2.02-2.10 (m, 2H), 3.69-3.81 (m, 3H), 3.82 (s, 3H), 3.92 (s, 3H), 4.05 (t, 4H, J=6.42 Hz), 6.31 (d, 1H, J=2.45 Hz), 6.57 (dd, 1H, J=2.45, 9.06 Hz), 6.78 (s, 1H), 6.91 (d, 2H, J=9.06 Hz), 7.01 (d, 2H, J=9.06 Hz), 7.51 (s, 1H), 7.65 (d, 1H, J=4.34 Hz), 8.04 (d, 1H, J=9.06 Hz); ESIMS: m/z 576 (M⁺+1).

Example 5

7-Methoxy-(8-3-[4-(3,4-dimethoxyphenoxy)-3-nitrophenoxy]pentyloxy)-(11aS)-1,2,3,11a-tetrahydro-5H-pyrrolo[2,1-c][1,4]benzodiazepin-5-one (20c)

To a solution of 4-(3,4-dimethoxyphenoxy)-3-nitrophenol (5u) (291 mg, 1 mmol) in acetone (10 mL) was added anhydrous K₂CO₃ (552 mg, 4 mmol) and the (S)-(2-amino-4-(5-bromopentyloxy)-5-methoxyphenyl)(2(bis(ethylthio)methyl)pyrrolidin-1-yl)methan one (3c) (518 mg, 1 mmol) The reaction mixture was heated to reflux at 60° C. for 48 hrs. After completion of the reaction as indicated by TLC, potassium carbonate was removed by suction filtration and the solvent was removed under vacuum. The crude product thus obtained was purified by column chromatography using ethyl acetate-hexane (8:2) as eluant to afford pure amino compound (568 mg, 78%).

¹H NMR (CDCl₃, 300 MHz): δ 1.25 (t, 3H, J=7.55 Hz), 1.33 (t, 3H, J=7.55 Hz), 1.61-1.72 (m, 4H), 1.84-2.05 (m, 6H), 2.61-2.84 (m, 4H), 3.51-3.71 (m, 2H), 3.75 (s, 3H), 3.84 (s, 3H), 3.85 (s, 3H), 3.97-4.02 (m, 4H), 4.64-4.7 (m, 2H), 5.25 (brs, 2H), 6.19 (s, 1H), 6.44 (dd, 1H, J=3.02, 9.06 Hz), 6.62 (d, 1H, J=3.02 Hz), 6.74 (d, 1H, J=6.04 Hz), 6.79 (s, 1H), 6.95 (d, 1H, J=9.06 Hz), 7.04 (dd, 1H, J=3.02, 9.06 Hz), 7.42 (d, 1H, J=3.02 Hz); ESIMS: m/z 730 (M⁺+1).

A solution of amino compound (729 mg, 1 mmol), HgCl₂ (613 mg, 2.26 mmol) and CaCO₃ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (5%) to give compound 20c (357 mg, 59%). This material was repeatedly evaporated from CHCl$_3$ in vacuum to generate the imine form.

$^1$H NMR (CDCl$_3$, 300 MHz): δ 1.62-1.72 (m, 2H), 1.87-1.98 (m, 4H), 1.99-2.10 (m, 2H), 2.29-2.36 (m, 2H), 3.69-3.79 (m, 3H), 3.84 (s, 3H), 3.86 (s, 3H), 3.93 (s, 3H), 4.03 (t, 4H, J=6.03 Hz), 6.46 (dd, 1H, J=2.26, 9.06 Hz), 6.64 (d, 1H, J=1.51 Hz), 6.81 (d, 2H, J=9.06 Hz), 6.94 (d, 1H, J=9.06 Hz), 7.04 (dd, 1H, J=2.26, 9.06 Hz), 7.43 (d, 1H, J=1.51 Hz), 7.51 (s, 1H), 7.66 (d, 1H, J=4.53 Hz); ESIMS: m/z 606 (M$^+$+1).

Example 6

7-Methoxy-(8-3-[3-(3,4-dimethoxyphenoxy)-2-nitrophenoxy]pentyloxy)-(11aS)-1,2,3,11a-tetrahydro-5H-pyrrolo[2,1-c][1,4]benzodiazepin-5-one (20g)

To a solution of 3-(3,4-dimethoxyphenoxy)-4-nitrophenol (5v) (261 mg, 1 mmol) in acetone (10 mL) was added anhydrous K$_2$CO$_3$ (552 mg, 4 mmol) and the (S)-(2-amino-4-(5-bromopentyloxy)-5-methoxyphenyl)(2(bis(ethylthio)methyl)pyrrolidin-1-yl)methan one (3c) (518 mg, 1 mmol) The reaction mixture was heated to reflux at 60° C. for 48 hrs. After completion of the reaction as indicated by TLC, potassium carbonate was removed by suction filtration and the solvent was removed under vacuum. The crude product thus obtained was purified by column chromatography using ethyl acetate-hexane (8:2) as eluant to afford pure amino compound (576 mg, 75%).

$^1$H NMR (CDCl$_3$, 300 MHz): δ 1.32-1.37 (m, 6H), 1.61-1.67 (m, 2H), 1.76-1.87 (m, 2H), 1.87-1.98 (m, 2H), 2.04-2.16 (m, 2H), 2.23-2.33 (m, 2H), 2.66-2.87 (m, 4H), 3.18-3.34 (m, 2H), 3.85 (s, 3H), 3.88 (s, 3H), 3.92 (s, 3H), 4.05 (t, 2H, J=6.04 Hz), 4.10 (t, 2H, J=6.04 Hz), 4.66-4.72 (m, 1H), 4.86 (d, 1H, J=3.77 Hz), 5.26 (brs, 2H), 6.35 (d, 1H, J=2.89 Hz), 6.58-6.61 (m, 2H), 6.68 (d, 1H, J=2.89 Hz), 6.82 (s, 1H), 6.84 (d, 1H, J=8.68 Hz), 7.29 (s, 1H), 8.02 (d, 1H, J=9.65 Hz); ESIMS: m/z 730 (M$^+$+1).

A solution of amino compound (729 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (5%) to give compound 20g (314 mg, 52%). This material was repeatedly evaporated from CHCl$_3$ in vacuum to generate the imine form.

$^1$H NMR (CDCl$_3$, 300 MHz): δ 1.56-1.68 (m, 2H), 1.74-1.82 (m, 2H), 1.85-1.94 (m, 2H), 2.00-2.10 (m, 2H), 2.29-2.36 (m, 2H), 3.66-3.78 (m, 3H), 3.81 (s, 6H), 3.84 (s, 3H), 3.92 (s, 3H), 4.07 (t, 4H, J=6.79 Hz), 6.33 (s, 2H), 6.40 (d, 1H, J=2.26 Hz), 6.62 (dd, 1H, J=2.26, 9.06 Hz), 6.78 (s, 1H), 7.51 (s, 1H), 7.65 (d, 1H, J=4.53 Hz), 8.04 (d, 1H, J=9.06 Hz); ESIMS: m/z 606 (M$^+$+1).

Example 7

7-Methoxy-(8-3-[4-(3,4,5-timethoxyphenoxy)-3-nitrophenoxy]pentyloxy)-(11aS)-1,2,3,11a-tetrahydro-5H-pyrrolo[2,1-c][1,4]benzodiazepin-5-one (21c)

To a solution of 3-nitro-4-(3,4,5-trimethoxyphenoxy)phenol (5w) (291 mg, 1 mmol) in acetone (10 mL) was added anhydrous K$_2$CO$_3$ (552 mg, 4 mmol) and the (S)-(2-amino-4-(5-bromopentyloxy)-5-methoxyphenyl)(2(bis(ethylthio)methyl)pyrrolidin-1-yl)methan one (3c) (518 mg, 1 mmol) The reaction mixture was heated to reflux at 60° C. for 48 hrs. After completion of the reaction as indicated by TLC, potassium carbonate was removed by suction filtration and the solvent was removed under vacuum. The crude product thus obtained was purified by column chromatography using ethyl acetate-hexane (8:2) as eluant to afford pure amino compound (600 mg, 79%).

$^1$H NMR (CDCl$_3$, 300 MHz): δ 1.24 (t, 3H, J=6.79 Hz), 1.33 (t, 3H, J=6.79 Hz), 1.57-1.76 (m, 4H), 1.82-2.05 (m, 6H), 2.60-2.83 (m, 4H), 3.51-3.71 (m, 2H), 3.77 (s, 3H), 3.78 (s, 6H), 3.81 (s, 3H), 3.99-4.06 (m, 4H), 4.65-4.69 (m, 1H), 4.82 (d, 1H, J=3.77 Hz), 5.24 (brs, 2H), 6.22 (d, 1H, J=6.04 Hz), 6.23 (s, 2H), 6.82 (s, 1H), 7.02 (d, 1H, J=9.06 Hz), 7.07 (dd, 1H, J=3.02, 9.82 Hz), 7.44 (d, 1H, J=2.26 Hz); ESIMS: m/z 760 (M$^+$+1).

A solution of amino compound (759 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (5%) to give compound 21c (381 mg, 60%). This material was repeatedly evaporated from CHCl$_3$ in vacuum to generate the imine form.

δ 1.63-1.78 (m, 4H), 1.84-2.01 (m, 4H), 2.04-2.15 (m, 2H), 3.66-3.73 (m, 3H), 3.74 (s, 3H), 3.79 (s, 6H), 3.81 (s, 3H), 4.06 (t, 4H, J=6.23 Hz), 6.23 (s, 2H), 6.28 (s, 1H), 6.81 (s, 1H), 7.04 (d, 1H, J=9.06 Hz), 7.08 (dd, 1H, J=2.64, 9.06 Hz), 7.51 (s, 1H), 7.65 (d, 1H, J=4.36 Hz); ESIMS: m/z 636 (M$^+$+1).

Example 8

7-Methoxy-(8-3-[3-(3,4,5-trimethoxyphenoxy)-2-nitrophenoxy]pentyloxy)-(11aS)-1,2,3,11a-tetrahydro-5H-pyrrolo[2,1-c][1,4]benzodiazepin-5-one (21g)

To a solution of 4-nitro-3-(3,4,5-trimethoxyphenoxy)phenol (5x) (291 mg, 1 mmol) in acetone (10 mL) was added anhydrous K$_2$CO$_3$ (552 mg, 4 mmol) and the (S)-(2-amino-4-(5-bromopentyloxy)-5-methoxyphenyl)(2(bis(ethylthio)methyl)pyrrolidin-1-yl)methan one (3c) (518 mg, 1 mmol) The reaction mixture was heated to reflux at 60° C. for 48 hrs. After completion of the reaction as indicated by TLC, potassium carbonate was removed by suction filtration and the solvent was removed under vacuum. The crude product thus obtained was purified by column chromatography using ethyl acetate-hexane (8:2) as eluant to afford pure amino compound (607 mg, 80%).

$^1$H NMR (CDCl$_3$, 300 MHz): δ 1.31-1.39 (m, 6H), 1.60-1.70 (m, 2H), 1.76-2.16 (m, 8H), 2.66-3.03 (m, 4H), 3.15-

3.31 (m, 2H), 3.81 (s, 3H), 3.82 (s, 3H), 3.82 (s, 3H), 3.92 (s, 3H), 3.96 (t, 2H, J=6.04 Hz), 4.10 (t, 2H, J=6.04 Hz), 4.66-4.72 (m, 1H), 4.84 (d, 1H, J=3.77 Hz), 5.25 (brs, 2H), 6.30 (s, 2H), 6.39 (d, 1H, J=2.26 Hz), 6.61 (dd, 1H, J=2.26, 9.06 Hz), 6.80 (s, 1H), 7.28 (s, 1H), 8.02 (d, 1H, J=9.06 Hz); ESIMS: m/z 760 (M$^+$+1).

A solution of amino compound (759 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (5%) to give compound 21g (342 mg, 54%). This material was repeatedly evaporated from CHCl$_3$ in vacuum to generate the imine form.

$^1$H NMR (CDCl$_3$, 300 MHz): δ 1.56-1.68 (m, 2H), 1.74-1.82 (m, 2H), 1.85-1.94 (m, 2H), 2.00-2.10 (m, 2H), 2.29-2.36 (m, 2H), 3.66-3.78 (m, 3H), 3.81 (s, 6H), 3.84 (s, 3H), 3.92 (s, 3H), 4.07 (t, 4H, J=6.79 Hz), 6.33 (s, 2H), 6.40 (d, 1H, J=2.26 Hz), 6.62 (dd, 1H, J=2.26, 9.06 Hz), 6.78 (s, 1H), 7.51 (s, 1H), 7.65 (d, 1H, J=4.53 Hz), 8.04 (d, 1H, J=9.06 Hz); ESIMS: m/z 636 (M$^+$+1).

Example 9

7-Methoxy-(8-(3-4-[3-amino-4-(4-methoxyphenoxy)benzoyl]piperazinopentyloxy)-(11aS)-1,2,3,11a-tetrahydro-5H-pyrrolo[2,1-c][1,4]benzodiazepin-5-one (22c)

To a solution of (3-amino-4-(4-methoxyphenoxy)phenyl)(piperazin-1-yl)methanone (7a) (327 mg, 1 mmol) in acetone (10 mL) was added anhydrous K$_2$CO$_3$ (552 mg, 4 mmol) and the (S)-(2-amino-4-(5-bromopentyloxy)-5-methoxyphenyl)(2(bis(ethylthio)methyl)pyrrolidin-1-yl)methanone (3c) (518 mg, 1 mmol). The reaction mixture was heated to reflux at 60° C. for 48 hrs. After completion of the reaction as indicated by TLC, potassium carbonate was removed by suction filtration and the solvent was removed under vacuum. The crude product thus obtained was purified by column chromatography using ethyl acetate-hexane (8:2) as eluant to afford pure amino compound (596 mg, 75%).

$^1$H NMR (CDCl$_3$, 300 MHz): δ 1.31-1.38 (m, 6H), 1.47-1.66 (m, 4H), 1.74-1.99 (m, 4H), 2.07-2.16 (m, 2H), 2.40-2.47 (m, 2H), 2.48-2.58 (brs, 4H), 2.66-2.86 (m, 4H), 3.31-3.34 (m, 2H), 3.44-3.79 (brs, 4H), 3.89 (s, 3H), 3.92 (s, 3H), 4.09 (t, 2H, J=6.04 Hz), 4.67-4.76 (m, 1H), 4.87 (d, 1H, J=3.77 Hz), 5.24 (brs, 2H), 5.28 (brs, 2H), 6.63 (d, 1H, J=2.06 Hz), 6.68 (d, 2H, J=2.26 Hz), 6.82 (s, 1H), 6.89 (d, 1H, J=9.06 Hz), 6.94 (d, 1H, J=9.06 Hz), 7.27 (s, 1H), 7.35 (d, 1H, J=2.29 Hz), 7.48 (d, 1H, J=9.06 Hz); ESIMS: m/z 766 (M$^+$+1).

A solution of amino compound (765 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (5%) to give compound 22c (378 mg, 59%). This material was repeatedly evaporated from CHCl$_3$ in vacuum to generate the imine form.

$^1$H NMR (CDCl$_3$, 300 MHz): δ 1.34-1.60 (m, 4H), 1.73-1.86 (m, 2H), 1.92-1.98 (brs, 4H), 1.99-2.12 (m, 2H), 2.24-2.33 (m, 2H), 2.36-2.41 (m, 2H), 2.43-2.57 (brs, 4H), 3.42-3.72 (m, 3H), 3.80 (s, 3H), 3.93 (s, 3H), 4.05 (t, 2H, J=6.79 Hz), 6.68 (s, 2H), 6.79 (s, 1H), 6.85 (d, 3H, J=9.82 Hz), 6.94 (d, 2H, J=9.06 Hz), 7.51 (s, 1H), 7.66 (d, 1H, J=4.53 Hz); ESIMS: m/z 642 (M$^+$+1).

Example 10

7-Methoxy-(8-(3-4-[3-amino-4-(3,4-dimethoxyphenoxy)benzoyl]piperazinopentyloxy)-(11aS)-1,2,3, 11a-tetrahydro-5H-pyrrolo[2,1-c][1,4]benzodiazepin-5-one (23c)

To a solution of (3-amino-4-(3,4-dimethoxyphenoxy)phenyl)(piperazin-1-yl)methanone (7b) (357 mg, 1 mmol) in acetone (10 mL) was added anhydrous K$_2$CO$_3$ (552 mg, 4 mmol) and the(S)-(2-amino-4-(5-bromopentyloxy)-5-methoxyphenyl)(2(bis(ethylthio)methyl)pyrrolidin-1-yl)methanone (3c) (518 mg, 1 mmol). The reaction mixture was heated to reflux at 60° C. for 48 hrs. After completion of the reaction as indicated by TLC, potassium carbonate was removed by suction filtration and the solvent was removed under vacuum. The crude product thus obtained was purified by column chromatography using ethyl acetate-hexane (8:2) as eluant to afford pure amino compound (612 mg, 75%).

$^1$H NMR (CDCl$_3$, 300 MHz): δ 1.31-1.38 (m, 6H), 1.47-1.66 (m, 4H), 1.74-1.99 (m, 4H), 2.07-2.16 (m, 2H), 2.40-2.47 (m, 2H), 2.48-2.58 (brs, 4H), 2.66-2.86 (m, 4H), 3.31-3.34 (m, 2H), 3.44-3.79 (brs, 4H), 3.86 (s, 3H), 3.90 (s, 3H), 3.94 (s, 3H), 4.09 (t, 2H, J=6.04 Hz), 4.67-4.76 (m, 1H), 4.87 (d, 1H, J=3.77 Hz), 5.24 (brs, 2H), 5.29 (brs, 2H), 6.63 (dd, 1H, J=2.26, 9.06 Hz), 6.68 (d, 1H, J=2.26 Hz), 6.82 (s, 1H), 6.88 (d, 1H, J=9.06 Hz), 6.94 (d, 1H, J=9.06 Hz), 7.27 (s, 1H), 7.35 (d, 1H, J=2.29 Hz), 7.52 (dd, 1H, J=2.26, 9.06 Hz); ESIMS: m/z 796 (M$^+$+1).

A solution of amino compound (795 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (5%) to give compound 23c (348 mg, 52%). This material was repeatedly evaporated from CHCl$_3$ in vacuum to generate the imine form.

$^1$H NMR (CDCl$_3$, 300 MHz): δ 1.46-1.56 (m, 2H), 1.57-1.69 (m, 2H), 1.71-1.84 (brs, 4H), 1.85-1.95 (m, 2H), 1.98-2.10 (m, 2H), 2.25-2.36 (m, 2H), 2.41-2.66 (brs, 4H), 3.46-3.75 (m, 3H), 3.84 (s, 3H), 3.87 (s, 3H), 3.93 (s, 3H), 4.06 (t, 2H, J=6.42 Hz), 6.54 (dd, 1H, J=2.45, 8.49 Hz), 6.64 (d, 1H, J=2.45 Hz), 6.69 (s, 1H), 6.72 (d, 1H, J=8.30 Hz), 6.79 (s, 1H), 6.84 (d, 1H, J=9.63 Hz), 7.28 (s, 1H), 7.51 (s, 1H), 7.67 (d, 1H, J=4.34 Hz);
ESIMS: m/z 672 (M$^+$+1).

Example 11

7-Methoxy-(8-(3-4-[3-amino-4-(3,4,5-trimethoxyphenoxy)benzoyl]piperazinopentyloxy)-(11aS)-1,2,3,11a-tetrahydro-5H-pyrrolo[2,1-c][1,4]benzodiazepin-5-one (24c)

To a solution of (3-amino-4-(3,4,5-trimethoxyphenoxy)phenyl)(piperazin-1-yl)methanone (7c) (387 mg, 1 mmol) in acetone (10 mL) was added anhydrous $K_2CO_3$ (552 mg, 4 mmol) and the (S)-(2-amino-4-(5-bromopentyloxy)-5-methoxyphenyl)(2(bis(ethylthio)methyl)pyrrolidin-1-yl)methanone (3c) (518 mg, 1 mmol). The reaction mixture was heated to reflux at 60° C. for 48 hrs. After completion of the reaction as indicated by TLC, potassium carbonate was removed by suction filtration and the solvent was removed under vacuum. The crude product thus obtained was purified by column chromatography using ethyl acetate-hexane (8:2) as eluant to afford pure amino compound (643 mg, 78%).

$^1$H NMR (CDCl$_3$, 300 MHz): δ 1.31-1.37 (m, 6H), 1.47-1.65 (m, 4H), 1.75-1.98 (m, 4H), 2.08-2.16 (m, 2H), 2.40-2.47 (m, 2H), 2.48-2.57 (brs, 4H), 2.66-2.86 (m, 4H), 3.33-3.35 (m, 2H), 3.45-3.79 (brs, 4H), 3.81 (s, 6H), 3.83 (s, 3H), 3.93 (s, 3H), 4.12 (t, 2H, J=6.04 Hz), 4.63-4.73 (m, 1H), 4.84 (d, 1H, J=3.77 Hz), 5.24 (brs, 2H), 5.29 (brs, 2H), 6.33 (s, 2H), 6.80 (s, 1H), 7.00 (d, 1H, J=9.06 Hz), 7.54 (dd, 1H, J=2.26, 9.06 Hz), 7.33 (s, 1H), 7.54 (s, 1H); ESIMS: m/z 826 (M$^+$+1).

A solution of amino compound (825 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (5%) to give compound 24c (371 mg, 53%). This material was repeatedly evaporated from CHCl$_3$ in vacuum to generate the imine form.

$^1$H NMR (CDCl$_3$, 300 MHz): δ 1.47-1.64 (m, 2H), 1.70-1.83 (brs, 4H), 1.85-1.96 (m, 2H), 1.98-2.12 (m, 2H), 2.27-2.34 (m, 2H), 2.36-2.43 (m, 2H), 2.44-2.57 (brs, 4H), 3.46-3.65 (s, 3H), 3.79 (s, 6H), 3.82 (s, 3H), 3.93 (s, 3H), 4.07 (t, 2H, J=6.42 Hz), 6.26 (s, 2H), 6.72 (d, 1H, J=8.30 Hz), 6.79 (d, 2H, J=8.87 Hz), 6.87 (s, 1H), 7.51 (s, 1H), 7.66 (d, 1H, J=3.96 Hz); ESIMS: m/z 702 (M$^+$+1).

Example 12

7-Methoxy-(8-(3-4-[4-(4-methoxyphenoxy)-3-nitrobenzoyl]piperazinopentyloxy)-(11aS)-1,2,3,11a-tetrahydro-5H-pyrrolo[2,1-c][1,4]benzodiazepin-5-one (31c)

To a solution of (4-(4-methoxyphenoxy)-3-nitrophenyl)(piperazin-1-yl)methanone (7j) (357 mg, 1 mmol) in acetone (10 mL) was added anhydrous $K_2CO_3$ (552 mg, 4 mmol) and the (S)-(2-amino-4-(5-bromopentyloxy)-5-methoxyphenyl) (2(bis(ethylthio)methyl)pyrrolidin-1-yl)methanone (3c) (518 mg, 1 mmol) The reaction mixture was heated to reflux at 60° C. for 48 hrs. After completion of the reaction as indicated by TLC, potassium carbonate was removed by suction filtration and the solvent was removed under vacuum. The crude product thus obtained was purified by column chromatography using ethyl acetate-hexane (8:2) as eluant to afford pure amino compound (596 mg, 75%).

$^1$H NMR (CDCl$_3$, 300 MHz): δ 1.31-1.38 (m, 6H), 1.47-1.66 (m, 4H), 1.74-1.99 (m, 4H), 2.07-2.16 (m, 2H), 2.40-2.47 (m, 2H), 2.48-2.58 (brs, 4H), 2.66-2.86 (m, 4H), 3.31-3.34 (m, 2H), 3.44-3.79 (brs, 4H), 3.89 (s, 3H), 3.92 (s, 3H), 4.09 (t, 2H, J=6.04 Hz), 4.67-4.76 (m, 1H), 4.87 (d, 1H, J=3.77 Hz), 5.24 (brs, 2H), 6.63 (d, 1H, J=2.06 Hz), 6.68 (d, 2H, J=2.26 Hz), 6.82 (s, 1H), 6.89 (d, 1H, J=9.06 Hz), 6.94 (d, 1H, J=9.06 Hz), 7.28 (s, 1H), 7.45 (d, 1H, J=2.06 Hz), 7.35 (d, 1H, J=9.06 Hz); ESIMS: m/z 796 (M$^+$+1).

A solution of amino compound (795 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (5%) to give compound 31c (402 mg, 60%). This material was repeatedly evaporated from CHCl$_3$ in vacuum to generate the imine form.

$^1$H NMR (CDCl$_3$, 300 MHz): δ 1.35-1.60 (m, 4H), 1.79-1.92 (m, 2H), 1.93-1.98 (brs, 4H), 2.02-2.10 (m, 2H), 2.29-2.35 (m, 2H), 2.36-2.44 (m, 2H), 2.45-2.50 (brs, 4H), 3.53-3.74 (m, 3H), 3.82 (s, 3H), 3.93 (s, 3H), 4.06 (t, 2H, J=6.04 Hz), 6.79 (s, 1H), 6.90 (d, 1H, J=4.53 Hz), 6.93 (d, 2H, J=5.28 Hz), 7.03 (d, 2H, J=9.06 Hz), 7.51 (s, 1H), 7.52 (dd, 1H, J=2.26, 7.55 Hz), 7.66 (d, 1H, J=4.53 Hz), 7.99 (d, 1H, J=1.51 Hz); ESIMS: m/z 672 (M$^+$+1).

Example 13

7-Methoxy-(8-(3-4-[4-(3,4-dimethoxyphenoxy)-3-nitrobenzoyl]piperazinopentyloxy)-(11aS)-1,2,3,11a-tetrahydro-5H-pyrrolo[2,1-c][1,4]benzodiazepin-5-one (32c)

To a solution of (4-(3,4-dimethoxyphenoxy)-3-nitrophenyl)(piperazin-1-yl)methanone (7k) (387 mg, 1 mmol) in acetone (10 mL) was added anhydrous $K_2CO_3$ (552 mg, 4 mmol) and the(S)-(2-amino-4-(5-bromopentyloxy)-5-methoxyphenyl)(2(bis(ethylthio)methyl)pyrrolidin-1-yl)methanone (3c) (518 mg, 1 mmol). The reaction mixture was heated to reflux at 60° C. for 48 hrs. After completion of the reaction as indicated by TLC, potassium carbonate was removed by suction filtration and the solvent was removed under vacuum. The crude product thus obtained was purified by column chromatography using ethyl acetate-hexane (8:2) as eluant to afford pure amino compound (627 mg, 76%).

$^1$H NMR (CDCl$_3$, 300 MHz): δ 1.31-1.38 (m, 6H), 1.47-1.66 (m, 4H), 1.74-1.99 (m, 4H), 2.07-2.16 (m, 2H), 2.40-2.47 (m, 2H), 2.48-2.58 (brs, 4H), 2.66-2.86 (m, 4H), 3.31-3.34 (m, 2H), 3.44-3.79 (brs, 4H), 3.86 (s, 3H), 3.90 (s, 3H), 3.94 (s, 3H), 4.09 (t, 2H, J=6.04 Hz), 4.67-4.76 (m, 1H), 4.87 (d, 1H, J=3.77 Hz), 5.24 (brs, 2H), 6.63 (dd, 1H, J=2.26, 9.06 Hz), 6.68 (d, 1H, J=2.26 Hz), 6.82 (s, 1H), 6.89 (d, 1H, J=9.06 Hz), 6.96 (d, 1H, J=9.06 Hz), 7.28 (s, 1H), 7.52 (dd, 1H, J=2.26, 9.06 Hz), 8.00 (d, 1H, J=2.26 Hz);

ESIMS: m/z 826 (M$^+$+1).

A solution of amino compound (825 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (5%) to give compound 32c (357 mg, 51%). This material was repeatedly evaporated from CHCl$_3$ in vacuum to generate the imine form.

$^1$H NMR (CDCl$_3$, 300 MHz): δ 1.45-1.65 m, 4H), 1.85-1.94 (m, 2H), 1.95-2.00 (brs, 4H), 2.05-2.12 (m, 2H), 2.26-2.34 (m, 2H), 2.36-2.43 (m, 2H), 2.44-2.47 (brs, 4H), 3.51-3.78 (m, 3H), 3.86 (s, 3H), 3.90 (s, 3H), 3.93 (s, 3H), 4.07 (t, 2H, J=6.23 Hz), 6.65 (dd, 1H, J=2.83, 8.68 Hz), 6.68 (d, 1H, J=2.64 Hz), 6.79 (s, 1H), 6.86 (d, 1H, J=8.68 Hz), 6.96 (d, 1H, J=8.68 Hz), 7.51 (s, 1H), 7.54 (dd, 1H, J=2.07, 8.68 Hz), 7.67 (d, 1H, J=4.53 Hz), 8.00 (d, 1H, J=2.07 Hz); ESIMS: m/z 702 (M$^+$+1).

Example 14

7-Methoxy-(8-(3-4-[4-(3,4,5-trimethoxyphenoxy)-3-nitrobenzoyl]piperazinopentyloxy)-(11aS)-1,2,3,11a-tetrahydro-5H-pyrrolo[2,1-c][1,4]benzodiazepin-5-one (33c)

To a solution of (3-nitro-4-(3,4,5-trimethoxyphenoxy)phenyl)(piperazin-1-yl)methanone (71) (417 mg, 1 mmol) in acetone (10 mL) was added anhydrous K$_2$CO$_3$ (552 mg, 4 mmol) and the(S)-(2-amino-4-(5-bromopentyloxy)-5-methoxyphenyl)(2(bis(ethylthio)methyl)pyrrolidin-1-yl)methanone (3c) (518 mg, 1 mmol). The reaction mixture was heated to reflux at 60° C. for 48 hrs. After completion of the reaction as indicated by TLC, potassium carbonate was removed by suction filtration and the solvent was removed under vacuum. The crude product thus obtained was purified by column chromatography using ethyl acetate-hexane (8:2) as eluant to afford pure amino compound (641 mg, 75%).

$^1$H NMR (CDCl$_3$, 300 MHz): δ 1.31-1.37 (m, 6H), 1.47-1.65 (m, 4H), 1.75-1.98 (m, 4H), 2.08-2.16 (m, 2H), 2.40-2.47 (m, 2H), 2.48-2.57 (brs, 4H), 2.66-2.86 (m, 4H), 3.33-3.35 (m, 2H), 3.45-3.79 (brs, 4H), 3.81 (s, 6H), 3.83 (s, 3H), 3.93 (s, 3H), 4.12 (t, 2H, J=6.04 Hz), 4.63-4.73 (m, 1H), 4.84 (d, 1H, J=3.77 Hz), 5.24 (brs, 2H), 6.33 (s, 2H), 6.80 (s, 1H), 7.00 (d, 1H, J=9.06 Hz), 7.54 (dd, 1H, J=2.26, 9.06 Hz), 7.33 (s, 1H), 8.03 (s, 1H); ESIMS: m/z 856 (M$^+$+1).

A solution of amino compound (855 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (5%) to give compound 33c (423 mg, 58%). This material was repeatedly evaporated from CHCl$_3$ in vacuum to generate the imine form.

$^1$H NMR (CDCl$_3$, 300 MHz): δ 1.46-1.63 (m, 2H), 1.70-1.82 (brs, 4H), 1.85-1.96 (m, 2H), 1.99-2.10 (m, 2H), 2.29-2.31 (m, 2H), 2.34-2.41 (m, 2H), 2.42-2.51 (brs, 4H), 3.47-3.58 (m, 3H), 3.78 (s, 6H), 3.82 (s, 3H), 3.92 (s, 3H), 4.06 (t, 2H, J=6.23 Hz), 6.25 (s, 2H), 6.68 (d, 1H, J=3.11 Hz), 6.81 (s, 1H), 7.51 (s, 1H), 7.53 (d, 1H, J=8.06 Hz), 7.66 (d, 1H, J=4.34 Hz), 7.79 (d, 1H, J=2.34 Hz); ESIMS: m/z 732 (M$^+$+1).

Biological Activity
DNA Binding Affinity of Diaryl Ether Linked PBD Hybrids: Compounds have been subjected to thermal denaturation studies with duplex-form calf thymus DNA (CT-DNA) using a modification of a reported procedure (Newman, M. S. *Carcinog-compr. Surv.* 1976, 1, 203; (b) Hecht, S. S.; Loy, M.; Hoffman, *Carcinog-compr. Surv.* 1976, 1, 325). Working solutions in aqueous buffer (10 mM NaH$_2$PO$_4$/Na$_2$HPO$_4$, 1 mM Na$_2$EDTA, pH 7.00+0.01) containing CT-DNA (100 μm in phosphate) and the PBD (20 μm) have been prepared by addition of concentrated PBD solutions in DMSO to obtain a fixed [PBD]/[DNA] molar ratio of 1:5. The DNA-PBD solutions have been incubated at 37° C. for 0 and 18 h prior to analysis. Samples have been monitored at 260 nm using a Beckman DU-800 spectrophotometer fitted with high performance temperature controller, and heated at 1° C. min$^1$ in the 40-110° C. range. DNA helix→coil transition temperatures (T$_m$) have been obtained from the maxima in the d(A$_{260}$)/dT derivative plots. Drug-induced alterations in DNA melting behavior are given by: ΔT$_m$=T$_m$(DNA+PBD)−T$_m$(DNA alone), where the T$_m$ value for the PBD-free CT-DNA is 69.1±0.01. The fixed [PBD]/[DNA] ratio used has not resulted in binding saturation of the host DNA duplex for any compound examined.

The DNA binding activity for these novel C8-linked diaryl ether PBD hybrids has been examined by thermal denaturation studies using calf thymus (CT) DNA. Melting studies show that these compounds stabilize the thermal helix→coil or melting stabilization (ΔT$_m$) (ΔT$_m$=T$_m$(DNA+PBD)−T$_m$ (DNA alone)) for the CT-DNA duplex at pH 7.0, incubated at 37° C., where PBD/DNA molar ratio is 1:5. The data for the compounds are included in Table 1 for comparison.

TABLE 1

Thermal denaturation data for diaryl ether linked PBD hybrids with calf thymus (CT) DNA at a molar ratio of 1:5 in aqueous sodium phosphate buffer at pH 7 and having the following thermal denaturation data:

| PBD hybrids | [PBD]:[DNA] molar ratio$^b$ | (ΔT$_m$ ° C.)$^a$ after incubation at 37° C. for | |
|---|---|---|---|
| | | 0 h | 18 h |
| 10g | 1:5 | 2.9 | 3.6 |
| 11g | 1:5 | 4.1 | 5.5 |
| 12g | 1:5 | 4.2 | 5.1 |
| 16c | 1:5 | 3.6 | 4.6 |
| 17c | 1:5 | 3.9 | 4.8 |
| 17g | 1:5 | 4.3 | 5.1 |
| 18c | 1:5 | 4.6 | 5.5 |
| 19g | 1:5 | 4.9 | 5.8 |
| 20c | 1:5 | 4.9 | 5.6 |
| 20g | 1:5 | 4.5 | 6.0 |
| 21c | 1:5 | 3.9 | 5.1 |
| 21g | 1:5 | 4.9 | 6.2 |
| 22c | 1:5 | 3.1 | 4.2 |
| 23c | 1:5 | 3.6 | 4.5 |
| 24c | 1:5 | 4.5 | 6.0 |
| 31c | 1:5 | 3.9 | 5.6 |
| 32c | 1:5 | 4.8 | 7.3 |
| 33c | 1:5 | 4.2 | 6.1 |
| DC-81 | 1:5 | 0.3 | 0.7 |
| 5b | 1:5 | 0.1 | 0.2 |
| 7b | 1:5 | 0.2 | 0.5 |

$^a$For CT-DNA alone at pH 7.00 ± 0.01, T$_m$ = 69.1° C. ± 0.01 (mean value from 10 separate determinations), all ΔT$_m$ values are ± 0.1–0.2° C.
$^b$For a 1:5 molar ratio of [PBD]/[DNA], where CT-DNA concentration = 100 μM and ligand concentration = 20 μM in aqueous sodium phosphate buffer [10 mM sodium phosphate + 1 mM EDTA, pH 7.00 ± 0.01].

Anticancer Activity

Some of the C8-linked diaryl ether-PBD hybrids have been tested against eleven human tumour cell lines derived from seven cancer types (lung cancer, colon cancer, cervix, ovarian cancer, oral cancer, prostate cancer and breast cancer) as per Tata protocol as shown in Table 2. For each compound, dose response curves for each cell line were measured at a minimum of five concentrations at 10 fold dilutions. A protocol of 48 h continuous drug exposure was used and a MTT assay was used to estimate cell viability or growth. The percent of cell growth (GI$_{50}$) compared with the control was calculated. Some of the compounds have been evaluated for their in vitro cytotoxicity in eleven cell lines from seven human cancer types. The results are expressed as GI$_{50}$ determined relative to that of untreated control cells (Table-2).

TABLE 2

GI$_{50}$ (concentration in μM) values for the representative compounds against human tumour cell lines.

| S. no | ZR-751[a] | A549[b] | A2780[c] | Hop62[b] | KB[d] | SiHa[e] | Gurav[d] | MCF7[a] | Colo205[f] | DWD[d] | PC3[g] |
|---|---|---|---|---|---|---|---|---|---|---|---|
| 10g | 3.10 | 2.84 | 2.30 | 2.10 | 2.12 | 1.56 | 2.43 | 2.30 | 1.50 | 2.40 | 2.84 |
| 11g | 2.50 | 2.01 | 0.17 | 2.43 | 0.17 | 1.99 | 0.16 | 0.16 | 0.17 | 0.18 | 2.25 |
| 12g | 2.10 | 0.19 | 0.17 | 2.86 | 0.17 | 2.86 | 0.17 | 0.16 | 0.16 | 0.17 | 2.19 |
| 16c | 3.30 | 2.70 | 2.30 | 1.50 | 2.32 | 1.42 | 2.23 | 2.10 | 2.22 | 2.60 | 2.12 |
| 17c | 3.80 | 2.45 | 2.80 | 1.12 | 2.16 | 2.35 | 2.27 | 2.60 | 2.26 | 2.70 | 2.56 |
| 17g | 1.95 | 1.65 | 0.18 | 2.25 | 1.62 | 0.19 | 0.19 | <0.1 | 2.20 | 0.18 | 0.17 |
| 18c | 2.78 | 3.04 | 3.10 | 2.01 | 2.65 | 2.22 | 2.68 | 3.60 | 3.12 | 3.00 | 2.57 |
| 19g | 2.50 | 2.22 | 2.30 | 2.50 | 0.17 | 1.62 | 2.26 | 2.00 | 0.17 | 2.30 | 2.84 |
| 20c | 0.13 | 0.15 | 0.14 | 0.14 | 0.15 | 2.47 | 1.24 | 0.14 | 0.13 | 0.13 | 0.16 |
| 20g | 0.19 | 0.19 | 2.00 | 0.19 | 0.17 | 2.50 | 0.16 | 2.10 | 0.17 | 0.18 | 2.25 |
| 21c | 1.60 | 2.50 | 1.56 | 3.10 | 3.15 | 1.26 | 2.86 | 1.85 | 2.51 | 2.13 | 1.58 |
| 21g | 0.18 | 2.02 | 2.10 | 2.13 | 0.16 | 2.21 | 0.16 | 2.30 | 0.17 | 0.17 | 0.19 |
| 22c | 0.19 | 0.18 | 0.19 | 2.30 | 0.16 | 3.25 | 0.16 | 0.17 | 0.17 | 0.18 | 0.19 |
| 23c | 0.19 | 0.18 | 0.18 | 2.28 | <0.1 | 2.47 | 0.12 | 0.15 | 0.16 | 0.15 | 0.17 |
| 24c | 0.18 | 0.17 | 2.00 | 2.26 | 0.15 | 2.50 | 0.15 | 0.17 | 0.54 | 0.16 | 0.17 |
| 31c | 0.18 | 0.17 | 0.19 | 0.19 | 0.15 | 3.88 | 0.16 | 0.18 | 0.17 | 0.18 | 0.17 |
| 32c | 0.15 | 0.14 | 0.15 | 0.18 | 0.13 | 1.85 | 0.12 | 0.17 | 0.16 | 0.14 | 0.19 |
| 33c | 2.20 | 2.24 | 2.30 | 2.67 | 0.18 | 2.25 | 0.17 | 0.18 | 0.15 | 2.10 | 2.15 |
| DC-81 | 0.16 | 0.16 | 0.15 | 0.17 | 2.37 | 0.14 | 1.49 | 0.17 | 0.11 | 0.20 | 0.17 |
| ADR | 0.11 | <0.1 | <0.1 | 0.15 | 0.13 | 0.16 | <0.1 | 0.13 | <0.1 | 0.12 | 0.16 |
| 5b | nt | >50 | nt | nt | nt | nt | nt | >50 | >50 | nt | nt |
| 7b | nt | >50 | nt | nt | nt | nt | nt | >50 | >50 | nt | nt |

Where DC-81 is pyrrolo[2,1-c][1,4]benzodiazepine, ADR is adriamycin, 5b is 3-amino-4-(3,4-dimethoxyphenoxy)phenol, 7b is [3-amino-4-(3,4-dimethoxyphenoxy)phenyl](piperazino)methanone.
[a]is breast cancer cell line,
[b]is lung cancer cell,
[c]is ovarian cancer cell line,
[d]is oral cancer cell line,
[e]is Cervix cancer cell lines,
[f]is colon cancer cell line,
[g]is prostrate cancer cell line
nt is not tested

Advantages of the Invention

DNA alkylating agents have been widely used in cancer chemotherapy. These agents have several drawbacks including a lack of drug-specific affinity towards tumor cells. To overcome this problem, in the present invention the alkylating agents coupled with DNA minor groove binders. More over the thermal denaturation study reveals that conjugates are more effective than their individual motifs.

We claim:

1. A compound of formula A:

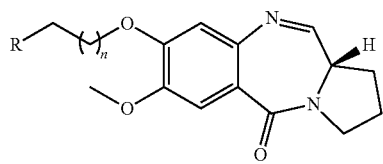

formula A wherein n is an integer of from 2 to 5;
R is selected from the group consisting of:

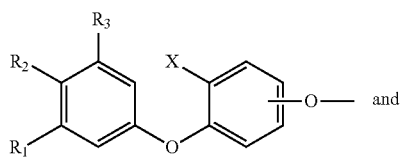

and

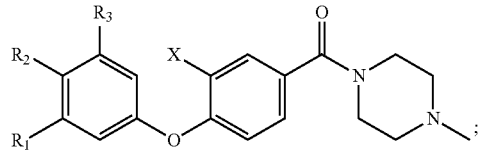

$R_1$, $R_2$, and $R_3$ are independently selected from the group consisting of H and OMe; and
X is selected from the group consisting of $NO_2$, $NH_2$, F and I.

2. The compound of claim 1, selected from the group consisting of:
7-Methoxy-(8-3-[3-amino-4-(4-methoxyphenoxy)phenoxy]propoxy)-(11aS)-1,2,3,11a-tetrahydro-5H-pyrrolo[2,1-c][1,4]benzodiazepin-5-one;
7-Methoxy-(8-4-[3-amino-4-(4-methoxyphenoxy)phenoxy]butoxy)-(11aS)-1,2,3,11a-tetrahydro-5H-pyrrolo[2,1-c][1,4]benzodiazepin-5-one;
7-Methoxy-(8-(5-[3-amino-4-(4-methoxyphenoxy)phenoxy]pentyloxy)-(11aS)-1,2,3,11a-tetrahydro-5H-pyrrolo[2,1-c][1,4]benzodiazepin-5-one;
7-Methoxy-(8-(6-[3-amino-4-(4-methoxyphenoxy)phenoxy]hexyloxy)-(11aS)-1,2,3,11a-tetrahydro-5H-pyrrolo[2,1-c][1,4]benzodiazepin-5-one;
7-Methoxy-(8-3-[4-amino-3-(4-methoxyphenoxy)phenoxy]propoxy)-(11aS)-1,2,3,11a-tetrahydro-5H-pyrrolo[2,1-c][1,4]benzodiazepin-5-one;
7-Methoxy-(8-4-[4-amino-3-(4-methoxyphenoxy)phenoxy]butoxy)-(11aS)-1,2,3,11a-tetrahydro-5H-pyrrolo[2,1-c][1,4]benzodiazepin-5-one;
7-Methoxy-(8-5-[4-amino-3-(4-methoxyphenoxy)phenoxy]pentyloxy)-(11aS)-1,2,3,11a-tetrahydro-5H-pyrrolo[2,1-c][1,4]benzodiazepin-5-one;

7-Methoxy-(8-6-[4-amino-3-(4-methoxyphenoxy)phenoxy]hexyloxy)-(11aS)-1,2,3,11a-tetrahydro-5H-pyrrolo[2,1-c][1,4]benzodiazepin-5-one;

7-Methoxy-(8-3-[3-amino-4-(3,4-dimethoxyphenoxy)phenoxy]propoxy)-(11aS)-1,2,3,11a-tetrahydro-5H-pyrrolo[2,1-c][1,4]benzodiazepin-5-one;

7-Methoxy-(8-4-[3-amino-4-(3,4-dimethoxyphenoxy)phenoxy]butoxy)-(11aS)-1,2,3,11a-tetrahydro-5H-pyrrolo[2,1-c][1,4]benzodiazepin-5-one;

7-Methoxy-(8-(5-[3-amino-4-(3,4-dimethoxyphenoxy)phenoxy]pentyloxy)-(11aS)-1,2,3,11a-tetrahydro-5H-pyrrolo[2,1-c][1,4]benzodiazepin-5-one;

7-Methoxy-(8-(6-[3-amino-4-(3,4-dimethoxyphenoxy)phenoxy]hexyloxy)-(11aS)-1,2,3,11a-tetrahydro-5H-pyrrolo[2,1-c][1,4]benzodiazepin-5-one;

7-Methoxy-(8-3-[4-amino-3-(3,4-dimethoxyphenoxy)phenoxy]propoxy)-(11aS)-1,2,3,11a-tetrahydro-5H-pyrrolo[2,1-c][1,4]benzodiazepin-5-one;

7-Methoxy-(8-4-[4-amino-3-(3,4-dimethoxyphenoxy)phenoxy]butoxy)-(11aS)-1,2,3,11a-tetrahydro-5H-pyrrolo[2,1-c][1,4]benzodiazepin-5-one;

7-Methoxy-(8-5-[4-amino-3-(3,4-dimethoxyphenoxy)phenoxy]pentyloxy)-(11aS)-1,2,3,11a-tetrahydro-5H-pyrrolo[2,1-c][1,4]benzodiazepin-5-one;

7-Methoxy-(8-6-[4-amino-3-(3,4-dimethoxyphenoxy)phenoxy]hexyloxy)-(11aS)-1,2,3,11a-tetrahydro-5H-pyrrolo[2,1-c][1,4]benzodiazepin-5-one;

7-Methoxy-(8-3-[3-amino-4-(3,4,5-trimethoxyphenoxy)phenoxy]propoxy)-(11aS)-1,2,3,11a-tetrahydro-5H-pyrrolo[2,1-c][1,4]benzodiazepin-5-one;

7-Methoxy-(8-4-[3-amino-4-(3,4,5-trimethoxyphenoxy)phenoxy]butoxy)-(11aS)-1,2,3,11a-tetrahydro-5H-pyrrolo[2,1-c][1,4]benzodiazepin-5-one;

7-Methoxy-(8-(5-[3-amino-4-(3,4,5-trimethoxyphenoxy)phenoxy]pentyloxy)-(11aS)-1,2,3,11a-tetrahydro-5H-pyrrolo[2,1-c][1,4]benzodiazepin-5-one;

7-Methoxy-(8-(6-[3-amino-4-(3,4,5-trimethoxyphenoxy)phenoxy]hexyloxy)-(11aS)-1,2,3,11a-tetrahydro-5H-pyrrolo[2,1-c][1,4]benzodiazepin-5-one;

7-Methoxy-(8-3-[4-amino-3-(3,4,5-trimethoxyphenoxy)phenoxy]propoxy)-(11aS)-1,2,3,11a-tetrahydro-5H-pyrrolo[2,1-c][1,4]benzodiazepin-5-one;

7-Methoxy-(8-4-[4-amino-3-(3,4,5-trimethoxyphenoxy)phenoxy]butoxy)-(11aS)-1,2,3,11a-tetrahydro-5H-pyrrolo[2,1-c][1,4]benzodiazepin-5-one;

7-Methoxy-(8-5-[4-amino-3-(3,4,5-trimethoxyphenoxy)phenoxy]pentyloxy)-(11aS)-1,2,3,11a-tetrahydro-5H-pyrrolo[2,1-c][1,4]benzodiazepin-5-one;

7-Methoxy-(8-6-[4-amino-3-(3,4,5-trimethoxyphenoxy)phenoxy]hexyloxy)-(11aS)-1,2,3,11a-tetrahydro-5H-pyrrolo[2,1-c][1,4]benzodiazepin-5-one;

7-Methoxy-(8-3-[3-fluoro-4-(4-methoxyphenoxy)phenoxy]propoxy)-(11aS)-1,2,3,11a-tetrahydro-5H-pyrrolo[2,1-c][1,4]benzodiazepin-5-one;

7-Methoxy-(8-4-[3-fluoro-4-(4-methoxyphenoxy)phenoxy]butoxy)-(11aS)-1,2,3,11a-tetrahydro-5H-pyrrolo[2,1-c][1,4]benzodiazepin-5-one;

7-Methoxy-(8-(5-[3-fluoro-4-(4-methoxyphenoxy)phenoxy]pentyloxy)-(11aS)-1,2,3,11a-tetrahydro-5H-pyrrolo[2,1-c][1,4]benzodiazepin-5-one;

7-Methoxy-(8-(6-[3-fluoro-4-(4-methoxyphenoxy)phenoxy]hexyloxy)-(11aS)-1,2,3,11a-tetrahydro-5H-pyrrolo[2,1-c][1,4]benzodiazepin-5-one;

7-Methoxy-(8-3-[4-fluoro-3-(4-methoxyphenoxy)phenoxy]propoxy)-(11aS)-1,2,3,11a-tetrahydro-5H-pyrrolo[2,1-c][1,4]benzodiazepin-5-one;

7-Methoxy-(8-4-[4-fluoro-3-(4-methoxyphenoxy)phenoxy]butoxy)-(11aS)-1,2,3,11a-tetrahydro-5H-pyrrolo[2,1-c][1,4]benzodiazepin-5-one;

7-Methoxy-(8-5-[4-fluoro-3-(4-methoxyphenoxy)phenoxy]pentyloxy)-(11aS)-1,2,3,11a-tetrahydro-5H-pyrrolo[2,1-c][1,4]benzodiazepin-5-one;

7-Methoxy-(8-6-[4-fluoro-3-(4-methoxyphenoxy)phenoxy]hexyloxy)-(11aS)-1,2,3,11a-tetrahydro-5H-pyrrolo[2,1-c][1,4]benzodiazepin-5-one);

7-Methoxy-(8-3-[3-fluoro-4-(3,4-dimethoxyphenoxy)phenoxy]propoxy)-(11aS)-1,2,3,11a-tetrahydro-5H-pyrrolo[2,1-c][1,4]benzodiazepin-5-one;

7-Methoxy-(8-4-[3-fluoro-4-(3,4-dimethoxyphenoxy)phenoxy]butoxy)-(11aS)-1,2,3,11a-tetrahydro-5H-pyrrolo[2,1-c][1,4]benzodiazepin-5-one;

7-Methoxy-(8-(5-[3-fluoro-4-(3,4-dimethoxyphenoxy)phenoxy]pentyloxy)-(11aS)-1,2,3,11a-tetrahydro-5H-pyrrolo[2,1-c][1,4]benzodiazepin-5-one;

7-Methoxy-(8-(6-[3-fluoro-4-(3,4-dimethoxyphenoxy)phenoxy]hexyloxy)-(11aS)-1,2,3,11a-tetrahydro-5H-pyrrolo[2,1-c][1,4]benzodiazepin-5-one;

7-Methoxy-(8-3-[4-fluoro-3-(3,4-dimethoxyphenoxy)phenoxy]propoxy)-(11aS)-1,2,3,11a-tetrahydro-5H-pyrrolo[2,1-c][1,4]benzodiazepin-5-one;

7-Methoxy-(8-4-[4-fluoro-3-(3,4-dimethoxyphenoxy)phenoxy]butoxy)-(11aS)-1,2,3,11a-tetrahydro-5H-pyrrolo[2,1-c][1,4]benzodiazepin-5-one;

7-Methoxy-(8-5-[4-fluoro-3-(3,4-dimethoxyphenoxy)phenoxy]pentyloxy)-(11aS)-1,2,3,11a-tetrahydro-5H-pyrrolo[2,1-c][1,4]benzodiazepin-5-one;

7-Methoxy-(8-6-[4-fluoro-3-(3,4-dimethoxyphenoxy)phenoxy]hexyloxy)-(11aS)-1,2,3,11a-tetrahydro-5H-pyrrolo[2,1-c][1,4]benzodiazepin-5-one;

7-Methoxy-(8-3-[3-fluoro-4-(3,4,5-trimethoxyphenoxy)phenoxy]propoxy)-(11aS)-1,2,3,11a-tetrahydro-5H-pyrrolo[2,1-c][1,4]benzodiazepin-5-one;

7-Methoxy-(8-4-[3-fluoro-4-(3,4,5-trimethoxyphenoxy)phenoxy]butoxy)-(11aS)-1,2,3,11a-tetrahydro-5H-pyrrolo[2,1-c][1,4]benzodiazepin-5-one;

7-Methoxy-(8-(5-[3-fluoro-4-(3,4,5-trimethoxyphenoxy)phenoxy]pentyloxy)-(11aS)-1,2,3,11a-tetrahydro-5H-pyrrolo[2,1-c][1,4]benzodiazepin-5-one;

7-Methoxy-(8-(6-[3-fluoro-4-(3,4,5-trimethoxyphenoxy)phenoxy]hexyloxy)-(11aS)-1,2,3,11a-tetrahydro-5H-pyrrolo[2,1-c][1,4]benzodiazepin-5-one;

7-Methoxy-(8-3-[4-fluoro-3-(3,4,5-trimethoxyphenoxy)phenoxy]propoxy)-(11aS)-1,2,3,11a-tetrahydro-5H-pyrrolo[2,1-c][1,4]benzodiazepin-5-one;

7-Methoxy-(8-4-[4-fluoro-3-(3,4,5-trimethoxyphenoxy)phenoxy]butoxy)-(11aS)-1,2,3,11a-tetrahydro-5H-pyrrolo[2,1-c][1,4]benzodiazepin-5-one;

7-Methoxy-(8-5-[4-fluoro-3-(3,4,5-trimethoxyphenoxy)phenoxy]pentyloxy)-(11aS)-1,2,3,11a-tetrahydro-5H-pyrrolo[2,1-c][1,4]benzodiazepin-5-one;

7-Methoxy-(8-6-[4-fluoro-3-(3,4,5-trimethoxyphenoxy)phenoxy]hexyloxy)-(11aS)-1,2,3,11a-tetrahydro-5H-pyrrolo[2,1-c][1,4]benzodiazepin-5-one;

7-Methoxy-(8-3-[3-iodo-4-(4-methoxyphenoxy)phenoxy]propoxy)-(11aS)-1,2,3,11a-tetrahydro-5H-pyrrolo[2,1-c][1,4]benzodiazepin-5-one;

7-Methoxy-(8-4-[3-iodo-4-(4-methoxyphenoxy)phenoxy]butoxy)-(11aS)-1,2,3,11a-tetrahydro-5H-pyrrolo[2,1-c][1,4]benzodiazepin-5-one;

7-Methoxy-(8-(5-[3-iodo-4-(4-methoxyphenoxy)phenoxy]pentyloxy)-(11aS)-1,2,3,11a-tetrahydro-5H-pyrrolo[2,1-c][1,4]benzodiazepin-5-one;

7-Methoxy-(8-(6-[3-iodo-4-(4-methoxyphenoxy)phenoxy]hexyloxy)-(11aS)-1,2,3,11a-tetrahydro-5H-pyrrolo[2,1-c][1,4]benzodiazepin-5-one;

7-Methoxy-(8-3-[4-iodo-3-(4-methoxyphenoxy)phenoxy]propoxy)-(11aS)-1,2,3,11a-tetrahydro-5H-pyrrolo[2,1-c][1,4]benzodiazepin-5-one;

7-Methoxy-(8-4-[4-iodo-3-(4-methoxyphenoxy)phenoxy]butoxy)-(11aS)-1,2,3,11a-tetrahydro-5H-pyrrolo[2,1-c][1,4]benzodiazepin-5-one;

7-Methoxy-(8-5-[4-iodo-3-(4-methoxyphenoxy)phenoxy]pentyloxy)-(11aS)-1,2,3,11a-tetrahydro-5H-pyrrolo[2,1-c][1,4]benzodiazepin-5-one;

7-Methoxy-(8-6-[4-iodo-3-(4-methoxyphenoxy)phenoxy]hexyloxy)-(11aS)-1,2,3,11a-tetrahydro-5H-pyrrolo[2,1-c][1,4]benzodiazepin-5-one;

7-Methoxy-(8-3-[3-iodo-4-(3,4-dimethoxyphenoxy)phenoxy]propoxy)-(11aS)-1,2,3,11a-tetrahydro-5H-pyrrolo[2,1-c][1,4]benzodiazepin-5-one;

7-Methoxy-(8-4-[3-iodo-4-(3,4-dimethoxyphenoxy)phenoxy]butoxy)-(11aS)-1,2,3,11a-tetrahydro-5H-pyrrolo[2,1-c][1,4]benzodiazepin-5-one;

7-Methoxy-(8-(5-[3-iodo-4-(3,4-dimethoxyphenoxy)phenoxy]pentyloxy)-(11aS)-1,2,3,11a-tetrahydro-5H-pyrrolo[2,1-c][1,4]benzodiazepin-5-one;

7-Methoxy-(8-(6-[3-iodo-4-(3,4-dimethoxyphenoxy)phenoxy]hexyloxy)-(11aS)-1,2,3,11a-tetrahydro-5H-pyrrolo[2,1-c][1,4]benzodiazepin-5-one;

7-Methoxy-(8-3-[4-iodo-3-(3,4-dimethoxyphenoxy)phenoxy]propoxy)-(11aS)-1,2,3,11a-tetrahydro-5H-pyrrolo[2,1-c][1,4]benzodiazepin-5-one;

7-Methoxy-(8-4-[4-iodo-3-(3,4-dimethoxyphenoxy)phenoxy]butoxy)-(11aS)-1,2,3,11a-tetrahydro-5H-pyrrolo[2,1-c][1,4]benzodiazepin-5-one;

7-Methoxy-(8-5-[4-iodo-3-(3,4-dimethoxyphenoxy)phenoxy]pentyloxy)-(11aS)-1,2,3,11a-tetrahydro-5H-pyrrolo[2,1-c][1,4]benzodiazepin-5-one;

7-Methoxy-(8-6-[4-iodo-3-(3,4-dimethoxyphenoxy)phenoxy]hexyloxy)-(11aS)-1,2,3,11a-tetrahydro-5H-pyrrolo[2,1-c][1,4]benzodiazepin-5-one;

7-Methoxy-(8-3-[3-iodo-4-(3,4,5-trimethoxyphenoxy)phenoxy]propoxy)-(11aS)-1,2,3,11a-tetrahydro-5H-pyrrolo[2,1-c][1,4]benzodiazepin-5-one;

7-Methoxy-(8-4-[3-iodo-4-(3,4,5-trimethoxyphenoxy)phenoxy]butoxy)-(11aS)-1,2,3,11a-tetrahydro-5H-pyrrolo[2,1-c][1,4]benzodiazepin-5-one;

7-Methoxy-(8-(5-[3-iodo-4-(3,4,5-trimethoxyphenoxy)phenoxy]pentyloxy)-(11aS)-1,2,3,11a-tetrahydro-5H-pyrrolo[2,1-c][1,4]benzodiazepin-5-one;

7-Methoxy-(8-(6-[3-iodo-4-(3,4,5-trimethoxyphenoxy)phenoxy]hexyloxy)-(11aS)-1,2,3,11a-tetrahydro-5H-pyrrolo[2,1-c][1,4]benzodiazepin-5-one;

7-Methoxy-(8-3-[4-iodo-3-(3,4,5-trimethoxyphenoxy)phenoxy]propoxy)-(11aS)-1,2,3,11a-tetrahydro-5H-pyrrolo[2,1-c][1,4]benzodiazepin-5-one;

7-Methoxy-(8-4-[4-iodo-3-(3,4,5-trimethoxyphenoxy)phenoxy]butoxy)-(11aS)-1,2,3,11a-tetrahydro-5H-pyrrolo[2,1-c][1,4]benzodiazepin-5-one;

7-Methoxy-(8-5-[4-iodo-3-(3,4,5-trimethoxyphenoxy)phenoxy]pentyloxy)-(11aS)-1,2,3,11a-tetrahydro-5H-pyrrolo[2,1-c][1,4]benzodiazepin-5-one;

7-Methoxy-(8-6-[4-iodo-3-(3,4,5-trimethoxyphenoxy)phenoxy]hexyloxy)-(11aS)-1,2,3,11a-tetrahydro-5H-pyrrolo[2,1-c][1,4]benzodiazepin-5-one;

7-Methoxy-(8-3-[4-(4-methoxyphenoxy)-3-nitrophenoxy]propoxy)-(11aS)-1,2,3,11a-tetrahydro-5H-pyrrolo[2,1-c][1,4]benzodiazepin-5-one;

7-Methoxy-(8-3-[4-(4-methoxyphenoxy)-3-nitrophenoxy]butoxy)-(11aS)-1,2,3,11a-tetrahydro-5H-pyrrolo[2,1-c][1,4]benzodiazepin-5-one;

7-Methoxy-(8-3-[4-(4-methoxyphenoxy)-3-nitrophenoxy]pentyloxy)-(11aS)-1,2,3,11a-tetrahydro-5H-pyrrolo[2,1-c][1,4]benzodiazepin-5-one;

7-Methoxy-(8-3-[4-(4-methoxyphenoxy)-3-nitrophenoxy]hexyloxy)-(11aS)-1,2,3,11a-tetrahydro-5H-pyrrolo[2,1-c][1,4]benzodiazepin-5-one;

7-Methoxy-(8-3-[3-(4-methoxyphenoxy)-2-nitrophenoxy]propoxy)-(11aS)-1,2,3,11a-tetrahydro-5H-pyrrolo[2,1-c][1,4]benzodiazepin-5-one;

7-Methoxy-(8-3-[3-(4-methoxyphenoxy)-2-nitrophenoxy]butoxy)-(11aS)-1,2,3,11a-tetrahydro-5H-pyrrolo[2,1-c][1,4]benzodiazepin-5-one;

7-Methoxy-(8-3-[3-(4-methoxyphenoxy)-2-nitrophenoxy]pentyloxy)-(11aS)-1,2,3,11a-tetrahydro-5H-pyrrolo[2,1-c][1,4]benzodiazepin-5-one;

7-Methoxy-(8-3-[3-(4-methoxyphenoxy)-2-nitrophenoxy]hexyloxy)-(11aS)-1,2,3,11a-tetrahydro-5H-pyrrolo[2,1-c][1,4]benzodiazepin-5-one;

7-Methoxy-(8-3-[4-(3,4-dimethoxyphenoxy)-3-nitrophenoxy]propoxy)-(11aS)-1,2,3,11a-tetrahydro-5H-pyrrolo[2,1-c][1,4]benzodiazepin-5-one;

7-Methoxy-(8-3-[4-(3,4-dimethoxyphenoxy)-3-nitrophenoxy]butoxy)-(11aS)-1,2,3,11a-tetrahydro-5H-pyrrolo[2,1-c][1,4]benzodiazepin-5-one;

7-Methoxy-(8-3-[4-(3,4-dimethoxyphenoxy)-3-nitrophenoxy]pentyloxy)-(11aS)-1,2,3,11a-tetrahydro-5H-pyrrolo[2,1-c][1,4]benzodiazepin-5-one;

7-Methoxy-(8-3-[4-(3,4-dimethoxyphenoxy)-3-nitrophenoxy]hexyloxy)-(11aS)-1,2,3,11a-tetrahydro-5H-pyrrolo[2,1-c][1,4]benzodiazepin-5-one;

7-Methoxy-(8-3-[3-(3,4-dimethoxyphenoxy)-2-nitrophenoxy]propoxy)-(11aS)-1,2,3,11a-tetrahydro-5H-pyrrolo[2,1-c][1,4]benzodiazepin-5-one;

7-Methoxy-(8-3-[3-(3,4-dimethoxyphenoxy)-2-nitrophenoxy]butoxy)-(11aS)-1,2,3,11a-tetrahydro-5H-pyrrolo[2,1-c][1,4]benzodiazepin-5-one;

7-Methoxy-(8-3-[3-(3,4-dimethoxyphenoxy)-2-nitrophenoxy]pentyloxy)-(11aS)-1,2,3,11a-tetrahydro-5H-pyrrolo[2,1-c][1,4]benzodiazepin-5-one;

7-Methoxy-(8-3-[3-(3,4-dimethoxyphenoxy)-2-nitrophenoxy]hexyloxy)-(11aS)-1,2,3,11a-tetrahydro-5H-pyrrolo[2,1-c][1,4]benzodiazepin-5-one;

7-Methoxy-(8-3-[4-(3,4,5-trimethoxyphenoxy)-3-nitrophenoxy)-(11aS)-1,2,3,11a-tetrahydro-5H-pyrrolo[2,1-c][1,4]benzodiazepin-5-one;

7-Methoxy-(8-3-[4-(3,4,5-trimethoxyphenoxy)-3-nitrophenoxy]butoxy)-(11aS)-1,2,3,11a-tetrahydro-5H-pyrrolo[2,1-c][1,4]benzodiazepin-5-one;

7-Methoxy-(8-3-[4-(3,4,5-timethoxyphenoxy)-3-nitrophenoxy]pentyloxy)-(11aS)-1,2,3,11a-tetrahydro-5H-pyrrolo[2,1-c][1,4]benzodiazepin-5-one;

7-Methoxy-(8-3-[4-(3,4,5-trimethoxyphenoxy)-3-nitrophenoxy]hexyloxy)-(11aS)-1,2,3,11a-tetrahydro-5H-pyrrolo[2,1-c][1,4]benzodiazepin-5-one;

7-Methoxy-(8-3-[3-(3,4,5-trimethoxyphenoxy)-2-nitrophenoxy)-(11aS)-1,2,3,11a-tetrahydro-5H-pyrrolo[2,1-c][1,4]benzodiazepin-5-one;

7-Methoxy-(8-3-[3-(3,4,5-trimethoxyphenoxy)-2-nitrophenoxy]butoxy)-(11aS)-1,2,3,11a-tetrahydro-5H-pyrrolo[2,1-c][1,4]benzodiazepin-5-one;

7-Methoxy-(8-3-[3-(3,4,5-trimethoxyphenoxy)-2-nitrophenoxy]pentyloxy)-(11aS)-1,2,3,11a-tetrahydro-5H-pyrrolo[2,1-c][1,4]benzodiazepin-5-one;

7-Methoxy-(8-3-[3-(3,4,5-trimethoxyphenoxy)-2-nitrophenoxy]hexyloxy)-(11aS)-1,2,3,11a-tetrahydro-5H-pyrrolo[2,1-c][1,4]benzodiazepin-5-one;

7-Methoxy-(8-(3-4-[3-amino-4-(4-methoxyphenoxy)benzoyl]piperazinopropoxy)-(11aS)-1,2,3,11a-tetrahydro-5H-pyrrolo[2,1-c][1,4]benzodiazepin-5-one;

7-Methoxy-(8-(3-4-[3-amino-4-(4-methoxyphenoxy)benzoyl]piperazinobutoxy)-(11aS)-1,2,3,11a-tetrahydro-5H-pyrrolo[2,1-c][1,4]benzodiazepin-5-one;

7-Methoxy-(8-(3-4-[3-amino-4-(4-methoxyphenoxy)benzoyl]piperazinopentyloxy)-(11aS)-1,2,3,11a-tetrahydro-5H-pyrrolo[2,1-c][1,4]benzodiazepin-5-one;

7-Methoxy-(8-(3-4-[3-amino-4-(4-methoxyphenoxy)benzoyl]piperazinohexyloxy)-(11aS)-1,2,3,11a-tetrahydro-5H-pyrrolo[2,1-c][1,4]benzodiazepin-5-one;

7-Methoxy-(8-(3-4-[3-amino-4-(3,4-dimethoxyphenoxy)benzoyl]piperazinopropoxy)-(11aS)-1,2,3,11a-tetrahydro-5H-pyrrolo[2,1-c][1,4]benzodiazepin-5-one;

7-Methoxy-(8-(3-4-[3-amino-4-(3,4-dimethoxyphenoxy)benzoyl]piperazinobutoxy)-(11aS)-1,2,3,11a-tetrahydro-5H-pyrrolo[2,1-c][1,4]benzodiazepin-5-one;

7-Methoxy-(8-(3-4-[3-amino-4-(3,4-dimethoxyphenoxy)benzoyl]piperazinopentyloxy)-(11aS)-1,2,3,11a-tetrahydro-5H-pyrrolo[2,1-c][1,4]benzodiazepin-5-one;

7-Methoxy-(8-(3-4-[3-amino-4-(3,4-dimethoxyphenoxy)benzoyl]piperazinohexyloxy)-(11aS)-1,2,3,11a-tetrahydro-5H-pyrrolo[2,1-c][1,4]benzodiazepin-5-one;

7-Methoxy-(8-(3-4-[3-amino-4-(3,4,5-trimethoxyphenoxy)benzoyl]piperazinopropoxy)-(11aS)-1,2,3,11a-tetrahydro-5H-pyrrolo[2,1-c][1,4]benzodiazepin-5-one;

7-Methoxy-(8-(3-4-[3-amino-4-(3,4,5-trimethoxyphenoxy)benzoyl]piperazinobutoxy)-(11aS)-1,2,3,11a-tetrahydro-5H-pyrrolo[2,1-c][1,4]benzodiazepin-5-one;

7-Methoxy-(8-(3-4-[3-amino-4-(3,4,5-trimethoxyphenoxy)benzoyl]piperazinopentyloxy)-(11aS)-1,2,3,11a-tetrahydro-5H-pyrrolo[2,1-c][1,4]benzodiazepin-5-one;

7-Methoxy-(8-(3-4-[3-amino-4-(3,4,5-trimethoxyphenoxy)benzoyl]piperazinohexyloxy)-(11aS)-1,2,3,11a-tetrahydro-5H-pyrrolo[2,1-c][1,4]benzodiazepin-5-one;

7-Methoxy-(8-(3-4-[3-fluoro-4-(4-methoxyphenoxy)benzoyl]piperazinopropoxy)-(11aS)-1,2,3,11a-tetrahydro-5H-pyrrolo[2,1-c][1,4]benzodiazepin-5-one;

7-Methoxy-(8-(3-4-[3-fluoro-4-(4-methoxyphenoxy)benzoyl]piperazinobutoxy)-(11aS)-1,2,3,11a-tetrahydro-5H-pyrrolo[2,1-c][1,4]benzodiazepin-5-one;

7-Methoxy-(8-(3-4-[3-fluoro-4-(4-methoxyphenoxy)benzoyl]piperazinopentyloxy)-(11aS)-1,2,3,11a-tetrahydro-5H-pyrrolo[2,1-c][1,4]benzodiazepin-5-one;

7-Methoxy-(8-(3-4-[3-fluoro-4-(4-methoxyphenoxy)benzoyl]piperazinohexyloxy)-(11aS)-1,2,3,11a-tetrahydro-5H-pyrrolo[2,1-c][1,4]benzodiazepin-5-one;

7-Methoxy-(8-(3-4-[3-fluoro-4-(3,4-dimethoxyphenoxy)benzoyl]piperazinopropoxy)-(11aS)-1,2,3,11a-tetrahydro-5H-pyrrolo[2,1-c][1,4]benzodiazepin-5-one;

7-Methoxy-(8-(3-4-[3-fluoro-4-(3,4-dimethoxyphenoxy)benzoyl]piperazinobutoxy)-(11aS)-1,2,3,11a-tetrahydro-5H-pyrrolo[2,1-c][1,4]benzodiazepin-5-one;

7-Methoxy-(8-(3-4-[3-fluoro-4-(3,4-dimethoxyphenoxy)benzoyl]piperazinopentyloxy)-(11aS)-1,2,3,11a-tetrahydro-5H-pyrrolo[2,1-c][1,4]benzodiazepin-5-one;

7-Methoxy-(8-(3-4-[3-fluoro-4-(3,4-dimethoxyphenoxy)benzoyl]piperazinohexyloxy)-(11aS)-1,2,3,11a-tetrahydro-5H-pyrrolo[2,1-c][1,4]benzodiazepin-5-one;

7-Methoxy-(8-(3-4-[3-fluoro-4-(3,4,5-trimethoxyphenoxy)benzoyl]piperazinopropoxy)-(11aS)-1,2,3,11a-tetrahydro-5H-pyrrolo[2,1-c][1,4]benzodiazepin-5-one;

7-Methoxy-(8-(3-4-[3-fluoro-4-(3,4,5-trimethoxyphenoxy)benzoyl]piperazinobutoxy)-(11aS)-1,2,3,11a-tetrahydro-5H-pyrrolo[2,1-c][1,4]benzodiazepin-5-one;

7-Methoxy-(8-(3-4-[3-fluoro-4-(3,4,5-trimethoxyphenoxy)benzoyl]piperazinopentyloxy)-(11aS)-1,2,3,11a-tetrahydro-5H-pyrrolo[2,1-c][1,4]benzodiazepin-5-one;

7-Methoxy-(8-(3-4-[3-fluoro-4-(3,4,5-trimethoxyphenoxy)benzoyl]piperazinohexyloxy)-(11aS)-1,2,3,11a-tetrahydro-5H-pyrrolo[2,1-c][1,4]benzodiazepin-5-one;

7-Methoxy-(8-(3-4-[3-iodo-4-(4-methoxyphenoxy)benzoyl]piperazinopropoxy)-(11aS)-1,2,3,11a-tetrahydro-5H-pyrrolo[2,1-c][1,4]benzodiazepin-5-one;

7-Methoxy-(8-(3-4-[3-iodo-4-(4-methoxyphenoxy)benzoyl]piperazinobutoxy)-(11aS)-1,2,3,11a-tetrahydro-5H-pyrrolo[2,1-c][1,4]benzodiazepin-5-one;

7-Methoxy-(8-(3-4-[3-iodo-4-(4-methoxyphenoxy)benzoyl]piperazinopentyloxy)-(11aS)-1,2,3,11a-tetrahydro-5H-pyrrolo[2,1-c][1,4]benzodiazepin-5-one;

7-Methoxy-(8-(3-4-[3-iodo-4-(4-methoxyphenoxy)benzoyl]piperazinohexyloxy)-(11aS)-1,2,3,11a-tetrahydro-5H-pyrrolo[2,1-c][1,4]benzodiazepin-5-one;

7-Methoxy-(8-(3-4-[3-iodo-4-(3,4-dimethoxyphenoxy)benzoyl]piperazinopropoxy)-(11aS)-1,2,3,11a-tetrahydro-5H-pyrrolo[2,1-c][1,4]benzodiazepin-5-one;

7-Methoxy-(8-(3-4-[3-iodo-4-(3,4-dimethoxyphenoxy)benzoyl]piperazinobutoxy)-(11aS)-1,2,3,11a-tetrahydro-5H-pyrrolo[2,1-c][1,4]benzodiazepin-5-one;

7-Methoxy-(8-(3-4-[3-iodo-4-(3,4-dimethoxyphenoxy)benzoyl]piperazinopentyloxy)-(11aS)-1,2,3,11a-tetrahydro-5H-pyrrolo[2,1-c][1,4]benzodiazepin-5-one;

7-Methoxy-(8-(3-4-[3-iodo-4-(3,4-dimethoxyphenoxy)benzoyl]piperazinohexyloxy)-(11aS)-1,2,3,11a-tetrahydro-5H-pyrrolo[2,1-c][1,4]benzodiazepin-5-one;

7-Methoxy-(8-(3-4-[3-iodo-4-(3,4,5-trimethoxyphenoxy)benzoyl]piperazinopropoxy)-(11aS)-1,2,3,11a-tetrahydro-5H-pyrrolo[2,1-c][1,4]benzodiazepin-5-one;

7-Methoxy-(8-(3-4-[3-iodo-4-(3,4,5-trimethoxyphenoxy)benzoyl]piperazinobutoxy)-(11aS)-1,2,3,11a-tetrahydro-5H-pyrrolo[2,1-c][1,4]benzodiazepin-5-one;

7-Methoxy-(8-(3-4-[3-iodo-4-(3,4,5-trimethoxyphenoxy)benzoyl]piperazino pentyloxy)-(11aS)-1,2,3,11a-tetrahydro-5H-pyrrolo[2,1-c][1,4]benzodiazepin-5-one;

7-Methoxy-(8-(3-4-[3-iodo-4-(3,4,5-trimethoxyphenoxy)benzoyl]piperazinohexyloxy)-(11aS)-1,2,3,11a-tetrahydro-5H-pyrrolo[2,1-c][1,4]benzodiazepin-5-one;

7-Methoxy-(8-(3-4-[4-(4-methoxyphenoxy)-3-nitrobenzoyl]piperazinopropoxy)-(11aS)-1,2,3,11a-tetrahydro-5H-pyrrolo[2,1-c][1,4]benzodiazepin-5-one;

7-Methoxy-(8-(3-4-[4-(4-methoxyphenoxy)-3-nitrobenzoyl]piperazinobutoxy)-(11aS)-1,2,3,11a-tetrahydro-5H-pyrrolo[2,1-c][1,4]benzodiazepin-5-one;

7-Methoxy-(8-(3-4-[4-(4-methoxyphenoxy)-3-nitrobenzoyl]piperazinopentyloxy)-(11aS)-1,2,3,11a-tetrahydro-5H-pyrrolo[2,1-c][1,4]benzodiazepin-5-one;

7-Methoxy-(8-(3-4-[4-(4-methoxyphenoxy)-3-nitrobenzoyl]piperazinohexyloxy)-(11aS)-1,2,3,11a-tetrahydro-5H-pyrrolo[2,1-c][1,4]benzodiazepin-5-one;

7-Methoxy-(8-(3-4-[4-(3,4-dimethoxyphenoxy)-3-nitrobenzoyl]piperazinopropoxy)-(11aS)-1,2,3,11a-tetrahydro-5H-pyrrolo[2,1-c][1,4]benzodiazepin-5-one;

7-Methoxy-(8-(3-4-[4-(3,4-dimethoxyphenoxy)-3-nitrobenzoyl]piperazinobutoxy)-(11aS)-1,2,3,11a-tetrahydro-5H-pyrrolo[2,1-c][1,4]benzodiazepin-5-one;

7-Methoxy-(8-(3-4-[4-(3,4-dimethoxyphenoxy)-3-nitrobenzoyl]piperazinopentyloxy)-(11aS)-1,2,3,11a-tetrahydro-5H-pyrrolo[2,1-c][1,4]benzodiazepin-5-one;

7-Methoxy-(8-(3-4-[4-(3,4-dimethoxyphenoxy)-3-nitrobenzoyl]piperazinohexyloxy)-(11aS)-1,2,3,11a-tetrahydro-5H-pyrrolo[2,1-c][1,4]benzodiazepin-5-one;

7-Methoxy-(8-(3-4-[4-(3,4,5-trimethoxyphenoxy)-3-nitrobenzoyl]piperazinopropoxy)-(11aS)-1,2,3,11a-tetrahydro-5H-pyrrolo[2,1-c][1,4]benzodiazepin-5-one;

7-Methoxy-(8-(3-4-[4-(3,4,5-trimethoxyphenoxy)-3-nitrobenzoyl]piperazinbutoxy)-(11aS)-1,2,3,11a-tetrahydro-5H-pyrrolo[2,1-c][1,4]benzodiazepin-5-one;

7-Methoxy-(8-(3-4-[4-(3,4,5-trimethoxyphenoxy)-3-nitrobenzoyl]piperazinopentyloxy)-(11aS)-1,2,3,11a-tetrahydro-5H-pyrrolo[2,1-c][1,4]benzodiazepin-5-one; and 7-Methoxy-(8-(3-4-[4-(3,4,5-trimethoxyphenoxy)-3-nitrobenzoyl]piperazinohexyloxy)-(11aS)-1,2,3,11a-tetrahydro-5H-pyrrolo[2,1-c][1,4]benzodiazepin-5-one.

3. The compound of claim 1, having formula (10g):

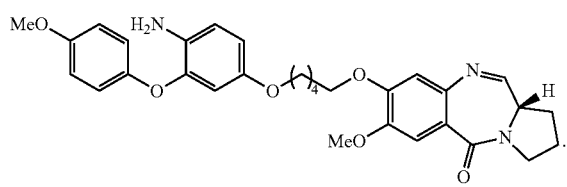

(10g)

4. The compound of claim 1, having formula (11g):

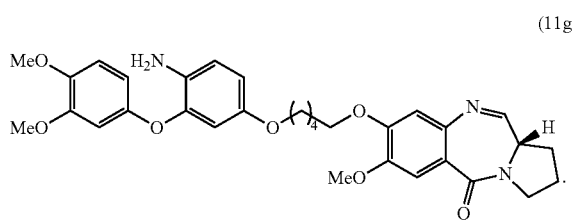

(11g)

5. The compound of claim 1, having formula (12g):

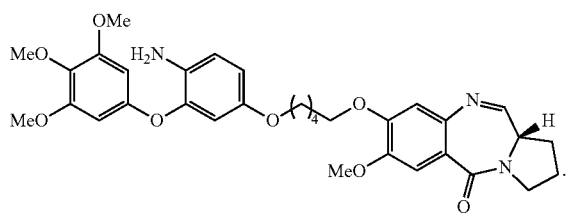

(12g)

6. The compound of claim 1, having formula (16c):

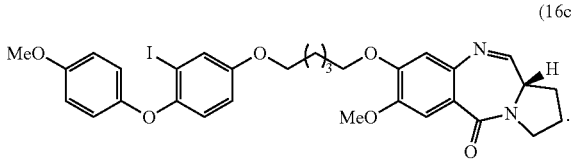

(16c)

7. The compound of claim 1, having a formula (17c):

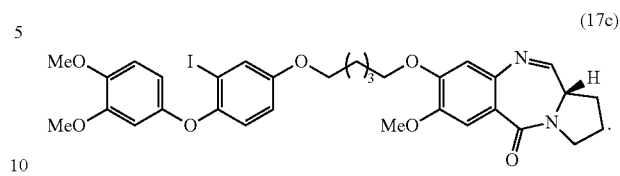

(17c)

8. The compound of claim 1, having formula (17g):

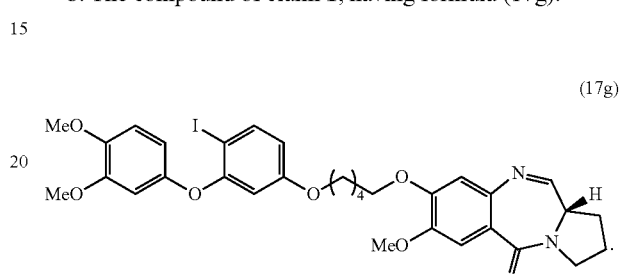

(17g)

9. The compound of claim 1, having formula (18c):

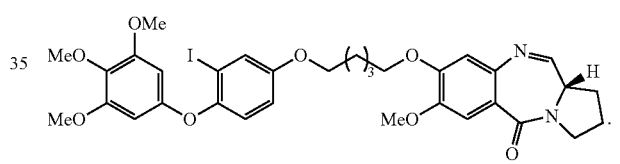

(18c)

10. The compound of claim 1, having formula (19g):

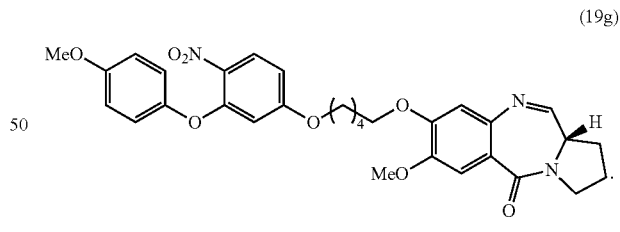

(19g)

11. The compound of claim 1, having formula (20c):

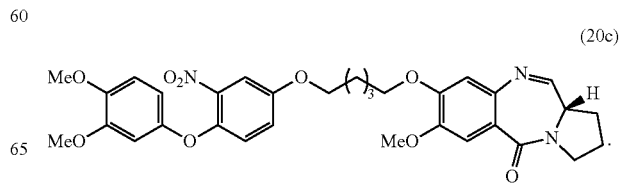

(20c)

12. The compound of claim 1, having formula (23c):

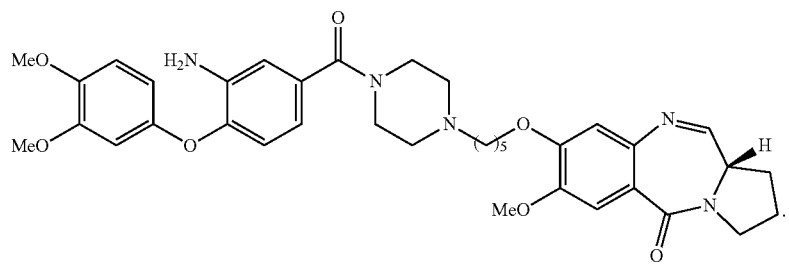
(23c)

13. The compound of claim 1, having formula (24c):

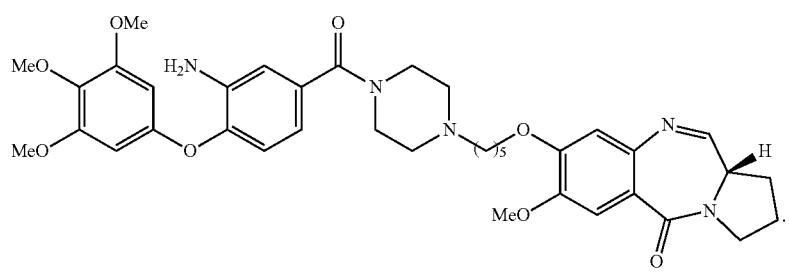
(24c)

14. A method of inhibiting growth of cancer cells in a patient in need thereof, comprising:

administering to a patient in need thereof a therapeutically effective amount of a compound of claim 1, whereby growth of cancer cells is inhibited, wherein the cancer cells are selected from the group consisting of breast cancer cells, lung cancer cells, ovarian cancer cells, oral cancer cells, cervix cancer cells, colon cancer cells, and prostate cancer cells.

15. A process for the preparation of a compound of claim 1, comprising:

i. reacting a compound of formula 3a-d with a compound selected from the group consisting of compounds of formula 5a-x and compounds of formula 7a-l in a 1:1 ratio in a presence of $K_2CO_3$ in acetone solvent at a refluxing temperature in a range of from 56° C. to 60° C. for a period of from 24 to 48 hours, whereby an amino compound of general formula 8 is obtained if the compound of formula 5a-x is a reactant and whereby a compound of general formula 9 is obtained if the compound of formula 7a-l is a reactant, wherein the compounds of formula 3a-d, formula 5a-x, formula 7a-l, general formula 8, and general formula 9 have the following structures:

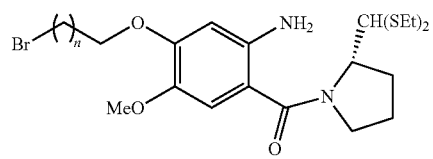
3a-d n = 2, 3, 4, or 5;

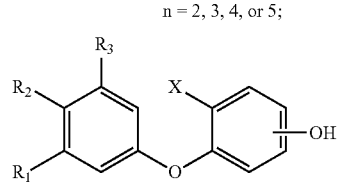
5a-x $R_1, R_2, R_3$ = H or OMe;
X = $NO_2$, $NH_2$, F, or I;

-continued

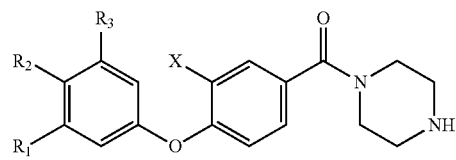
7a-l $R_1, R_2, R_3$ = H or OMe;
X = $NO_2$, $NH_2$, F, or I;

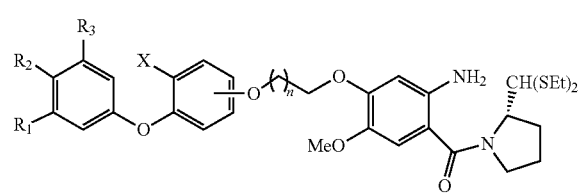
8

$R_1, R_2, R_3$ = H or OMe;
X = $NO_2$, $NH_2$, F, or I;
n = 2, 3, 4 or 5;

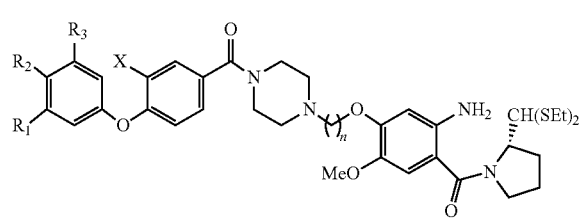
9

$R_1, R_2, R_3$ = H or OMe;
X = $NO_2$, $NH_2$, F, or I;
n = 3, 4, 5 or 6; and ii. reacting the amino compound of general formula 8 or general formula 9 with a deprotecting agent HgCl₂ and CaCO₃ in MeCN:H₂O at a temperature in a range of from 27° C. to 30° C. for period of from 12 to 24 hours, whereby a compound is obtained having a formula selected from the group consisting of:
(10a)
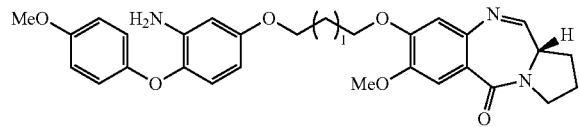
(10b)
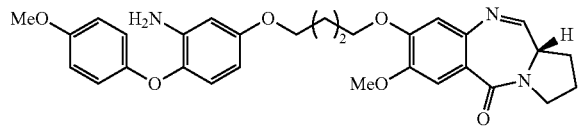
(10c)
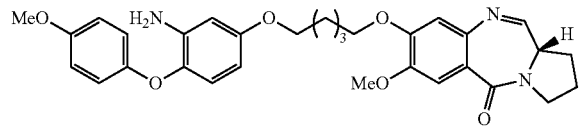
(10d)
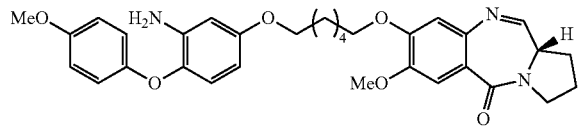
(10e)
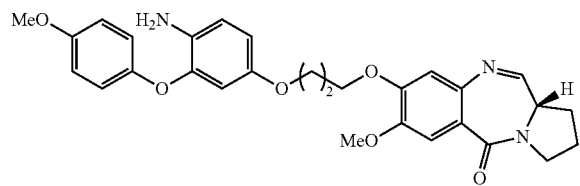
(10f)
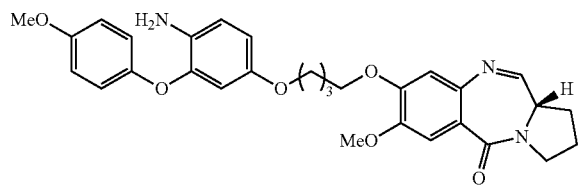
(10g)
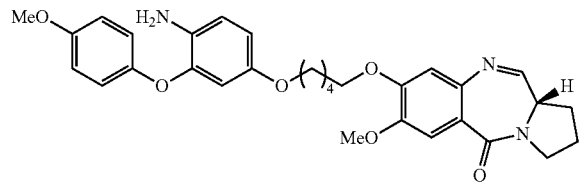
(10h)
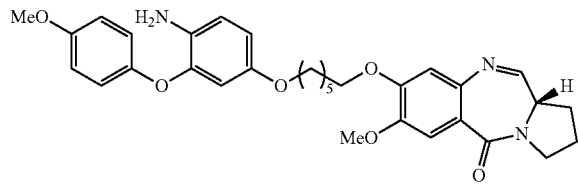
(11a)
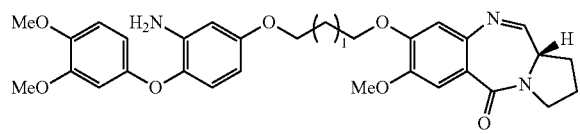
(11b)
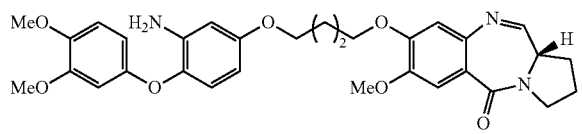
(11c)
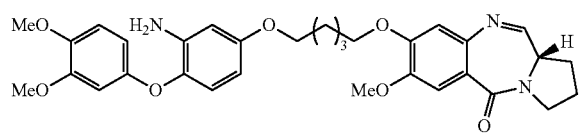
(11d)
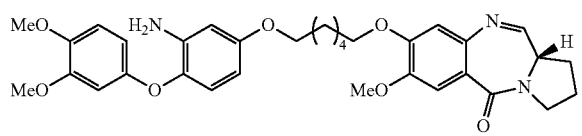
(11e)
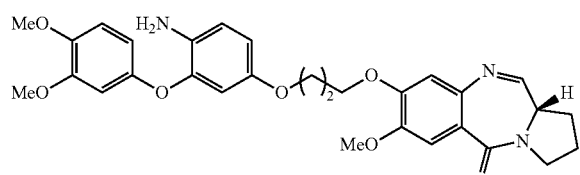
(11f)
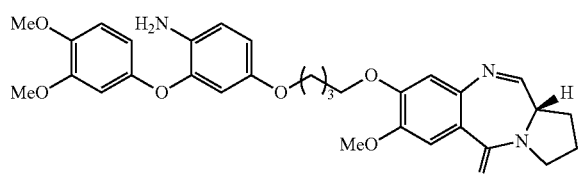
(11g)
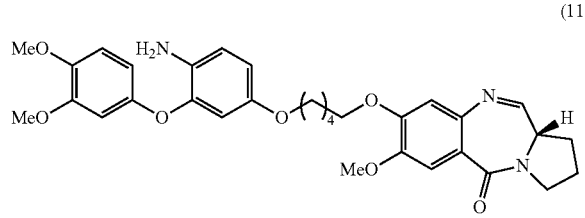
(11h)
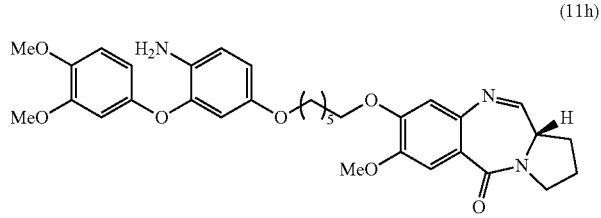

-continued
(12a)
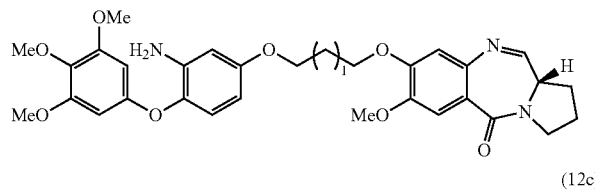
(12b)
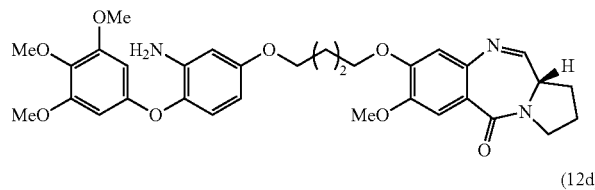
(12c)
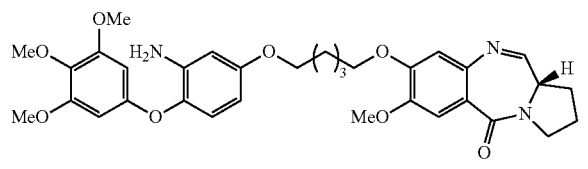
(12d)
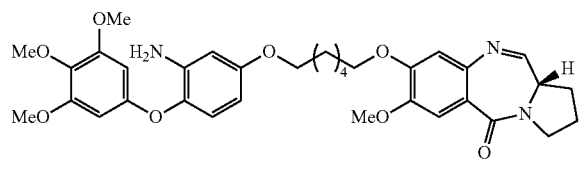
(12e)
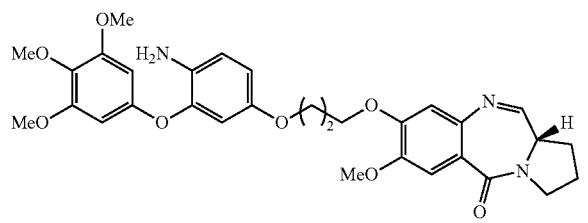
(12f)
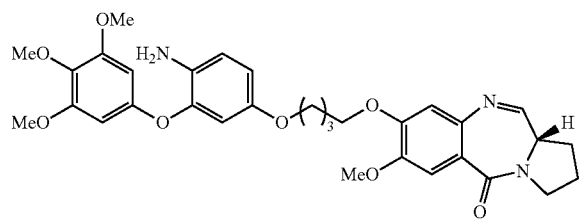
(12g)
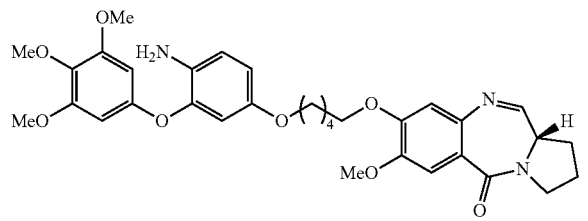
(12h)
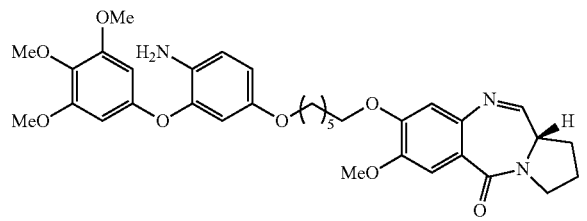
(13a)
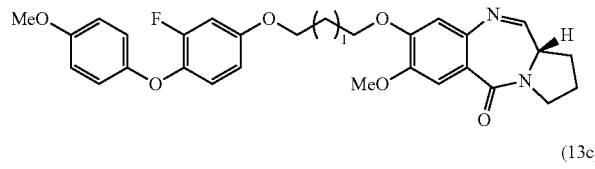
(13b)
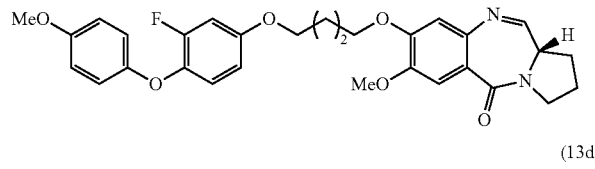
(13c)
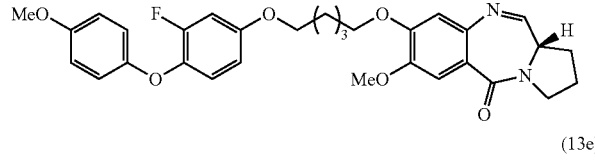
(13d)
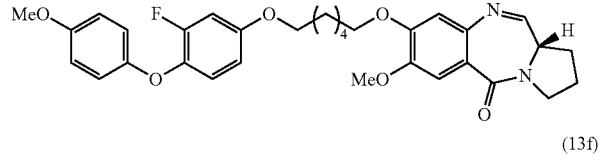
(13e)
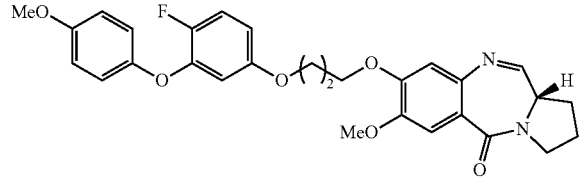
(13f)
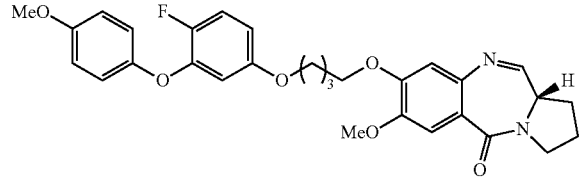
(13g)
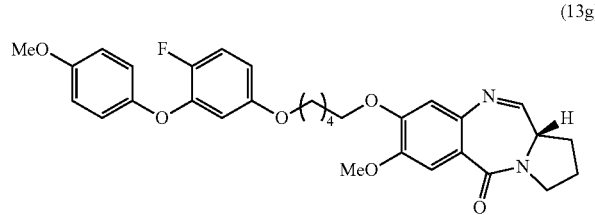
(13h)
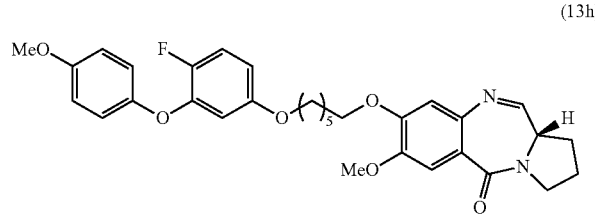

-continued

-continued (18a)
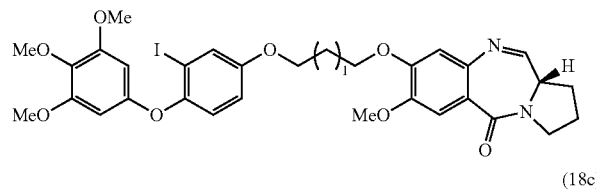
(18b)
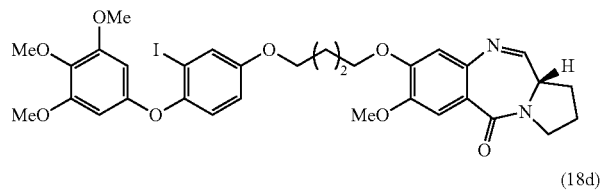
(18c)
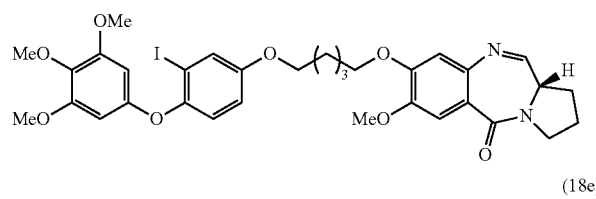
(18d)
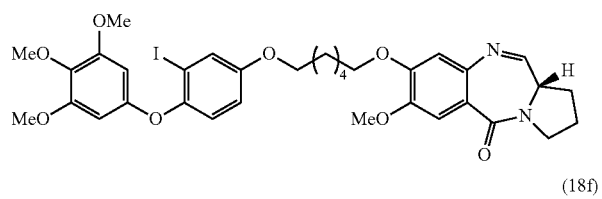
(18e)
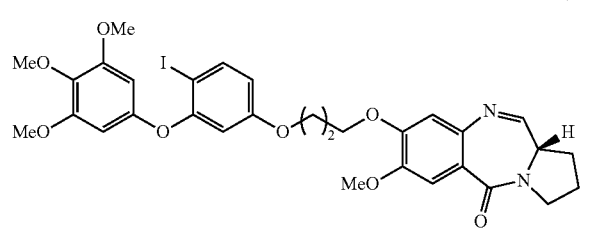
(18f)
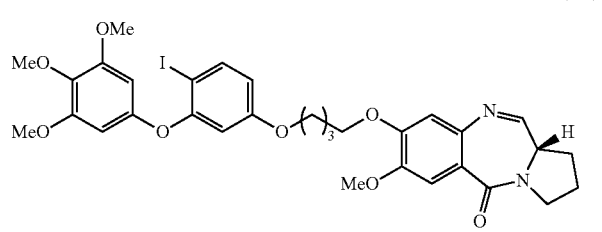
(18g)
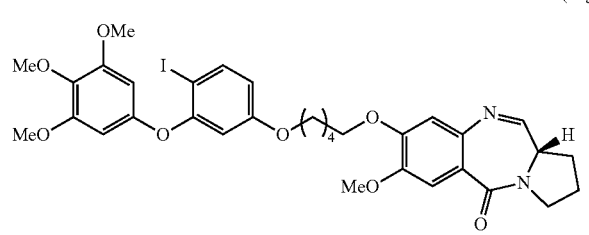
(18h)
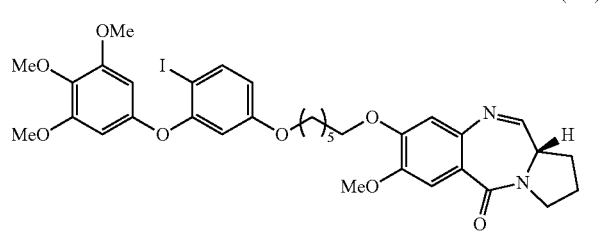
(19a)
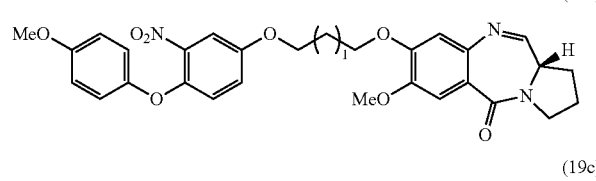
(19b)
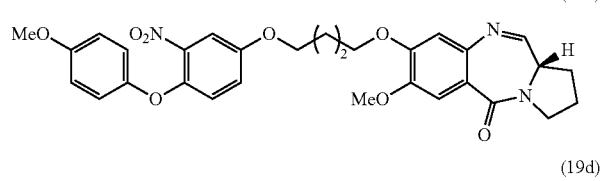
(19c)
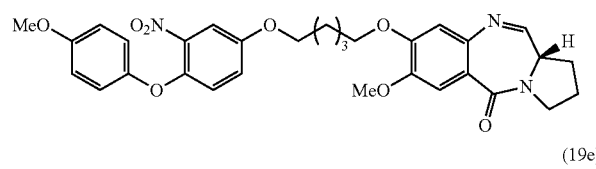
(19d)
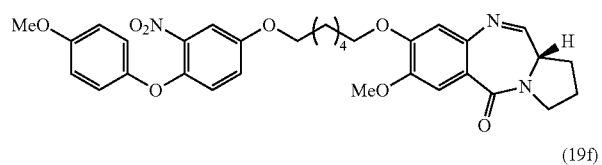
(19e)
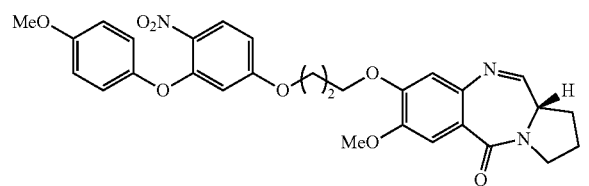
(19f)
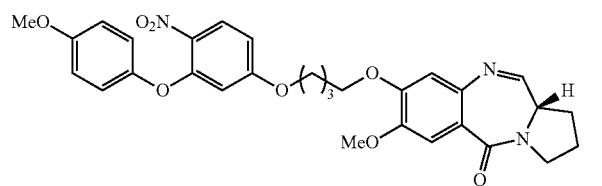
(19g)
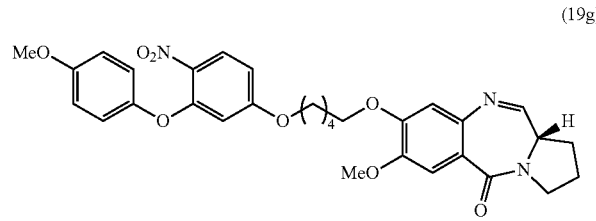
(19h)
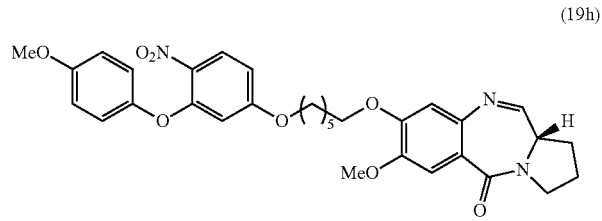

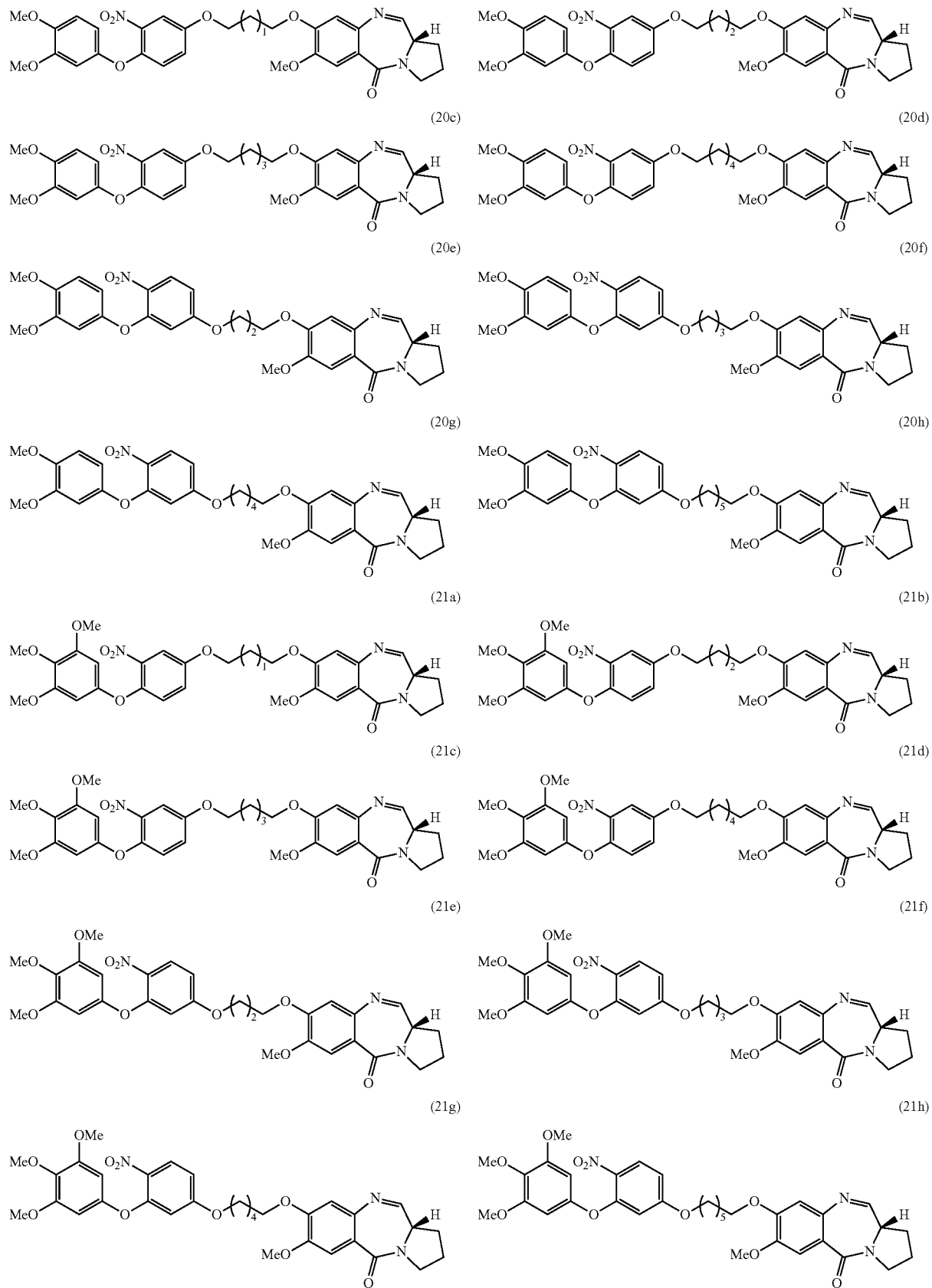

-continued
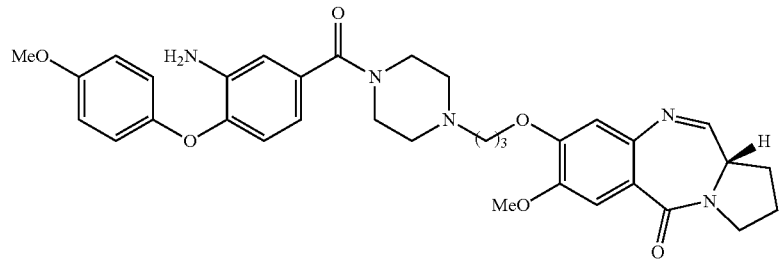
(22a)
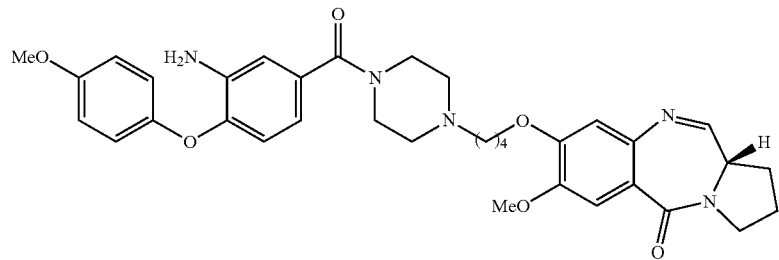
(22b)
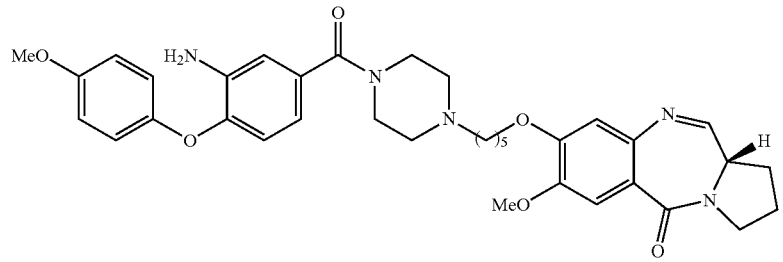
(22c)
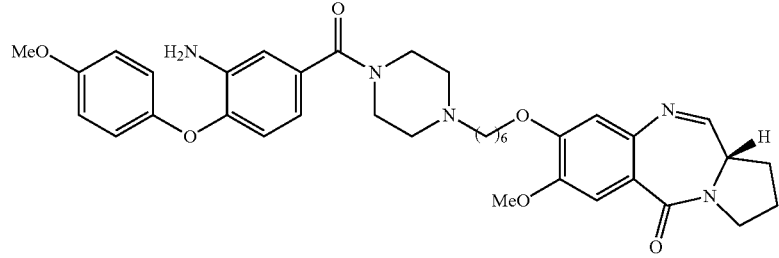
(22d)
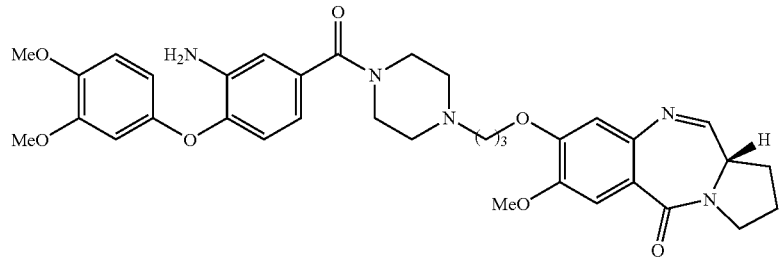
(23a)
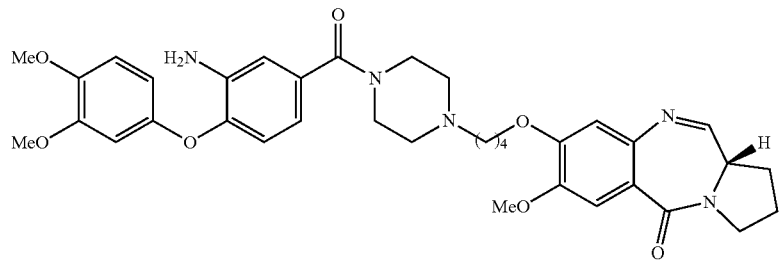
(23b)

(23c)
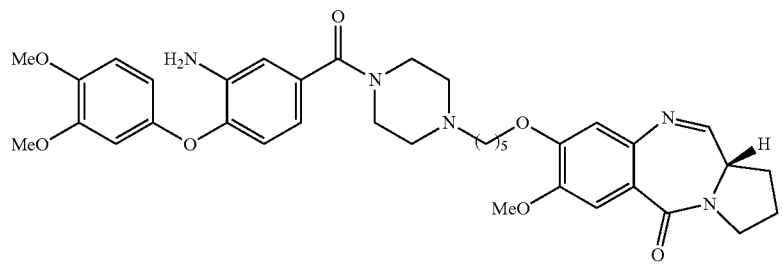
(23d)
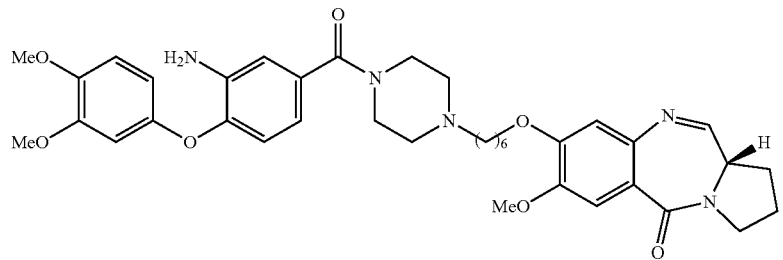
(24a)
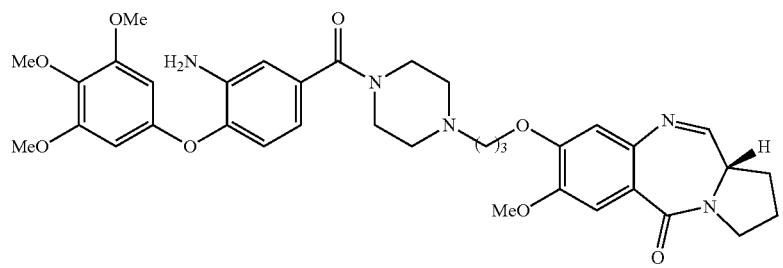
(24b)
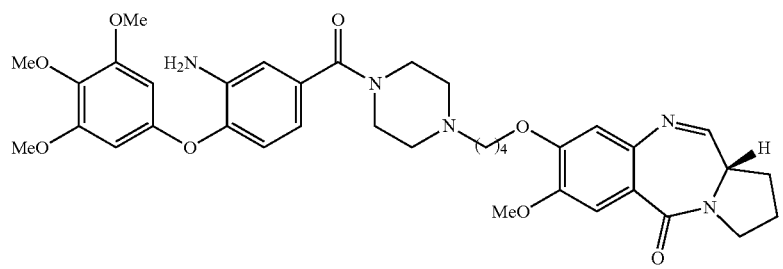
(24c)
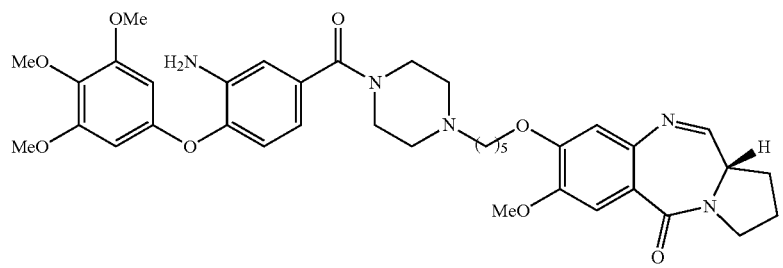
(24d)
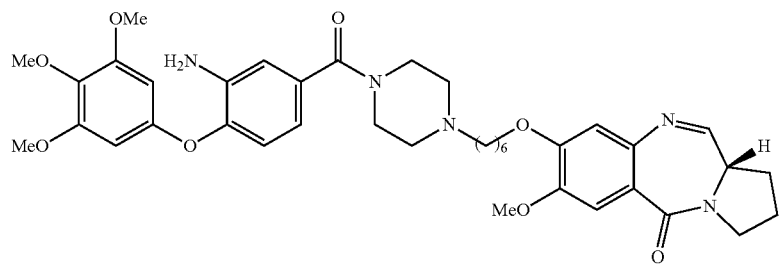

(25a)
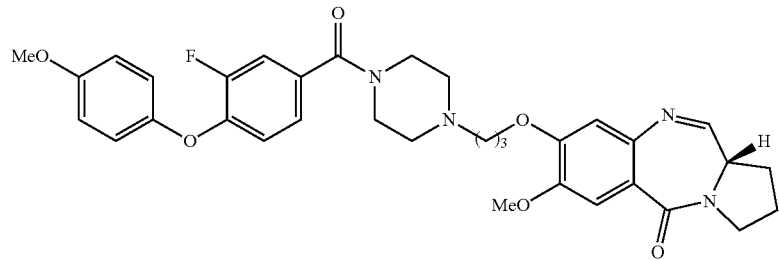
(25b)
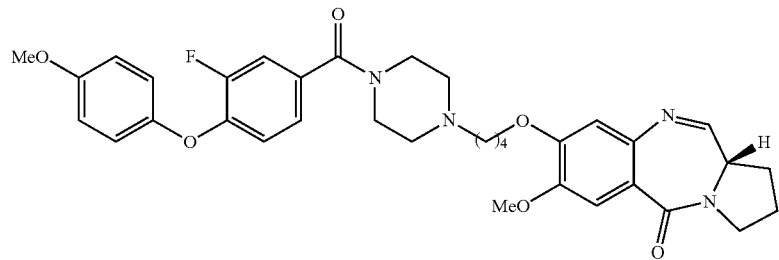
(25c)
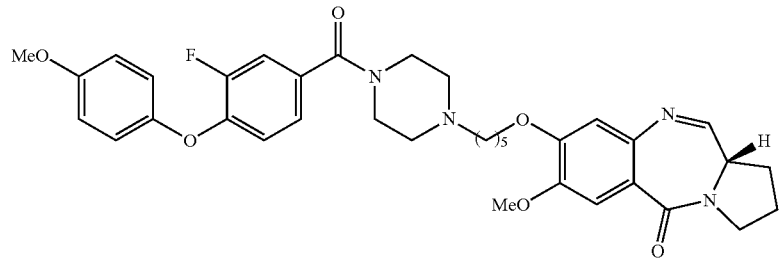
(25d)
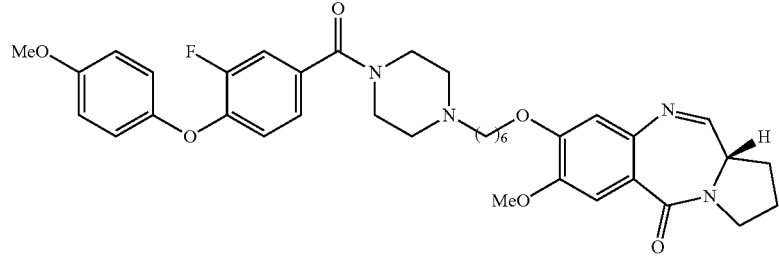
(26a)
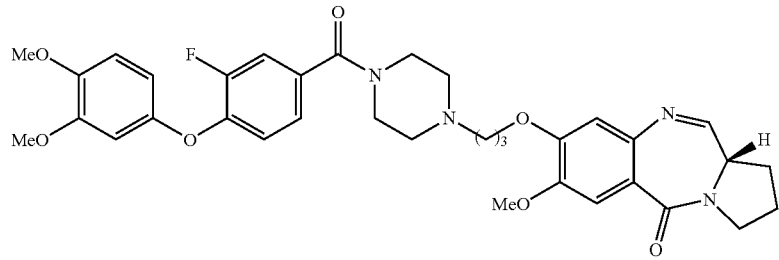
(26b)
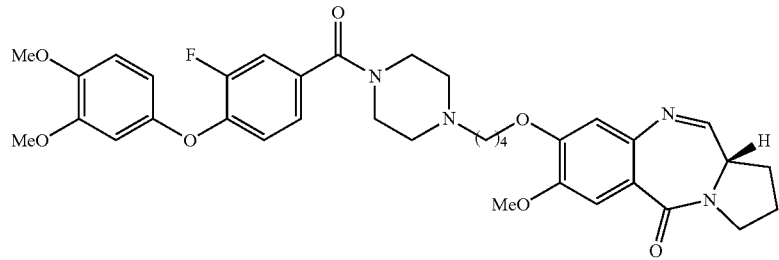

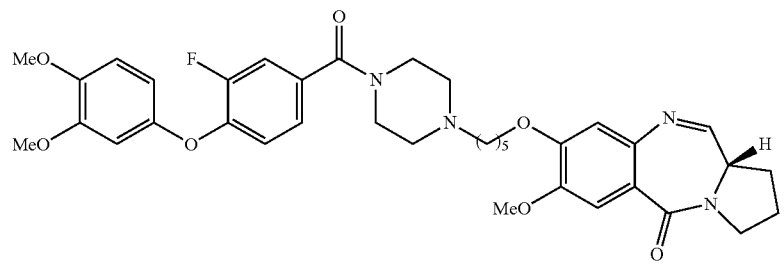
(26c)
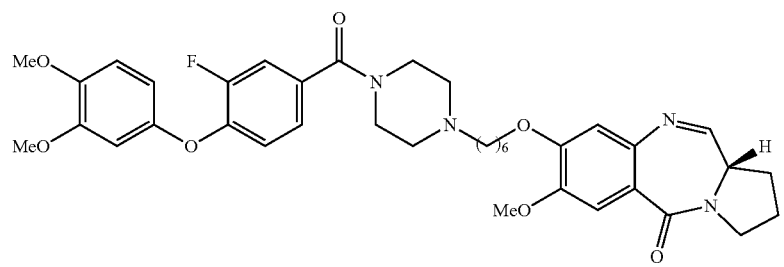
(26d)
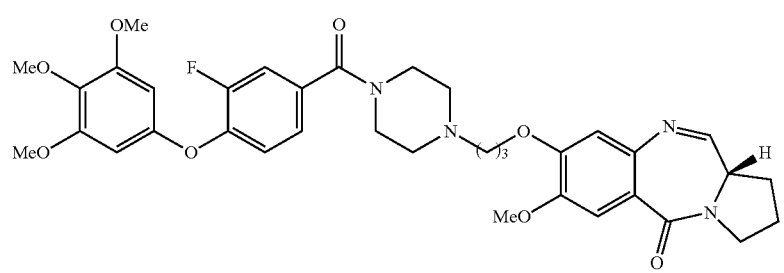
(27a)
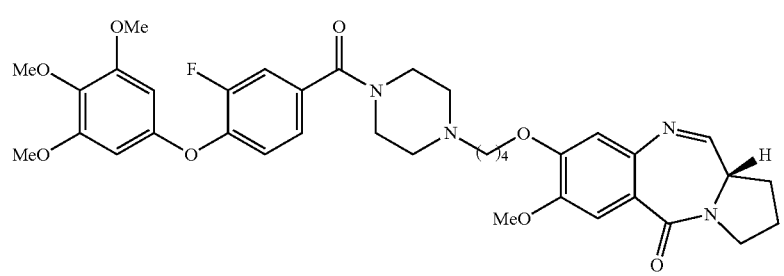
(27b)
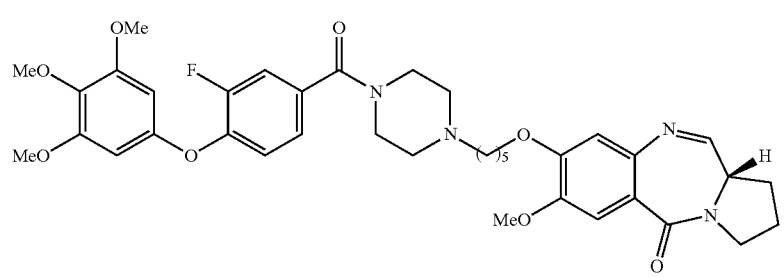
(27c)
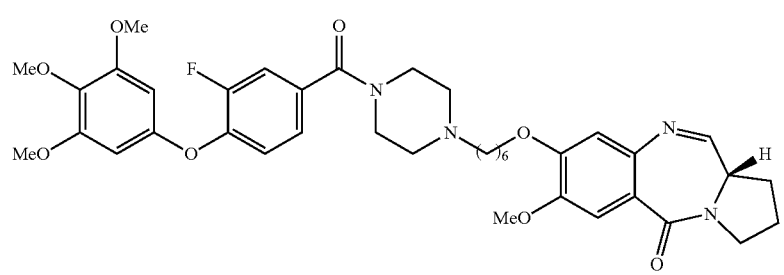
(27d)

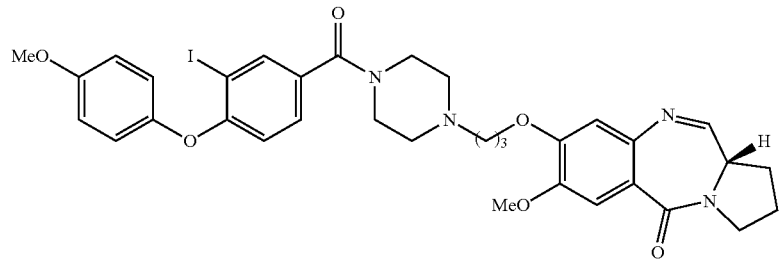
(28a)
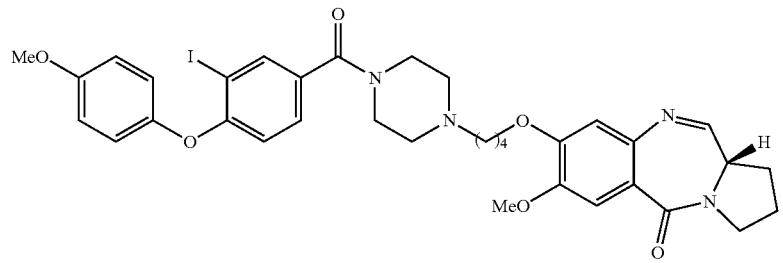
(28b)
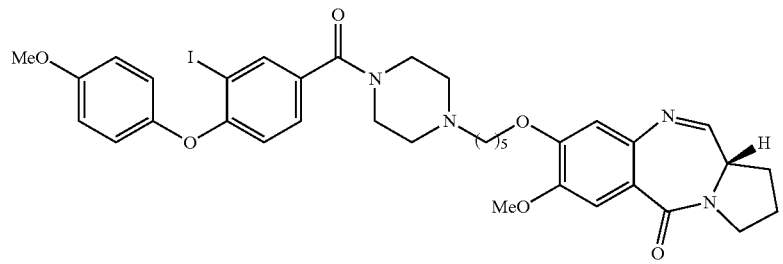
(28c)
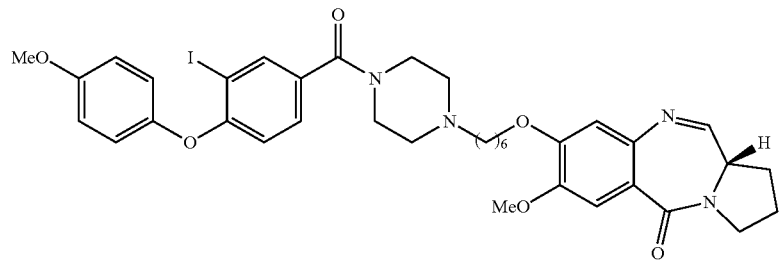
(28d)
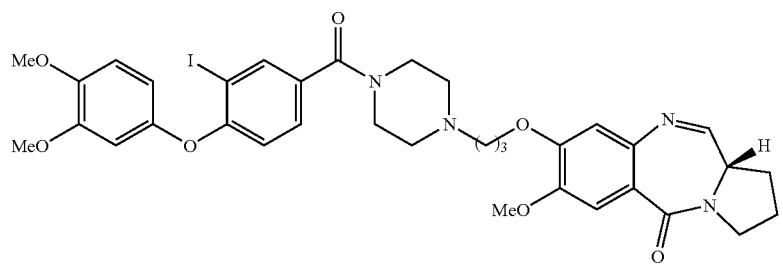
(29a)
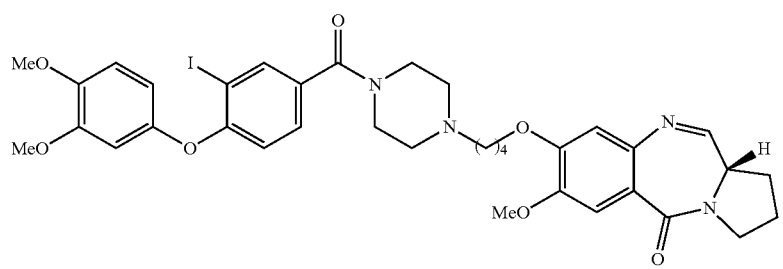
(29b)

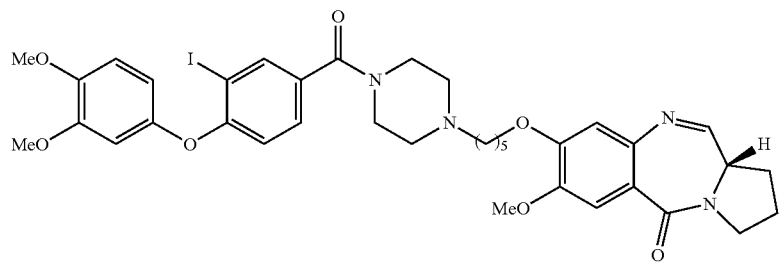
(29c)
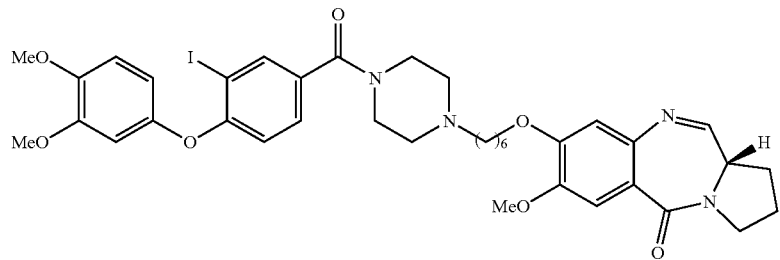
(29d)
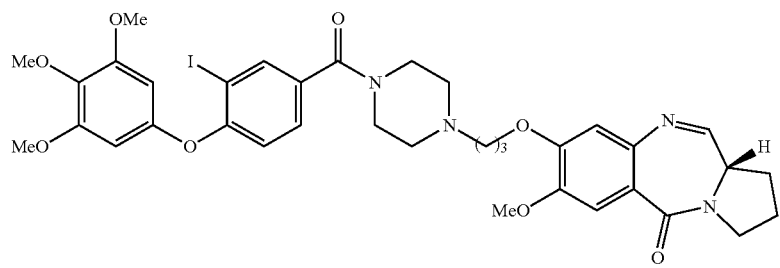
(30a)
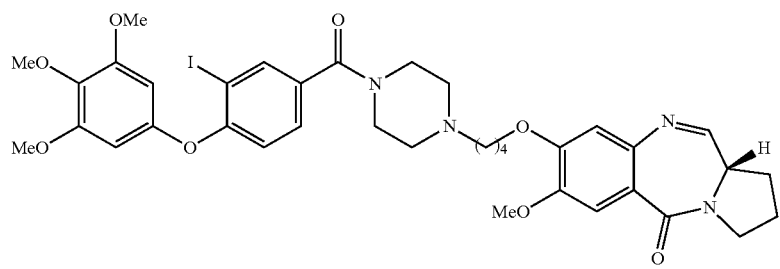
(30b)
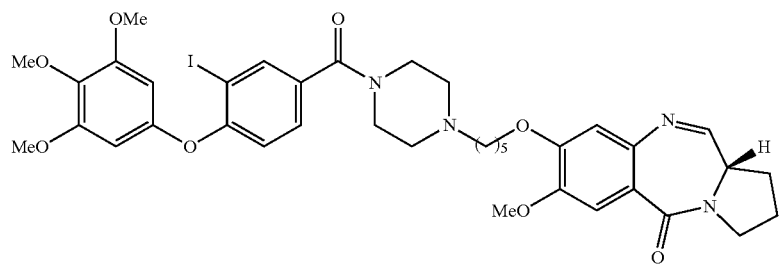
(30c)
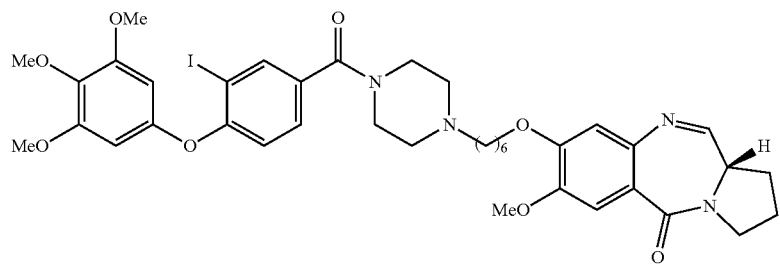
(30d)

-continued
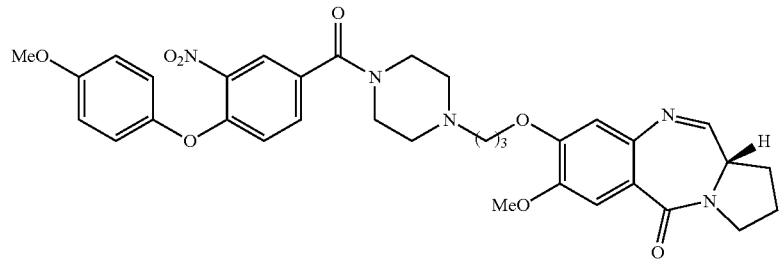
(31a)
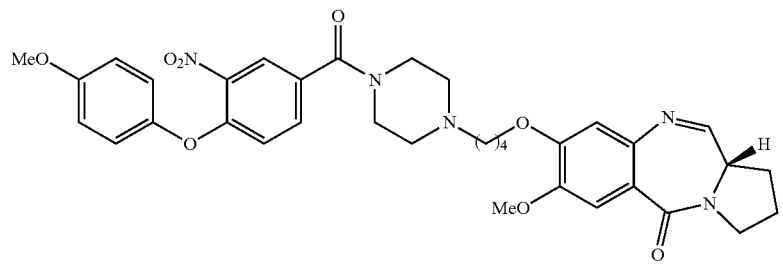
(31b)
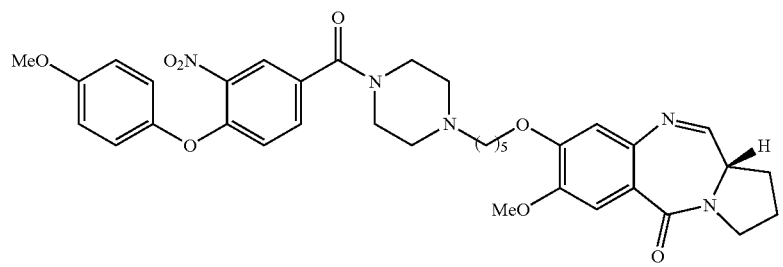
(31c)
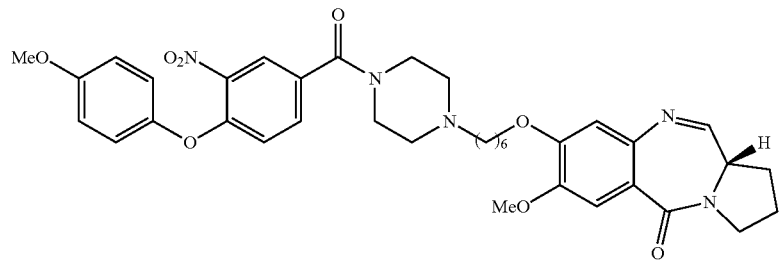
(31d)
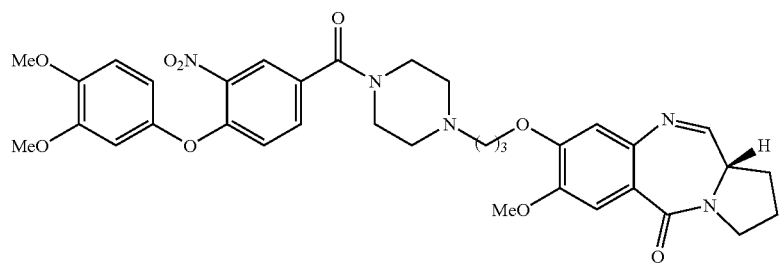
(32a)
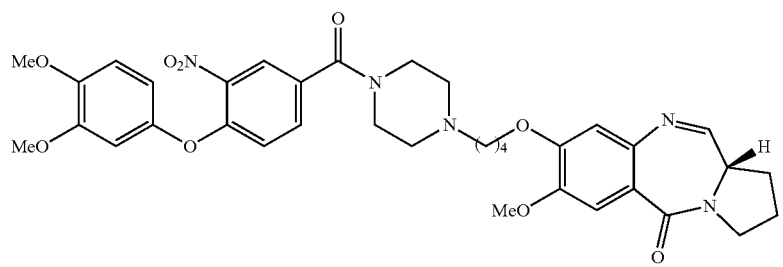
(32b)

(32c)
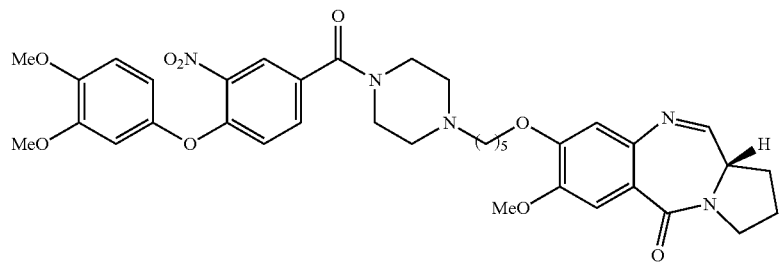
(32d)
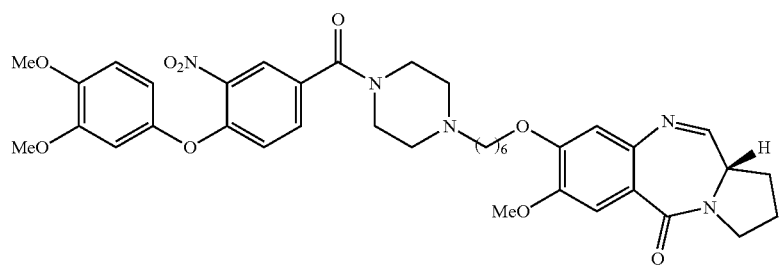
(33a)
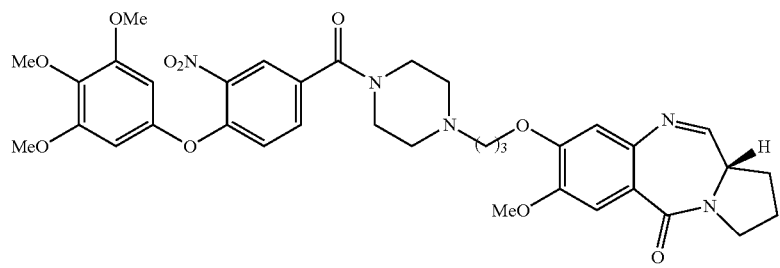
(33b)
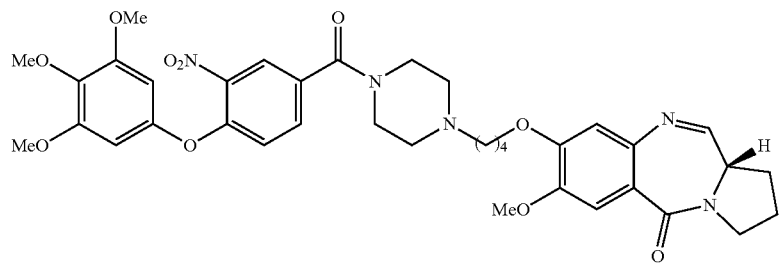
(33c)
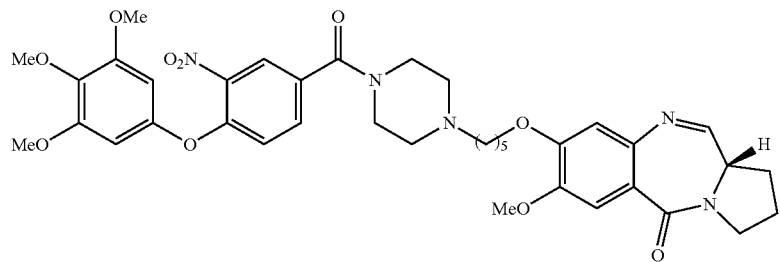
(33d)
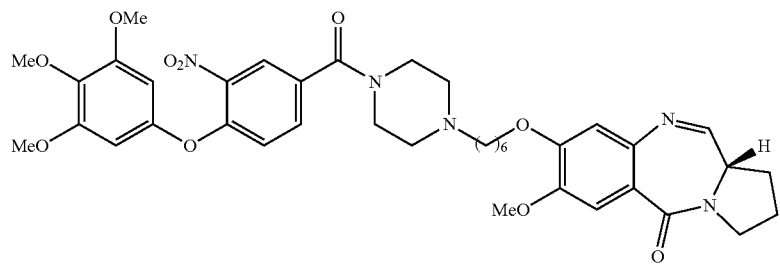

16. The compound of claim 1, having formula (31c):
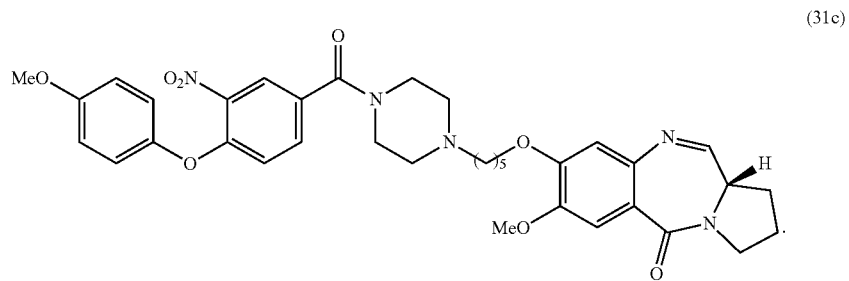
(31c)
17. The compound of claim 1, having formula (32c):
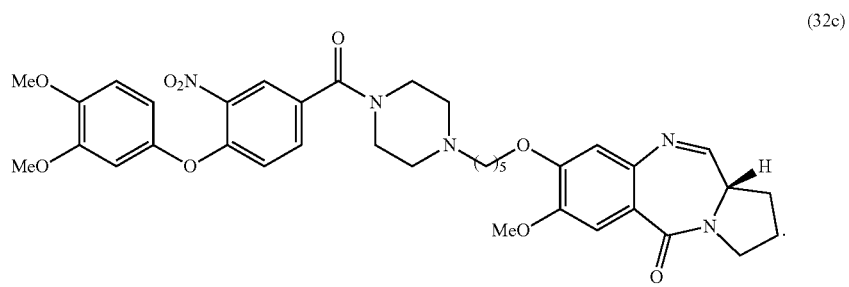
(32c)
18. The compound of claim 1, having formula (33c):
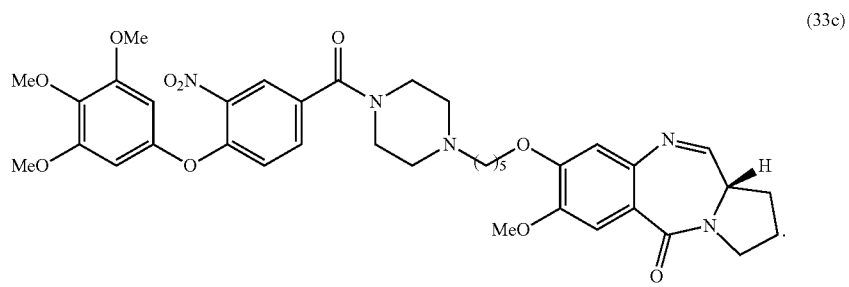
(33c)
19. The method of claim 14, wherein the compound is selected from the group consisting of:
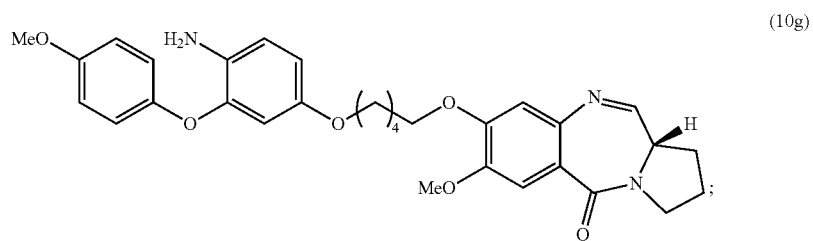
(10g)
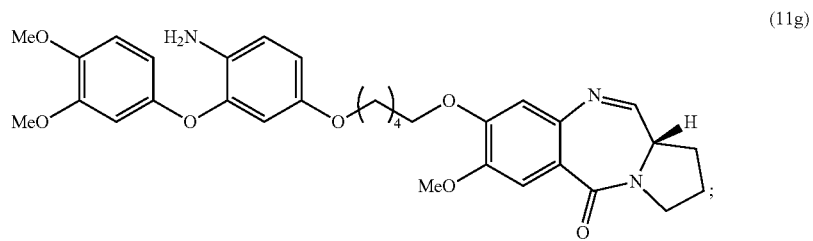
(11g)

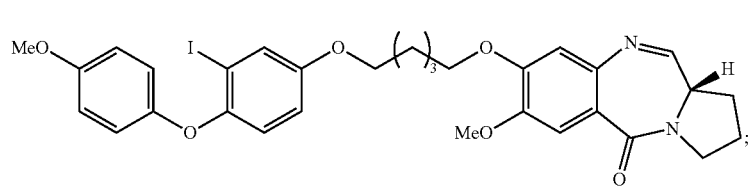
(16c)
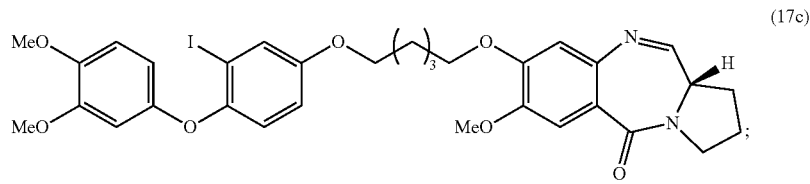
(17c)
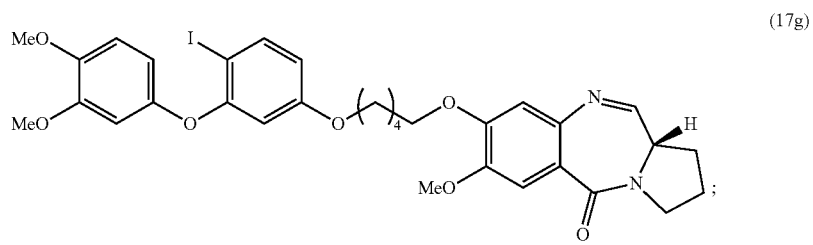
(17g)
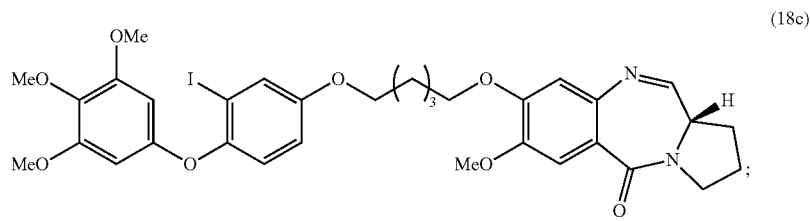
(18c)
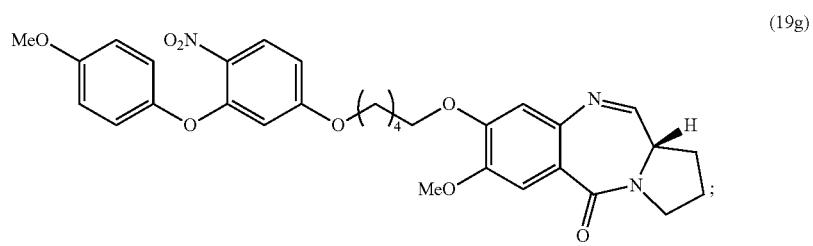
(19g)
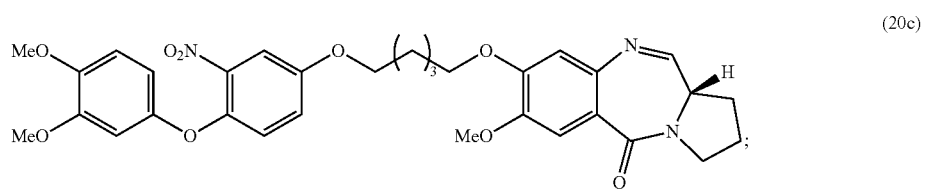
(20c)
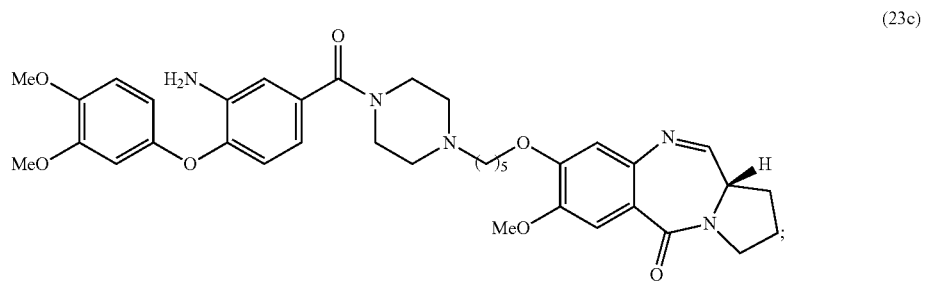
(23c)

-continued
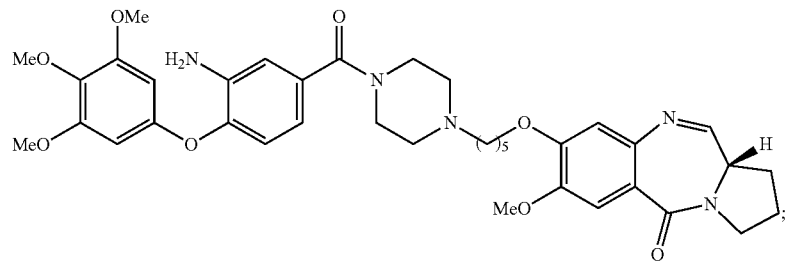
(24c)
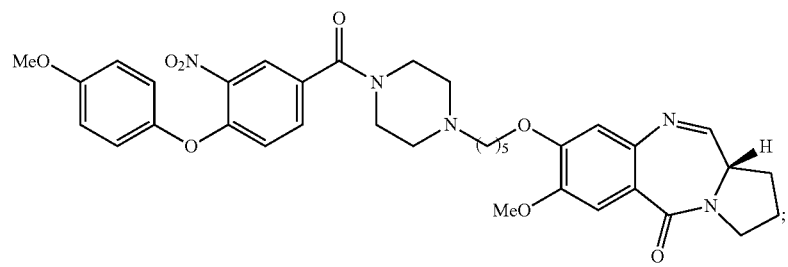
(31c)
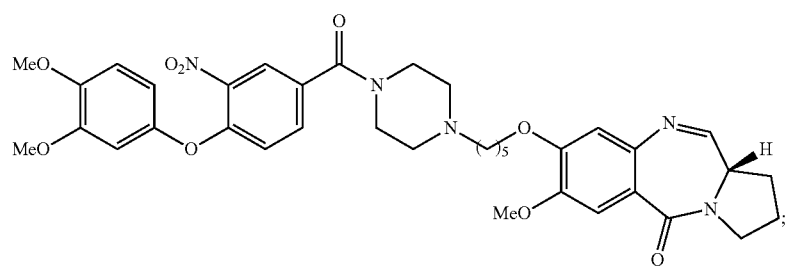
(32c)
and
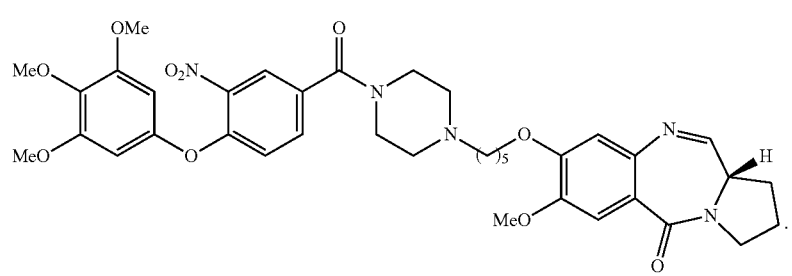
(33c)
* * * * *